US011389295B2

(12) United States Patent
McLean

(10) Patent No.: US 11,389,295 B2
(45) Date of Patent: Jul. 19, 2022

(54) DELIVERY SYSTEMS WITH TETHERS FOR PROSTHETIC HEART VALVE DEVICES AND ASSOCIATED METHODS

(71) Applicant: Twelve, Inc., Redwood City, CA (US)

(72) Inventor: Matthew McLean, San Francisco, CA (US)

(73) Assignee: Twelve, Inc., Redwood City ( * ) Notice: Subject to any disclaimer, the term of this patent is extended or adjusted under 35 U.S.C. 154(b) by 477 days.

(21) Appl. No.: 16/584,461

(22) Filed: Sep. 26, 2019

(65) Prior Publication Data

US 2020/0038184 A1 Feb. 6, 2020

Related U.S. Application Data

(62) Division of application No. 15/490,024, filed on Apr. 18, 2017, now Pat. No. 10,433,961.

(51) Int. Cl.
*A61F 2/24* (2006.01)
*A61F 2/95* (2013.01)

(52) U.S. Cl.
CPC ............ *A61F 2/2439* (2013.01); *A61F 2/243* (2013.01); *A61F 2/2409* (2013.01);
(Continued)

(58) Field of Classification Search
CPC ........ A61F 2/24; A61F 2/2436; A61F 2/2439; A61F 2220/0016; A61F 2250/0069; A61F 2002/9534; A61F 2/2409; A61F 2/243
See application file for complete search history.

(56) References Cited

U.S. PATENT DOCUMENTS

| 3,526,219 A | 9/1970 | Balanmuth |
|---|---|---|
| 3,565,062 A | 2/1971 | Kuris |

(Continued)

FOREIGN PATENT DOCUMENTS

| CN | 1440261 | 9/2003 |
|---|---|---|
| CN | 101076290 | 11/2007 |

(Continued)

OTHER PUBLICATIONS

US 9,265,606 B2, 02/2016, Buchbinder et al. (withdrawn)

(Continued)

*Primary Examiner* — George J Ulsh
(74) *Attorney, Agent, or Firm* — Medler Ferro Woodhouse & Mills PLLC

(57) ABSTRACT

Delivery systems with tethers for prosthetic heart valve devices and associated methods are disclosed herein. A delivery system configured in accordance with embodiments of the present technology can include, for example, an elongated catheter body, a capsule carried by the elongated catheter body and carrying a prosthetic heart valve device, and a cinching member slidably disposed within the capsule. The delivery system can further include a plurality of tether elements coupled to the prosthetic device and extending through the cinching member and the catheter body. Retraction of the tether elements can urge at least a portion of the prosthetic device into a distal end portion of the cinching member to resheathe at least a portion of the prosthetic device and allow repositioning of the prosthetic device relative to the native valve after a portion of the prosthetic device has contacted tissue of a native valve.

16 Claims, 19 Drawing Sheets

(52) U.S. Cl.
CPC .... *A61F 2/2436* (2013.01); *A61F 2002/9534* (2013.01); *A61F 2220/0016* (2013.01); *A61F 2250/0069* (2013.01)

(56) References Cited

U.S. PATENT DOCUMENTS

| | | | |
|---|---|---|---|
| 3,589,363 A | 6/1971 | Banko et al. |
| 3,667,474 A | 6/1972 | Lapkin et al. |
| 3,823,717 A | 7/1974 | Pohlman et al. |
| 3,861,391 A | 1/1975 | Antonevich et al. |
| 3,896,811 A | 7/1975 | Storz |
| 4,042,979 A | 8/1977 | Angell |
| 4,188,952 A | 2/1980 | Loschilov et al. |
| 4,431,006 A | 2/1984 | Trimmer et al. |
| 4,445,509 A | 5/1984 | Auth |
| 4,484,579 A | 11/1984 | Meno et al. |
| 4,490,859 A | 1/1985 | Black et al. |
| 4,587,958 A | 5/1986 | Noguchi et al. |
| 4,589,419 A | 5/1986 | Laughlin et al. |
| 4,602,911 A | 7/1986 | Ahmadi et al. |
| 4,646,736 A | 3/1987 | Auth |
| 4,692,139 A | 9/1987 | Stiles |
| 4,747,821 A | 5/1988 | Kensey et al. |
| 4,750,902 A | 6/1988 | Wuchinich et al. |
| 4,777,951 A | 10/1988 | Cribier et al. |
| 4,787,388 A | 11/1988 | Hofmann |
| 4,796,629 A | 1/1989 | Grayzel |
| 4,808,153 A | 2/1989 | Parisi |
| 4,819,751 A | 4/1989 | Shimada et al. |
| 4,841,977 A | 6/1989 | Griffith et al. |
| 4,870,953 A | 10/1989 | DonMicheal et al. |
| 4,878,495 A | 11/1989 | Grayzel |
| 4,898,575 A | 2/1990 | Fischell et al. |
| 4,909,252 A | 3/1990 | Goldberger |
| 4,919,133 A | 4/1990 | Chiang |
| 4,920,954 A | 5/1990 | Alliger et al. |
| 4,936,281 A | 6/1990 | Stasz |
| 4,960,411 A | 10/1990 | Buchbinder |
| 4,986,830 A | 1/1991 | Owens et al. |
| 4,990,134 A | 2/1991 | Auth |
| 5,058,570 A | 10/1991 | Idemoto et al. |
| 5,069,664 A | 12/1991 | Guess et al. |
| 5,076,276 A | 12/1991 | Sakurai et al. |
| 5,106,302 A | 4/1992 | Farzin-Nia et al. |
| 5,248,296 A | 9/1993 | Alliger |
| 5,267,954 A | 12/1993 | Nita |
| 5,269,291 A | 12/1993 | Carter |
| 5,295,958 A | 3/1994 | Shturman |
| 5,304,115 A | 4/1994 | Pflueger et al. |
| 5,314,407 A | 5/1994 | Auth et al. |
| 5,318,014 A | 6/1994 | Carter |
| 5,332,402 A | 7/1994 | Teitelbaum |
| 5,344,426 A | 9/1994 | Lau et al. |
| 5,352,199 A | 10/1994 | Tower |
| 5,356,418 A | 10/1994 | Shturman |
| 5,397,293 A | 3/1995 | Alliger et al. |
| 5,411,552 A | 5/1995 | Andersen et al. |
| 5,443,446 A | 8/1995 | Shturman |
| 5,449,373 A | 9/1995 | Pinchasik et al. |
| 5,489,297 A | 2/1996 | Duran |
| 5,584,879 A | 12/1996 | Reimold et al. |
| 5,609,151 A | 3/1997 | Mulier et al. |
| 5,626,603 A | 5/1997 | Venturelli et al. |
| 5,656,036 A | 8/1997 | Palmaz |
| 5,662,671 A | 9/1997 | Barbut et al. |
| 5,681,336 A | 10/1997 | Clement et al. |
| 5,695,507 A | 12/1997 | Auth et al. |
| 5,725,494 A | 3/1998 | Brisken |
| 5,782,931 A | 7/1998 | Yang et al. |
| 5,817,101 A | 10/1998 | Fiedler |
| 5,827,229 A | 10/1998 | Auth et al. |
| 5,827,321 A | 10/1998 | Roubin et al. |
| 5,840,081 A | 11/1998 | Andersen et al. |
| 5,853,422 A | 12/1998 | Huebsch et al. |
| 5,855,601 A | 1/1999 | Bessler et al. |
| 5,868,781 A | 2/1999 | Killion |
| 5,873,811 A | 2/1999 | Wang et al. |
| 5,904,679 A | 5/1999 | Clayman |
| 5,957,882 A | 9/1999 | Nita et al. |
| 5,972,004 A | 10/1999 | Williamson, IV et al. |
| 5,989,208 A | 11/1999 | Nita |
| 5,989,280 A | 11/1999 | Euteneuer et al. |
| 6,047,700 A | 4/2000 | Eggers et al. |
| 6,056,759 A | 5/2000 | Fiedler |
| 6,085,754 A | 7/2000 | Alferness et al. |
| 6,113,608 A | 9/2000 | Monroe et al. |
| RE36,939 E | 10/2000 | Tachibana et al. |
| 6,129,734 A | 10/2000 | Shturman et al. |
| 6,132,444 A | 10/2000 | Shturman et al. |
| 6,168,579 B1 | 1/2001 | Tsugita |
| 6,217,595 B1 | 4/2001 | Shturman et al. |
| 6,254,635 B1 | 7/2001 | Schroeder et al. |
| 6,295,712 B1 | 10/2001 | Shturman et al. |
| 6,306,414 B1 | 10/2001 | Koike |
| 6,321,109 B2 | 11/2001 | Ben-Haim et al. |
| 6,402,679 B1 | 6/2002 | Mortier et al. |
| 6,423,032 B2 | 7/2002 | Parodi |
| 6,425,916 B1 | 7/2002 | Garrison et al. |
| 6,440,164 B1 | 8/2002 | DiMatteo et al. |
| 6,454,737 B1 | 9/2002 | Nita et al. |
| 6,454,757 B1 | 9/2002 | Nita et al. |
| 6,454,799 B1 | 9/2002 | Schreck |
| 6,458,153 B1 | 10/2002 | Bailey et al. |
| 6,461,382 B1 | 10/2002 | Cao |
| 6,494,890 B1 | 12/2002 | Shturman et al. |
| 6,494,891 B1 | 12/2002 | Cornish et al. |
| 6,505,080 B1 | 1/2003 | Sutton |
| 6,530,952 B2 | 3/2003 | Vesely |
| 6,540,782 B1 | 4/2003 | Snyders |
| 6,562,067 B2 | 5/2003 | Mathis |
| 6,565,588 B1 | 5/2003 | Clement et al. |
| 6,569,196 B1 | 5/2003 | Vesely |
| 6,579,308 B1 | 6/2003 | Jansen et al. |
| 6,582,462 B1 | 6/2003 | Andersen et al. |
| 6,595,912 B2 | 7/2003 | Lau et al. |
| 6,605,109 B2 | 8/2003 | Fiedler |
| 6,616,689 B1 | 9/2003 | Ainsworth et al. |
| 6,623,452 B2 | 9/2003 | Chien et al. |
| 6,638,288 B1 | 10/2003 | Shturman et al. |
| 6,648,854 B1 | 11/2003 | Patterson et al. |
| 6,689,086 B1 | 2/2004 | Nita et al. |
| 6,702,748 B1 | 3/2004 | Nita et al. |
| 6,730,121 B2 | 5/2004 | Ortiz et al. |
| 6,746,463 B1 | 6/2004 | Schwartz |
| 6,811,801 B2 | 11/2004 | Nguyen et al. |
| 6,818,001 B2 | 11/2004 | Wulfman et al. |
| 6,843,797 B2 | 1/2005 | Nash et al. |
| 6,852,118 B2 | 2/2005 | Shturman et al. |
| 6,855,123 B2 | 2/2005 | Nita |
| 6,869,439 B2 | 3/2005 | White et al. |
| 6,951,571 B1 | 10/2005 | Srivastava |
| 6,986,775 B2 | 1/2006 | Morales et al. |
| 7,018,404 B2 | 3/2006 | Holmberg et al. |
| 7,052,487 B2 | 5/2006 | Cohn et al. |
| 7,077,861 B2 | 7/2006 | Spence |
| 7,125,420 B2 | 10/2006 | Rourke et al. |
| 7,186,264 B2 | 3/2007 | Liddicoat et al. |
| 7,261,732 B2 | 8/2007 | Justino |
| 7,296,577 B2 | 11/2007 | Lashinski et al. |
| 7,381,218 B2 | 6/2008 | Schreck |
| 7,404,824 B1 | 7/2008 | Webler et al. |
| 7,442,204 B2 | 10/2008 | Schwammenthal et al. |
| 7,473,275 B2 | 1/2009 | Marquez |
| 7,510,575 B2 | 3/2009 | Spenser et al. |
| 7,585,321 B2 | 9/2009 | Cribier |
| 7,588,582 B2 | 9/2009 | Starksen et al. |
| 7,621,948 B2 | 11/2009 | Herrmann et al. |
| 7,708,775 B2 | 5/2010 | Rowe et al. |
| 7,748,389 B2 | 7/2010 | Salahieh et al. |
| 7,753,922 B2 | 7/2010 | Starksen |
| 7,753,949 B2 | 7/2010 | Lamphere et al. |
| 7,803,168 B2 | 9/2010 | Gifford et al. |
| 7,857,845 B2 | 12/2010 | Stacchino et al. |
| 7,896,915 B2 | 3/2011 | Guyenot et al. |

(56) References Cited

U.S. PATENT DOCUMENTS

| | | |
|---|---|---|
| 7,942,928 B2 | 5/2011 | Webler et al. |
| 8,002,826 B2 | 8/2011 | Seguin |
| 8,052,750 B2 | 11/2011 | Tuval et al. |
| 8,062,355 B2 | 11/2011 | Figulla et al. |
| 8,109,996 B2 | 2/2012 | Stacchino et al. |
| 8,114,154 B2 | 2/2012 | Righini et al. |
| 8,252,051 B2 | 8/2012 | Chau et al. |
| 8,398,704 B2 | 3/2013 | Straubinger et al. |
| 8,403,981 B2 | 3/2013 | Forster et al. |
| 8,403,983 B2 | 3/2013 | Quadri et al. |
| 8,414,643 B2 | 4/2013 | Tuval et al. |
| 8,449,599 B2 | 5/2013 | Chau et al. |
| 8,496,671 B1 | 7/2013 | Hausen |
| 8,512,252 B2 | 8/2013 | Ludomirsky et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,540,767 B2 | 9/2013 | Zhang |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 | 12/2013 | Gross et al. |
| 8,623,077 B2 | 1/2014 | Cohn |
| 8,628,566 B2 | 1/2014 | Eberhardt et al. |
| 8,632,585 B2 | 1/2014 | Seguin et al. |
| 8,632,586 B2 | 1/2014 | Spenser et al. |
| 8,634,935 B2 | 1/2014 | Gaudiani |
| 8,647,254 B2 | 2/2014 | Callas et al. |
| 8,652,203 B2 | 2/2014 | Quadri et al. |
| 8,652,204 B2 | 2/2014 | Quill et al. |
| 8,657,872 B2 | 2/2014 | Seguin |
| 8,672,998 B2 | 3/2014 | Lichtenstein et al. |
| 8,673,001 B2 | 3/2014 | Cartledge et al. |
| 8,679,176 B2 | 3/2014 | Matheny |
| 8,685,086 B2 | 4/2014 | Navia et al. |
| 8,688,234 B2 | 4/2014 | Zhu et al. |
| 8,690,858 B2 | 4/2014 | Machold et al. |
| 8,709,074 B2 | 4/2014 | Solem et al. |
| 8,712,133 B2 | 4/2014 | Guhring et al. |
| 8,715,160 B2 | 5/2014 | Raman et al. |
| 8,721,665 B2 | 5/2014 | Oz et al. |
| 8,721,718 B2 | 5/2014 | Kassab |
| 8,740,918 B2 | 6/2014 | Seguin |
| 8,747,460 B2 | 6/2014 | Tuval et al. |
| 8,758,431 B2 | 6/2014 | Orlov et al. |
| 8,758,432 B2 | 6/2014 | Solem |
| 8,771,292 B2 | 7/2014 | Allen et al. |
| 8,771,345 B2 | 7/2014 | Tuval et al. |
| 8,771,346 B2 | 7/2014 | Tuval et al. |
| 8,777,991 B2 | 7/2014 | Zarbatany et al. |
| 8,778,016 B2 | 7/2014 | Janovsky et al. |
| 8,781,580 B2 | 7/2014 | Hedberg et al. |
| 8,784,482 B2 | 7/2014 | Randert et al. |
| 8,792,699 B2 | 7/2014 | Guetter et al. |
| 8,795,356 B2 | 8/2014 | Quadri et al. |
| 8,801,779 B2 | 8/2014 | Seguin et al. |
| 8,808,356 B2 | 8/2014 | Braido et al. |
| 8,808,366 B2 | 8/2014 | Braido et al. |
| 8,812,431 B2 | 8/2014 | Voigt et al. |
| 8,828,043 B2 | 9/2014 | Chambers |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 8,858,622 B2 | 10/2014 | Machold et al. |
| 8,859,724 B2 | 10/2014 | Meier et al. |
| 8,864,822 B2 | 10/2014 | Spence et al. |
| 8,870,936 B2 | 10/2014 | Rowe |
| 8,870,948 B1 | 10/2014 | Erzberger et al. |
| 8,870,949 B2 | 10/2014 | Rowe |
| 8,894,702 B2 | 11/2014 | Quadri et al. |
| 8,900,295 B2 | 12/2014 | Migliazza et al. |
| 8,926,694 B2 | 1/2015 | Costello |
| 8,932,348 B2 | 1/2015 | Solem et al. |
| 8,951,285 B2 | 2/2015 | Sugimoto et al. |
| 8,961,597 B2 | 2/2015 | Subramanian et al. |
| 8,968,393 B2 | 3/2015 | Rothstein |
| 8,968,395 B2 | 3/2015 | Hauser et al. |
| 8,974,445 B2 | 3/2015 | Warnking et al. |
| 8,979,922 B2 | 3/2015 | Jayasinghe et al. |
| 8,979,923 B2 | 3/2015 | Spence et al. |
| 8,986,370 B2 | 3/2015 | Annest |
| 8,986,376 B2 | 3/2015 | Solem |
| 8,992,604 B2 | 3/2015 | Gross et al. |
| 9,011,522 B2 | 4/2015 | Annest |
| 9,011,523 B2 | 4/2015 | Seguin |
| 9,017,399 B2 | 4/2015 | Gross et al. |
| 9,023,098 B2 | 5/2015 | Kuehn |
| 9,023,100 B2 | 5/2015 | Quadri et al. |
| 9,050,188 B2 | 6/2015 | Schweich, Jr. et al. |
| 9,066,800 B2 | 6/2015 | Clague et al. |
| 9,084,676 B2 | 7/2015 | Chau et al. |
| 9,095,433 B2 | 8/2015 | Lutter et al. |
| 9,119,713 B2 | 9/2015 | Board et al. |
| 9,132,009 B2 | 9/2015 | Hacohen et al. |
| 9,138,312 B2 | 9/2015 | Tuval et al. |
| 9,138,313 B2 | 9/2015 | McGuckin, Jr. et al. |
| 9,180,005 B1 | 11/2015 | Lashinski et al. |
| 9,192,466 B2 | 11/2015 | Kovalsky et al. |
| 9,192,471 B2 | 11/2015 | Bolling |
| 9,232,942 B2 | 1/2016 | Seguin et al. |
| 9,232,999 B2 | 1/2016 | Maurer et al. |
| 9,241,790 B2 | 1/2016 | Lane et al. |
| 9,248,014 B2 | 2/2016 | Lane et al. |
| 9,254,192 B2 | 2/2016 | Lutter et al. |
| 9,271,833 B2 | 3/2016 | Kim et al. |
| 9,289,291 B2 | 3/2016 | Gorman, III et al. |
| 9,289,297 B2 | 3/2016 | Wilson et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,358,108 B2 | 6/2016 | Bortlein et al. |
| 9,387,075 B2 | 7/2016 | Bortlein et al. |
| 9,387,078 B2 | 7/2016 | Gross et al. |
| 9,393,111 B2 | 7/2016 | Ma et al. |
| 9,629,719 B2 | 4/2017 | Rothstein et al. |
| 9,675,454 B2 | 6/2017 | Vidlund et al. |
| 9,681,951 B2 | 6/2017 | Ratz et al. |
| 9,687,342 B2 | 6/2017 | Figulla et al. |
| 9,687,343 B2 | 6/2017 | Bortlein et al. |
| 9,693,859 B2 | 7/2017 | Braido et al. |
| 9,693,862 B2 | 7/2017 | Campbell et al. |
| 9,694,121 B2 | 7/2017 | Alexander et al. |
| 9,700,409 B2 | 7/2017 | Braido et al. |
| 9,700,411 B2 | 7/2017 | Klima et al. |
| 9,730,791 B2 | 8/2017 | Ratz et al. |
| 9,730,794 B2 | 8/2017 | Carpentier et al. |
| 9,750,605 B2 | 9/2017 | Ganesan et al. |
| 9,750,606 B2 | 9/2017 | Ganesan et al. |
| 9,750,607 B2 | 9/2017 | Ganesan et al. |
| 9,763,657 B2 | 9/2017 | Hacohen et al. |
| 9,763,658 B2 | 9/2017 | Eigler et al. |
| 9,763,782 B2 | 9/2017 | Solem et al. |
| 9,770,328 B2 | 9/2017 | Macoviak et al. |
| 9,788,931 B2 | 10/2017 | Giordano et al. |
| 9,801,717 B2 | 10/2017 | Edquist et al. |
| 9,827,092 B2 | 11/2017 | Vidlund et al. |
| 9,827,101 B2 | 11/2017 | Solem et al. |
| 9,833,313 B2 | 12/2017 | Board et al. |
| 9,833,315 B2 | 12/2017 | Vidlund et al. |
| 9,839,511 B2 | 12/2017 | Ma et al. |
| 9,844,435 B2 | 12/2017 | Eidenschink |
| 9,848,880 B2 | 12/2017 | Coleman et al. |
| 9,848,983 B2 | 12/2017 | Lashinski et al. |

(56) References Cited

U.S. PATENT DOCUMENTS

| | | |
|---|---|---|
| 9,861,477 B2 | 1/2018 | Backus et al. |
| 9,861,480 B2 | 1/2018 | Zakai et al. |
| 10,433,961 B2 | 10/2019 | McLean |
| 2001/0021872 A1 | 9/2001 | Bailey et al. |
| 2001/0049492 A1 | 12/2001 | Frazier et al. |
| 2002/0007219 A1 | 1/2002 | Merrill et al. |
| 2002/0013571 A1 | 1/2002 | Goldfarb et al. |
| 2002/0072792 A1 | 6/2002 | Burgermeister et al. |
| 2002/0082637 A1 | 6/2002 | Lumauig |
| 2002/0099439 A1 | 7/2002 | Schwartz et al. |
| 2002/0138138 A1 | 9/2002 | Yang |
| 2002/0151970 A1 | 10/2002 | Garrison et al. |
| 2002/0173841 A1 | 11/2002 | Ortiz et al. |
| 2003/0120340 A1 | 6/2003 | Liska et al. |
| 2003/0139689 A1 | 7/2003 | Shturman et al. |
| 2004/0006358 A1 | 1/2004 | Wulfman et al. |
| 2004/0039412 A1 | 2/2004 | Isshiki et al. |
| 2004/0044350 A1 | 3/2004 | Martin et al. |
| 2004/0057955 A1 | 3/2004 | O'Brien et al. |
| 2004/0082910 A1 | 4/2004 | Constantz et al. |
| 2004/0092858 A1 | 5/2004 | Wilson et al. |
| 2004/0092962 A1 | 5/2004 | Thornton et al. |
| 2004/0092989 A1 | 5/2004 | Wilson et al. |
| 2004/0106989 A1 | 6/2004 | Wilson et al. |
| 2004/0117009 A1 | 6/2004 | Cali et al. |
| 2004/0122510 A1 | 6/2004 | Sarac |
| 2004/0127979 A1 | 7/2004 | Wilson et al. |
| 2004/0127982 A1 | 7/2004 | Machold et al. |
| 2004/0186558 A1 | 9/2004 | Pavcnik et al. |
| 2004/0199191 A1 | 10/2004 | Schwartz |
| 2004/0220655 A1 | 11/2004 | Swanson et al. |
| 2004/0230117 A1 | 11/2004 | Tosaya et al. |
| 2004/0230212 A1 | 11/2004 | Wulfman |
| 2004/0230213 A1 | 11/2004 | Wulfman et al. |
| 2004/0243162 A1 | 12/2004 | Wulfman et al. |
| 2005/0007219 A1 | 1/2005 | Ma et al. |
| 2005/0075662 A1 | 4/2005 | Pedersen et al. |
| 2005/0075720 A1 | 4/2005 | Nguyen et al. |
| 2005/0075727 A1 | 4/2005 | Wheatley |
| 2005/0107661 A1 | 5/2005 | Lau et al. |
| 2005/0137682 A1 | 6/2005 | Justino |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137700 A1 | 6/2005 | Spence et al. |
| 2005/0137701 A1 | 6/2005 | Salahieh et al. |
| 2005/0137702 A1 | 6/2005 | Haug et al. |
| 2005/0228477 A1 | 10/2005 | Grainger et al. |
| 2005/0267523 A1 | 12/2005 | Devellian et al. |
| 2005/0273135 A1 | 12/2005 | Chanduszko |
| 2006/0058872 A1 | 3/2006 | Salahieh et al. |
| 2006/0106456 A9 | 5/2006 | Machold et al. |
| 2006/0149360 A1 | 7/2006 | Schwammenthal et al. |
| 2006/0167543 A1 | 7/2006 | Bailey et al. |
| 2006/0195183 A1 | 8/2006 | Navia et al. |
| 2006/0253191 A1 | 11/2006 | Salahieh et al. |
| 2006/0287719 A1 | 12/2006 | Rowe et al. |
| 2007/0056346 A1 | 3/2007 | Spencer et al. |
| 2007/0061010 A1 | 3/2007 | Hauser et al. |
| 2007/0073391 A1 | 3/2007 | Bourang et al. |
| 2007/0078302 A1 | 4/2007 | Ortiz et al. |
| 2007/0088431 A1 | 4/2007 | Bourang et al. |
| 2007/0142906 A1 | 6/2007 | Figulla et al. |
| 2007/0173932 A1 | 7/2007 | Cali et al. |
| 2008/0071369 A1 | 3/2008 | Tuval et al. |
| 2008/0082166 A1 | 4/2008 | Styrc et al. |
| 2008/0103586 A1 | 5/2008 | Styrc et al. |
| 2008/0140189 A1 | 6/2008 | Nguyen et al. |
| 2008/0208332 A1 | 8/2008 | Lamphere et al. |
| 2008/0221672 A1 | 9/2008 | Lamphere et al. |
| 2008/0234728 A1 | 9/2008 | Starksen et al. |
| 2008/0243245 A1 | 10/2008 | Thambar et al. |
| 2008/0243246 A1 | 10/2008 | Ryan et al. |
| 2009/0054969 A1 | 2/2009 | Salahieh et al. |
| 2009/0076586 A1 | 3/2009 | Hauser et al. |
| 2009/0076598 A1 | 3/2009 | Salahieh et al. |
| 2009/0093670 A1 | 4/2009 | Annest et al. |
| 2009/0157174 A1 | 6/2009 | Yoganathan et al. |
| 2009/0164006 A1 | 6/2009 | Seguin et al. |
| 2009/0198315 A1 | 8/2009 | Boudjemline |
| 2009/0216312 A1 | 8/2009 | Straubinger et al. |
| 2009/0240320 A1 | 9/2009 | Tuval et al. |
| 2009/0259292 A1 | 10/2009 | Bonhoeffer |
| 2009/0259306 A1 | 10/2009 | Rowe |
| 2009/0264997 A1 | 10/2009 | Salahieh et al. |
| 2009/0276040 A1 | 11/2009 | Rowe et al. |
| 2009/0281609 A1 | 11/2009 | Benichou et al. |
| 2009/0281618 A1 | 11/2009 | Hill et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2009/0319038 A1 | 12/2009 | Gurskis et al. |
| 2010/0016958 A1 | 1/2010 | St. Goar et al. |
| 2010/0023115 A1 | 1/2010 | Robaina et al. |
| 2010/0023117 A1 | 1/2010 | Yoganathan et al. |
| 2010/0030330 A1 | 2/2010 | Bobo et al. |
| 2010/0049313 A1 | 2/2010 | Alon et al. |
| 2010/0076548 A1 | 3/2010 | Konno |
| 2010/0082094 A1 | 4/2010 | Quadri et al. |
| 2010/0094411 A1 | 4/2010 | Tuval et al. |
| 2010/0121436 A1 | 5/2010 | Tuval et al. |
| 2010/0185275 A1 | 7/2010 | Richter et al. |
| 2010/0204770 A1 | 8/2010 | Mas et al. |
| 2010/0217382 A1 | 8/2010 | Chau et al. |
| 2010/0249915 A1 | 9/2010 | Zhang |
| 2010/0249923 A1 | 9/2010 | Alkhatib et al. |
| 2010/0298929 A1 | 11/2010 | Thornton et al. |
| 2010/0298931 A1 | 11/2010 | Quadri et al. |
| 2010/0312333 A1 | 12/2010 | Navia et al. |
| 2010/0324554 A1 | 12/2010 | Gifford et al. |
| 2011/0004296 A1 | 1/2011 | Lutter et al. |
| 2011/0015722 A1 | 1/2011 | Hauser et al. |
| 2011/0022166 A1 | 1/2011 | Dahlgren et al. |
| 2011/0029071 A1 | 2/2011 | Zlotnick et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0153008 A1 | 6/2011 | Marchand et al. |
| 2011/0172784 A1 | 7/2011 | Richter et al. |
| 2011/0184512 A1 | 7/2011 | Webler et al. |
| 2011/0208293 A1 | 8/2011 | Tabor |
| 2011/0224785 A1 | 9/2011 | Hacohen |
| 2011/0319988 A1 | 12/2011 | Schankereli et al. |
| 2012/0022639 A1 | 1/2012 | Hacohen et al. |
| 2012/0035703 A1 | 2/2012 | Lutter et al. |
| 2012/0035713 A1 | 2/2012 | Lutter et al. |
| 2012/0053680 A1 | 3/2012 | Bolling et al. |
| 2012/0053682 A1 | 3/2012 | Kovalsky et al. |
| 2012/0078347 A1 | 3/2012 | Braido et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0179239 A1 | 7/2012 | Quadri |
| 2012/0179244 A1 | 7/2012 | Schankereli et al. |
| 2012/0203336 A1 | 8/2012 | Annest |
| 2012/0283824 A1 | 11/2012 | Lutter et al. |
| 2013/0172978 A1 | 7/2013 | Vidlund et al. |
| 2013/0190860 A1 | 7/2013 | Sundt, III |
| 2013/0190861 A1 | 7/2013 | Chau et al. |
| 2013/0197354 A1 | 8/2013 | Maschke et al. |
| 2013/0197630 A1 | 8/2013 | Azarnoush |
| 2013/0204356 A1 | 8/2013 | Dwork et al. |
| 2013/0204358 A1 | 8/2013 | Matheny |
| 2013/0226289 A1 | 8/2013 | Shaolian et al. |
| 2013/0226290 A1 | 8/2013 | Yellin et al. |
| 2013/0231735 A1 | 9/2013 | Deem et al. |

(56) References Cited

U.S. PATENT DOCUMENTS

| | | |
|---|---|---|
| 2013/0238089 A1 | 9/2013 | Lichtenstein et al. |
| 2013/0244927 A1 | 9/2013 | Lal et al. |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0259337 A1 | 10/2013 | Guhring et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261741 A1 | 10/2013 | Accola |
| 2013/0268066 A1 | 10/2013 | Rowe |
| 2013/0274870 A1 | 10/2013 | Lombardi et al. |
| 2013/0282059 A1 | 10/2013 | Ketai et al. |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |
| 2013/0289717 A1 | 10/2013 | Solem |
| 2013/0289718 A1 | 10/2013 | Tsukashima et al. |
| 2013/0296851 A1 | 11/2013 | Boronyak et al. |
| 2013/0296999 A1 | 11/2013 | Burriesci et al. |
| 2013/0304180 A1 | 11/2013 | Green et al. |
| 2013/0304181 A1 | 11/2013 | Green et al. |
| 2013/0304197 A1 | 11/2013 | Buchbinder et al. |
| 2013/0304198 A1 | 11/2013 | Solem |
| 2013/0304200 A1 | 11/2013 | Mclean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1 | 11/2013 | Morriss et al. |
| 2013/0317603 A1 | 11/2013 | Mclean et al. |
| 2013/0325110 A1 | 12/2013 | Khalil et al. |
| 2013/0325114 A1 | 12/2013 | Mclean et al. |
| 2013/0331864 A1 | 12/2013 | Jelich et al. |
| 2013/0338684 A1 | 12/2013 | Hausen |
| 2013/0338763 A1 | 12/2013 | Rowe et al. |
| 2013/0345797 A1 | 12/2013 | Dahlgren et al. |
| 2013/0345803 A1 | 12/2013 | Bergheim, III |
| 2014/0005778 A1 | 1/2014 | Buchbinder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1 | 1/2014 | Murphy et al. |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0094906 A1 | 4/2014 | Spence et al. |
| 2014/0107775 A1 | 4/2014 | Hjelle et al. |
| 2014/0114404 A1 | 4/2014 | Gammie et al. |
| 2014/0114407 A1 | 4/2014 | Rajamannan |
| 2014/0121763 A1 | 5/2014 | Duffy et al. |
| 2014/0128965 A1 | 5/2014 | Rafiee |
| 2014/0135913 A1 | 5/2014 | Lichtenstein et al. |
| 2014/0163652 A1 | 6/2014 | Witzel et al. |
| 2014/0163668 A1 | 6/2014 | Rafiee |
| 2014/0172076 A1 | 6/2014 | Jonsson et al. |
| 2014/0172084 A1 | 6/2014 | Callas et al. |
| 2014/0172085 A1 | 6/2014 | Quadri et al. |
| 2014/0172086 A1 | 6/2014 | Quadri et al. |
| 2014/0179993 A1 | 6/2014 | Alexander et al. |
| 2014/0180401 A1 | 6/2014 | Quill et al. |
| 2014/0188108 A1 | 7/2014 | Goodine et al. |
| 2014/0188215 A1 | 7/2014 | Hlavka et al. |
| 2014/0194920 A1 | 7/2014 | Krahbichler |
| 2014/0194976 A1 | 7/2014 | Starksen et al. |
| 2014/0200397 A1 | 7/2014 | Raman et al. |
| 2014/0200649 A1 | 7/2014 | Essinger et al. |
| 2014/0200657 A1 | 7/2014 | Maurer et al. |
| 2014/0200662 A1 | 7/2014 | Eftel et al. |
| 2014/0214159 A1 | 7/2014 | Vidlund et al. |
| 2014/0219524 A1 | 8/2014 | Takeguchi et al. |
| 2014/0222040 A1 | 8/2014 | Park et al. |
| 2014/0222138 A1 | 8/2014 | Machold et al. |
| 2014/0228942 A1 | 8/2014 | Krahbichler |
| 2014/0228946 A1 | 8/2014 | Chau et al. |
| 2014/0236278 A1 | 8/2014 | Argentine et al. |
| 2014/0242086 A1 | 8/2014 | Lal et al. |
| 2014/0243860 A1 | 8/2014 | Morris et al. |
| 2014/0243954 A1 | 8/2014 | Shannon |
| 2014/0243964 A1 | 8/2014 | Venkatasubramanian |
| 2014/0249621 A1 | 9/2014 | Eidenschink |
| 2014/0257101 A1 | 9/2014 | Gaudiani |
| 2014/0257466 A1 | 9/2014 | Board et al. |
| 2014/0257467 A1 | 9/2014 | Lane et al. |
| 2014/0257473 A1 | 9/2014 | Rajamannan |
| 2014/0257475 A1 | 9/2014 | Gross et al. |
| 2014/0275757 A1 | 9/2014 | Goodwin et al. |
| 2014/0276395 A1 | 9/2014 | Wilson et al. |
| 2014/0276609 A1 | 9/2014 | Magee et al. |
| 2014/0276782 A1 | 9/2014 | Paskar |
| 2014/0276971 A1 | 9/2014 | Kovach |
| 2014/0277119 A1 | 9/2014 | Akpinar |
| 2014/0277390 A1 | 9/2014 | Ratz et al. |
| 2014/0277404 A1 | 9/2014 | Wilson et al. |
| 2014/0277405 A1 | 9/2014 | Wilson et al. |
| 2014/0277406 A1 | 9/2014 | Arcidi |
| 2014/0277407 A1 | 9/2014 | Dale et al. |
| 2014/0277408 A1 | 9/2014 | Folan |
| 2014/0277409 A1 | 9/2014 | Bortlein et al. |
| 2014/0277410 A1 | 9/2014 | Bortlein et al. |
| 2014/0277411 A1 | 9/2014 | Bortlein et al. |
| 2014/0277412 A1 | 9/2014 | Bortlein et al. |
| 2014/0277420 A1 | 9/2014 | Migliazza et al. |
| 2014/0277422 A1 | 9/2014 | Ratz et al. |
| 2014/0288480 A1 | 9/2014 | Zimmerman et al. |
| 2014/0296878 A1 | 10/2014 | Oz et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296975 A1 | 10/2014 | Tegels et al. |
| 2014/0303719 A1 | 10/2014 | Cox et al. |
| 2014/0303721 A1 | 10/2014 | Fung et al. |
| 2014/0309727 A1 | 10/2014 | Lamelas et al. |
| 2014/0309730 A1 | 10/2014 | Alon et al. |
| 2014/0309731 A1 | 10/2014 | Quadri et al. |
| 2014/0309732 A1 | 10/2014 | Solem |
| 2014/0316516 A1 | 10/2014 | Vidlund et al. |
| 2014/0324164 A1 | 10/2014 | Gross et al. |
| 2014/0330368 A1 | 11/2014 | Gloss et al. |
| 2014/0358222 A1 | 12/2014 | Gorman, III et al. |
| 2014/0358224 A1 | 12/2014 | Tegels et al. |
| 2014/0364944 A1 | 12/2014 | Lutter et al. |
| 2014/0371843 A1 | 12/2014 | Wilson et al. |
| 2014/0371844 A1 | 12/2014 | Dale et al. |
| 2014/0371846 A1 | 12/2014 | Wilson et al. |
| 2014/0379074 A1 | 12/2014 | Spence et al. |
| 2014/0379076 A1 | 12/2014 | Vidlund et al. |
| 2015/0005874 A1 | 1/2015 | Vidlund et al. |
| 2015/0005875 A1 | 1/2015 | Tuval et al. |
| 2015/0025623 A1 | 1/2015 | Granada et al. |
| 2015/0032127 A1 | 1/2015 | Gammie et al. |
| 2015/0045878 A1 | 2/2015 | Rowe |
| 2015/0066140 A1 | 3/2015 | Quadri et al. |
| 2015/0094802 A1 | 4/2015 | Buchbinder et al. |
| 2015/0094803 A1 | 4/2015 | Navia |
| 2015/0100116 A1 | 4/2015 | Mohl et al. |
| 2015/0112427 A1 | 4/2015 | Schweich, Jr. et al. |
| 2015/0112429 A1 | 4/2015 | Khairkhahan et al. |
| 2015/0112433 A1 | 4/2015 | Schweich, Jr. et al. |
| 2015/0119978 A1 | 4/2015 | Tegels et al. |
| 2015/0119981 A1 | 4/2015 | Khairkhahan et al. |
| 2015/0119982 A1 | 4/2015 | Quill et al. |
| 2015/0127091 A1 | 5/2015 | Cecere et al. |
| 2015/0127096 A1 | 5/2015 | Rowe et al. |

(56) References Cited

U.S. PATENT DOCUMENTS

| | | |
|---|---|---|
| 2015/0142101 A1 | 5/2015 | Coleman et al. |
| 2015/0142103 A1 | 5/2015 | Vidlund |
| 2015/0142105 A1 | 5/2015 | Bolling et al. |
| 2015/0150678 A1 | 6/2015 | Brecker |
| 2015/0157458 A1 | 6/2015 | Thambar et al. |
| 2015/0157459 A1 | 6/2015 | Macoviak et al. |
| 2015/0164637 A1 | 6/2015 | Khairkhahan et al. |
| 2015/0164641 A1 | 6/2015 | Annest |
| 2015/0173897 A1 | 6/2015 | Raanani et al. |
| 2015/0173898 A1 | 6/2015 | Drasler et al. |
| 2015/0173900 A1 | 6/2015 | Hauser et al. |
| 2015/0190229 A1 | 7/2015 | Seguin |
| 2015/0196390 A1 | 7/2015 | Ma et al. |
| 2015/0196393 A1 | 7/2015 | Vidlund et al. |
| 2015/0202043 A1 | 7/2015 | Zakai et al. |
| 2015/0209137 A1 | 7/2015 | Quadri et al. |
| 2015/0209139 A1 | 7/2015 | Granada et al. |
| 2015/0216655 A1 | 8/2015 | Lane et al. |
| 2015/0216661 A1 | 8/2015 | Hacohen et al. |
| 2015/0223802 A1 | 8/2015 | Tegzes |
| 2015/0223934 A1 | 8/2015 | Vidlund et al. |
| 2015/0223935 A1 | 8/2015 | Subramanian et al. |
| 2015/0230920 A1 | 8/2015 | Alfieri et al. |
| 2015/0230921 A1 | 8/2015 | Chau et al. |
| 2015/0238312 A1 | 8/2015 | Lashinski |
| 2015/0238313 A1 | 8/2015 | Spence et al. |
| 2015/0250590 A1 | 9/2015 | Gries et al. |
| 2015/0257877 A1 | 9/2015 | Hernandez |
| 2015/0257878 A1 | 9/2015 | Lane et al. |
| 2015/0257879 A1 | 9/2015 | Bortlein et al. |
| 2015/0257881 A1 | 9/2015 | Bortlein et al. |
| 2015/0257882 A1 | 9/2015 | Bortlein et al. |
| 2015/0272737 A1 | 10/2015 | Dale et al. |
| 2015/0305861 A1 | 10/2015 | Annest |
| 2015/0305864 A1 | 10/2015 | Quadri et al. |
| 2015/0313739 A1 | 11/2015 | Hummen et al. |
| 2015/0320553 A1 | 11/2015 | Chau et al. |
| 2015/0327999 A1 | 11/2015 | Board et al. |
| 2015/0328000 A1 | 11/2015 | Ratz et al. |
| 2015/0342733 A1 | 12/2015 | Alkhatib et al. |
| 2015/0351906 A1 | 12/2015 | Hammer et al. |
| 2015/0351908 A1 | 12/2015 | Keranen et al. |
| 2015/0359628 A1 | 12/2015 | Keranen |
| 2015/0359629 A1 | 12/2015 | Ganesan et al. |
| 2015/0359631 A1 | 12/2015 | Sheahan et al. |
| 2015/0366666 A1 | 12/2015 | Khairkhahan et al. |
| 2015/0374495 A1 | 12/2015 | Ruyra Baliarda et al. |
| 2016/0000983 A1 | 1/2016 | Mohl et al. |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0015543 A1 | 1/2016 | Perouse et al. |
| 2016/0030171 A1 | 2/2016 | Quijano et al. |
| 2016/0038246 A1 | 2/2016 | Wang et al. |
| 2016/0038280 A1 | 2/2016 | Morriss et al. |
| 2016/0038283 A1 | 2/2016 | Divekar et al. |
| 2016/0038286 A1 | 2/2016 | Yellin et al. |
| 2016/0074160 A1 | 3/2016 | Christianson et al. |
| 2016/0106539 A1 | 4/2016 | Buchbinder et al. |
| 2016/0113764 A1 | 4/2016 | Sheahan et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120643 A1 | 5/2016 | Kupumbati |
| 2016/0143730 A1 | 5/2016 | Kheradvar |
| 2016/0151154 A1 | 6/2016 | Gorman, III et al. |
| 2016/0151156 A1 | 6/2016 | Seguin et al. |
| 2016/0151552 A1 | 6/2016 | Solem |
| 2016/0157999 A1 | 6/2016 | Lane et al. |
| 2016/0158000 A1 | 6/2016 | Granada et al. |
| 2016/0158001 A1 | 6/2016 | Wallace et al. |
| 2016/0158002 A1 | 6/2016 | Wallace et al. |
| 2016/0158003 A1 | 6/2016 | Wallace et al. |
| 2016/0184095 A1 | 6/2016 | Spence et al. |
| 2016/0206280 A1 | 7/2016 | Vidlund et al. |
| 2016/0206424 A1 | 7/2016 | Al-Jilaihawi et al. |
| 2016/0262881 A1 | 9/2016 | Schankereli et al. |
| 2016/0317290 A1 | 11/2016 | Chau et al. |
| 2017/0079790 A1 | 3/2017 | Vidlund et al. |
| 2017/0100248 A1 | 4/2017 | Tegels et al. |
| 2017/0100250 A1 | 4/2017 | Marsot et al. |
| 2017/0119526 A1 | 5/2017 | Luong et al. |
| 2017/0128198 A1 | 5/2017 | Cartledge et al. |
| 2017/0128205 A1 | 5/2017 | Tamir et al. |
| 2017/0128206 A1 | 5/2017 | Rafiee et al. |
| 2017/0128208 A1 | 5/2017 | Christianson et al. |
| 2017/0156860 A1 | 6/2017 | Lashinski |
| 2017/0165054 A1 | 6/2017 | Benson et al. |
| 2017/0165055 A1 | 6/2017 | Hauser et al. |
| 2017/0165064 A1 | 6/2017 | Nyuli et al. |
| 2017/0172737 A1 | 6/2017 | Kuetting et al. |
| 2017/0181851 A1 | 6/2017 | Annest |
| 2017/0189177 A1 | 7/2017 | Schweich, Jr. et al. |
| 2017/0189179 A1 | 7/2017 | Ratz et al. |
| 2017/0189180 A1 | 7/2017 | Alkhatib |
| 2017/0189181 A1 | 7/2017 | Alkhatib et al. |
| 2017/0196688 A1 | 7/2017 | Christianson et al. |
| 2017/0231762 A1 | 8/2017 | Quadri et al. |
| 2017/0231763 A1 | 8/2017 | Yellin et al. |
| 2017/0258585 A1 | 9/2017 | Marquez et al. |
| 2017/0266001 A1 | 9/2017 | Vidlund et al. |
| 2017/0281345 A1 | 10/2017 | Yang et al. |
| 2017/0290659 A1 | 10/2017 | Ulmer et al. |
| 2017/0296338 A1 | 10/2017 | Cambell et al. |
| 2017/0296339 A1 | 10/2017 | Thambar et al. |
| 2017/0319333 A1 | 11/2017 | Tegels et al. |
| 2017/0325842 A1 | 11/2017 | Siegel |
| 2017/0325941 A1 | 11/2017 | Wallace et al. |
| 2017/0325945 A1 | 11/2017 | Dale et al. |
| 2017/0325948 A1 | 11/2017 | Wallace et al. |
| 2017/0325949 A1 | 11/2017 | Rodgers et al. |
| 2017/0325953 A1 | 11/2017 | Klima et al. |
| 2017/0325954 A1 | 11/2017 | Perszyk |
| 2017/0333186 A1 | 11/2017 | Spargias |
| 2017/0333188 A1 | 11/2017 | Carpentier et al. |
| 2017/0340440 A1 | 11/2017 | Ratz et al. |
| 2017/0348097 A1 | 12/2017 | Taft et al. |
| 2017/0348098 A1 | 12/2017 | Rowe et al. |
| 2017/0348100 A1 | 12/2017 | Lane et al. |
| 2017/0354496 A1 | 12/2017 | Quadri et al. |
| 2017/0354497 A1 | 12/2017 | Quadri et al. |
| 2017/0354499 A1 | 12/2017 | Granada et al. |
| 2017/0360426 A1 | 12/2017 | Hacohen et al. |
| 2017/0360549 A1 | 12/2017 | Lashinski et al. |
| 2017/0360558 A1 | 12/2017 | Ma |
| 2017/0360585 A1 | 12/2017 | White |
| 2017/0361065 A1 | 12/2017 | Legaspi et al. |
| 2018/0000584 A1 | 1/2018 | Duffy et al. |
| 2018/0296325 A1 | 10/2018 | McLean |

FOREIGN PATENT DOCUMENTS

| | | |
|---|---|---|
| CN | 101291637 | 10/2008 |
| CN | 103491900 | 1/2014 |
| CN | 105007865 A | 10/2015 |
| CN | 205729576 U | 11/2016 |
| DE | 19605042 | 1/1998 |
| DE | 102006052564 | 12/2007 |
| EP | 186104 | 7/1986 |
| EP | 1512383 | 3/2005 |
| EP | 1545371 | 6/2005 |
| EP | 1551274 | 7/2005 |
| EP | 1629794 | 3/2006 |
| EP | 1646332 | 4/2006 |
| EP | 1702247 | 9/2006 |
| EP | 1734903 | 12/2006 |
| EP | 1891914 | 2/2008 |
| EP | 2026280 | 2/2009 |
| EP | 2037829 | 3/2009 |
| EP | 2081519 | 7/2009 |
| EP | 2111190 | 10/2009 |
| EP | 2142143 | 1/2010 |
| EP | 2167742 | 3/2010 |
| EP | 2278944 | 2/2011 |

(56) References Cited

FOREIGN PATENT DOCUMENTS

| | | |
|---|---|---|
| EP | 2306821 | 4/2011 |
| EP | 2327429 | 6/2011 |
| EP | 2400924 | 1/2012 |
| EP | 2400926 | 1/2012 |
| EP | 2410947 | 2/2012 |
| EP | 2416739 | 2/2012 |
| EP | 2419050 | 2/2012 |
| EP | 2444031 | 4/2012 |
| EP | 2488126 | 8/2012 |
| EP | 2509538 | 10/2012 |
| EP | 2549955 | 1/2013 |
| EP | 2549956 | 1/2013 |
| EP | 2566416 | 3/2013 |
| EP | 2586492 | 5/2013 |
| EP | 2618784 | 7/2013 |
| EP | 2623068 | 8/2013 |
| EP | 2626013 | 8/2013 |
| EP | 2629699 | 8/2013 |
| EP | 2633457 | 9/2013 |
| EP | 2637659 | 9/2013 |
| EP | 2641569 | 9/2013 |
| EP | 2644158 | 10/2013 |
| EP | 2654624 | 10/2013 |
| EP | 2656794 | 10/2013 |
| EP | 2656795 | 10/2013 |
| EP | 2656796 | 10/2013 |
| EP | 2667823 | 12/2013 |
| EP | 2670358 | 12/2013 |
| EP | 2676640 | 12/2013 |
| EP | 2688041 | 1/2014 |
| EP | 2695586 | 2/2014 |
| EP | 2697721 | 2/2014 |
| EP | 2713953 | 4/2014 |
| EP | 2714068 | 4/2014 |
| EP | 2723272 | 4/2014 |
| EP | 2723273 | 4/2014 |
| EP | 2723277 | 4/2014 |
| EP | 2739214 | 6/2014 |
| EP | 2741711 | 6/2014 |
| EP | 2750630 | 7/2014 |
| EP | 2750631 | 7/2014 |
| EP | 2755562 | 7/2014 |
| EP | 2755602 | 7/2014 |
| EP | 2757962 | 7/2014 |
| EP | 2777616 | 9/2014 |
| EP | 2777617 | 9/2014 |
| EP | 2782523 | 10/2014 |
| EP | 2785282 | 10/2014 |
| EP | 2786817 | 10/2014 |
| EP | 2790609 | 10/2014 |
| EP | 2793751 | 10/2014 |
| EP | 2809263 | 12/2014 |
| EP | 2810620 | 12/2014 |
| EP | 2814428 | 12/2014 |
| EP | 2814429 | 12/2014 |
| EP | 2819617 | 1/2015 |
| EP | 2819618 | 1/2015 |
| EP | 2819619 | 1/2015 |
| EP | 2717803 | 2/2015 |
| EP | 2833836 | 2/2015 |
| EP | 2838475 | 2/2015 |
| EP | 2839815 | 2/2015 |
| EP | 2844190 | 3/2015 |
| EP | 2849680 | 3/2015 |
| EP | 2849681 | 3/2015 |
| EP | 2852354 | 4/2015 |
| EP | 2854719 | 4/2015 |
| EP | 2870933 | 5/2015 |
| EP | 2873011 | 5/2015 |
| EP | 2875797 | 5/2015 |
| EP | 2760375 | 6/2015 |
| EP | 2882374 | 6/2015 |
| EP | 2886082 | 6/2015 |
| EP | 2886083 | 6/2015 |
| EP | 2886084 | 6/2015 |
| EP | 2895111 | 7/2015 |
| EP | 2901966 | 8/2015 |
| EP | 2907479 | 8/2015 |
| EP | 2945572 | 11/2015 |
| EP | 2948094 | 12/2015 |
| EP | 2948102 | 12/2015 |
| EP | 2964152 | 1/2016 |
| EP | 2967859 | 1/2016 |
| EP | 2967860 | 1/2016 |
| EP | 2967866 | 1/2016 |
| EP | 2968847 | 1/2016 |
| EP | 2981208 | 2/2016 |
| EP | 2982336 | 2/2016 |
| EP | 2999433 | 3/2016 |
| EP | 3003187 | 4/2016 |
| EP | 3003219 | 4/2016 |
| EP | 3003220 | 4/2016 |
| EP | 3010447 | 4/2016 |
| EP | 3013281 | 5/2016 |
| EP | 3017792 | 5/2016 |
| EP | 3021792 | 5/2016 |
| EP | 3023117 | 5/2016 |
| EP | 3027143 | 6/2016 |
| EP | 3033048 | 6/2016 |
| EP | 3037064 | 6/2016 |
| EP | 3079633 | 10/2016 |
| EP | 3229736 | 11/2016 |
| EP | 2470119 | 5/2017 |
| EP | 2999436 | 5/2017 |
| EP | 3184081 | 6/2017 |
| EP | 3191027 | 7/2017 |
| EP | 2611389 | 8/2017 |
| EP | 3082656 | 8/2017 |
| EP | 3206628 | 8/2017 |
| EP | 2010103 | 9/2017 |
| EP | 2509538 | 9/2017 |
| EP | 3223751 | 10/2017 |
| EP | 3027144 | 11/2017 |
| EP | 3110368 | 11/2017 |
| EP | 3110369 | 11/2017 |
| EP | 3132773 | 11/2017 |
| EP | 3245980 | 11/2017 |
| EP | 3250154 | 12/2017 |
| EP | 3256074 | 12/2017 |
| EP | 3256077 | 12/2017 |
| EP | 3258883 | 12/2017 |
| EP | 3270825 | 1/2018 |
| EP | 3273910 | 1/2018 |
| JP | 6504516 | 5/1994 |
| JP | H10258124 | 9/1998 |
| JP | 2002509756 | 4/2002 |
| JP | 2005280917 | 10/2005 |
| JP | 2008528117 | 7/2008 |
| JP | 2008541863 | 11/2008 |
| JP | 2009195712 | 9/2009 |
| JP | 2010518947 | 6/2010 |
| JP | 5219518 | 6/2013 |
| WO | WO1992017118 | 10/1992 |
| WO | WO1995016407 | 6/1995 |
| WO | WO1999004730 | 2/1999 |
| WO | WO1999039648 | 8/1999 |
| WO | WO1999049799 | 10/1999 |
| WO | WO2001010343 | 2/2001 |
| WO | WO2002003892 | 1/2002 |
| WO | WO2002028421 | 4/2002 |
| WO | WO2002039908 | 5/2002 |
| WO | WO2003043685 | 5/2003 |
| WO | WO2004084746 | 10/2004 |
| WO | WO2004093728 | 11/2004 |
| WO | WO2004096097 | 11/2004 |
| WO | WO2004112657 | 12/2004 |
| WO | WO2005002466 | 1/2005 |
| WO | WO2005007219 | 1/2005 |
| WO | WO2005009285 | 2/2005 |
| WO | WO2005009506 | 2/2005 |
| WO | WO2005087140 | 9/2005 |
| WO | WO2006041877 | 4/2006 |
| WO | WO2006063199 | 6/2006 |
| WO | WO2007008371 | 1/2007 |

(56) References Cited

FOREIGN PATENT DOCUMENTS

| | | |
|---|---|---|
| WO | WO2007067820 | 6/2007 |
| WO | WO 2007098232 | 8/2007 |
| WO | WO2008022077 | 2/2008 |
| WO | WO2008028569 | 3/2008 |
| WO | WO2008035337 | 3/2008 |
| WO | WO2008103497 | 8/2008 |
| WO | WO 2008103722 | 8/2008 |
| WO | WO2008129405 | 10/2008 |
| WO | WO2009045338 | 4/2009 |
| WO | WO 2009091509 | 7/2009 |
| WO | WO2010006627 | 1/2010 |
| WO | WO2010008549 | 1/2010 |
| WO | WO2010057262 | 5/2010 |
| WO | WO2010080594 | 7/2010 |
| WO | WO2010098857 | 9/2010 |
| WO | WO2010099032 | 9/2010 |
| WO | WO2010117680 | 10/2010 |
| WO | WO 2010121076 | 10/2010 |
| WO | WO 2011025981 | 3/2011 |
| WO | WO2011047168 | 4/2011 |
| WO | WO2011051043 | 5/2011 |
| WO | WO2011057087 | 5/2011 |
| WO | WO2011072084 | 6/2011 |
| WO | WO2011106137 | 9/2011 |
| WO | WO2011106544 | 9/2011 |
| WO | WO2011111047 | 9/2011 |
| WO | WO2011137531 | 11/2011 |
| WO | WO2011139747 | 11/2011 |
| WO | WO2012011018 | 1/2012 |
| WO | WO2012011108 | 1/2012 |
| WO | WO2012027487 | 3/2012 |
| WO | WO2012035279 | 3/2012 |
| WO | WO2012040655 | 3/2012 |
| WO | WO2012047644 | 4/2012 |
| WO | WO 2012052718 | 4/2012 |
| WO | WO2012055498 | 5/2012 |
| WO | WO2012087842 | 6/2012 |
| WO | WO2012095455 | 7/2012 |
| WO | WO2012102928 | 8/2012 |
| WO | WO2012106602 | 8/2012 |
| WO | WO2012118508 | 9/2012 |
| WO | WO2012118816 | 9/2012 |
| WO | WO2012118894 | 9/2012 |
| WO | WO2012177942 | 12/2012 |
| WO | WO2013021374 | 2/2013 |
| WO | WO2013021375 | 2/2013 |
| WO | WO2013028387 | 2/2013 |
| WO | WO2013059743 | 4/2013 |
| WO | WO2013059747 | 4/2013 |
| WO | WO2013114214 | 8/2013 |
| WO | WO2013120181 | 8/2013 |
| WO | WO2013123059 | 8/2013 |
| WO | WO2013128432 | 9/2013 |
| WO | WO2013130641 | 9/2013 |
| WO | WO2013131925 | 9/2013 |
| WO | WO2013140318 | 9/2013 |
| WO | WO2013148017 | 10/2013 |
| WO | WO2013148018 | 10/2013 |
| WO | WO2013148019 | 10/2013 |
| WO | WO2013150512 | 10/2013 |
| WO | WO2013152161 | 10/2013 |
| WO | WO2013158613 | 10/2013 |
| WO | WO2013169448 | 11/2013 |
| WO | WO2013175468 | 11/2013 |
| WO | WO2013176583 | 11/2013 |
| WO | WO2013188077 | 12/2013 |
| WO | WO2013192107 | 12/2013 |
| WO | WO2014036113 | 3/2014 |
| WO | WO2014043527 | 3/2014 |
| WO | WO2014047111 | 3/2014 |
| WO | WO2014047325 | 3/2014 |
| WO | WO2014055981 | 4/2014 |
| WO | WO2014059432 | 4/2014 |
| WO | WO2014064694 | 5/2014 |
| WO | WO2014066365 | 5/2014 |
| WO | WO2014089424 | 6/2014 |
| WO | WO2014093861 | 6/2014 |
| WO | WO2014111918 | 7/2014 |
| WO | WO2014114794 | 7/2014 |
| WO | WO2014114795 | 7/2014 |
| WO | WO2014114796 | 7/2014 |
| WO | WO2014114798 | 7/2014 |
| WO | WO2014116502 | 7/2014 |
| WO | WO2014121280 | 8/2014 |
| WO | WO2014128705 | 8/2014 |
| WO | WO2014134277 | 9/2014 |
| WO | WO2014138194 | 9/2014 |
| WO | WO2014138284 | 9/2014 |
| WO | WO2014138482 | 9/2014 |
| WO | WO2014138868 | 9/2014 |
| WO | WO2014144100 | 9/2014 |
| WO | WO2014144937 | 9/2014 |
| WO | WO2014145338 | 9/2014 |
| WO | WO2014147336 | 9/2014 |
| WO | WO2014152306 | 9/2014 |
| WO | WO2014152375 | 9/2014 |
| WO | WO2014152503 | 9/2014 |
| WO | WO2014153544 | 9/2014 |
| WO | WO2014158617 | 10/2014 |
| WO | WO2014162181 | 10/2014 |
| WO | WO2014162306 | 10/2014 |
| WO | WO2014163705 | 10/2014 |
| WO | WO2014168655 | 10/2014 |
| WO | WO2014179391 | 11/2014 |
| WO | WO2014181336 | 11/2014 |
| WO | WO2014189974 | 11/2014 |
| WO | WO2014191994 | 12/2014 |
| WO | WO2014194178 | 12/2014 |
| WO | WO2014201384 | 12/2014 |
| WO | WO2014201452 | 12/2014 |
| WO | WO2014205064 | 12/2014 |
| WO | WO2014207699 | 12/2014 |
| WO | WO2014210124 | 12/2014 |
| WO | WO2014210299 | 12/2014 |
| WO | WO2015009503 | 1/2015 |
| WO | WO2015020971 | 2/2015 |
| WO | WO2015028986 | 3/2015 |
| WO | WO2015051430 | 4/2015 |
| WO | WO2015052663 | 4/2015 |
| WO | WO2015057407 | 4/2015 |
| WO | WO2015057735 | 4/2015 |
| WO | WO2015057995 | 4/2015 |
| WO | WO2015061378 | 4/2015 |
| WO | WO2015061431 | 4/2015 |
| WO | WO2015061463 | 4/2015 |
| WO | WO2015061533 | 4/2015 |
| WO | WO2015075128 | 5/2015 |
| WO | WO2015081775 | 6/2015 |
| WO | WO2015089334 | 6/2015 |
| WO | WO2015092554 | 6/2015 |
| WO | WO2015120122 | 8/2015 |
| WO | WO2015125024 | 8/2015 |
| WO | WO2015127264 | 8/2015 |
| WO | WO2015127283 | 8/2015 |
| WO | WO201 5142648 | 9/2015 |
| WO | WO2015128739 | 9/2015 |
| WO | WO2015128741 | 9/2015 |
| WO | WO2015128747 | 9/2015 |
| WO | WO2015132667 | 9/2015 |
| WO | WO2015132668 | 9/2015 |
| WO | WO2015135050 | 9/2015 |
| WO | WO2015142834 | 9/2015 |
| WO | WO2015148241 | 10/2015 |
| WO | WO2015171190 | 11/2015 |
| WO | WO2015171743 | 11/2015 |
| WO | WO 2015179181 | 11/2015 |
| WO | WO2015191604 | 12/2015 |
| WO | WO2015191839 | 12/2015 |
| WO | WO2015195823 | 12/2015 |
| WO | WO2016011185 | 1/2016 |
| WO | WO2016020918 | 2/2016 |
| WO | WO2016027272 | 2/2016 |
| WO | WO2016059533 | 4/2016 |
| WO | WO2016065158 | 4/2016 |

(56) References Cited

FOREIGN PATENT DOCUMENTS

| WO | WO2016073741 | 5/2016 |
|---|---|---|
| WO | WO2016083551 | 6/2016 |
| WO | WO2016093877 | 6/2016 |
| WO | WO2016097337 | 6/2016 |
| WO | WO2016108181 | 7/2016 |
| WO | 2016/123540 A1 | 8/2016 |
| WO | WO 2016133950 | 8/2016 |
| WO | WO 2016150806 | 9/2016 |
| WO | WO 2016201024 | 12/2016 |
| WO | WO 2016209970 | 12/2016 |
| WO | WO 2017011697 | 1/2017 |
| WO | WO 2017062640 | 4/2017 |
| WO | WO 2017087701 | 5/2017 |
| WO | WO 2017096157 | 6/2017 |
| WO | WO 2017100927 | 6/2017 |
| WO | WO 2017101232 | 6/2017 |
| WO | WO 2017117388 | 7/2017 |
| WO | WO 2017127939 | 8/2017 |
| WO | WO 2017136287 | 8/2017 |
| WO | WO 2017136596 | 8/2017 |
| WO | WO 2017165810 | 9/2017 |
| WO | WO 2017192960 | 11/2017 |
| WO | WO 2017196511 | 11/2017 |
| WO | WO 2017196909 | 11/2017 |
| WO | WO 2017196977 | 11/2017 |
| WO | WO 2017197064 | 11/2017 |
| WO | WO 2017197065 | 11/2017 |
| WO | WO 2017189040 | 12/2017 |
| WO | WO 2017218671 | 12/2017 |
| WO | WO 2018017886 | 1/2018 |
| WO | WO 2018029680 | 2/2018 |

OTHER PUBLICATIONS

International Search Report and Written Opinion dated Aug. 3, 2018 for PCT Application No. PCT/US2018035086, 15 pages.
International Search Report and Written Opinion dated Aug. 9, 2018 for PCT Application No. PCT/US2018/035081, 11 pages.
Search Report and Written Opinion dated Jul. 11, 2018 for PCT Application No. PCT/US2018/027990, 15 pages.
Search Report and Written Opinion dated Jun. 28, 2018 for PCT Application No. PCT/US2018/027983, 15 pages.
Bernard et al., "Aortic Valve Area Evolution After Percutaneous Aortic Valvuloplasty," European Heart Journal, Jul. 1990, vol. 11 (2), pp. 98-107.
BlueCross BlueShield of Northern Carolina Corporate Medical Policy "Balloon valvuloplasty, Percutaneous", (Jun. 1994).
Cimino et al., "Physics of Ultrasonic Surgery Using Tissue Fragmentation: Part I and Part II", Ultrasound in Medicine and Biology!, Jun. 1996, vol. 22 (1), pp. 89-100, and pp. 101-117.
Cimino, "Ultrasonic Surgery: Power Quantification and Efficiency Optimization", Aesthetic Surgery Journal, Feb. 2001, pp. 233-241.
Cowell et al., "A Randomized Trial of Intensive Lipid-Lowering Therapy in Calcific Aortic Stenosis," NEJM, Jun. 2005, vol. 352 (23), pp. 2389-2397.
De Korte et al., "Characterization of Plaque Components and Vulnerability with Intravascular Ultrasound Elastography", Phys. Med. Bioi., Feb. 2000, vol. 45, pp. 1465-1475.
European Search Report dated Mar. 13, 2015 for European Application. No. 05853460.3.
Feldman, "Restenosis Following Successful Balloon Valvuloplasty: Bone Formation in Aortic Valve Leaflets", Cathet Cardiovasc Diagn, May 1993, vol. 29 (1), pp. 1-7.
Fitzgerald et al., "Intravascular Sonotherapy Decreased Neointimal Hyperplasia After Stent Implantation in Swine", Circulation, Feb. 2001, vol. 103, pp. 1828-1831.
Freeman et al., "Ultrasonic Aortic Valve Decalcification: Serial Doppler Echocardiographic Follow Up", JAm Coli Cardiol., Sep. 1990, vol. 16 (3), pp. 623-630.
Greenleaf et al., "Selected Methods for Imaging Elastic Properties of Biological Tissues", Annu. Rev. Biomed. Eng., Apr. 2003, vol. 5, pp. 57-78.
Gunn et al., "New Developments in Therapeutic Ultrasound-Assisted Coronary Angioplasty", Curr IntervCardiol Rep., Dec. 1990, vol. 1 (4), pp. 281-290.
Guzman et al., "Bioeffects Caused by Changes in Acoustic Cavitation Bubble Density and Cell Concentration: A Unified Explanation Based on Cell-to-Bubble Ratio and Blast Radius", Ultrasound in Med. & Bioi., Mar. 2003, vol. 29 (8), pp. 1211-1222.
Hallgrimsson et al., "Chronic Non-Rheumatic Aortic Valvular Disease: a Population Study Based on Autopsies", J Chronic Dis., Jun. 1979, vol. 32 (5), pp. 355-363.
Isner et al., "Contrasting Histoarchitecture of Calcified Leaflets from Stenotic Bicuspid Versus Stenotic Tricuspid Aortic Valves", JAm Coli Cardiol., Apr. 1990, vol. 15 (5), p. 1104-1108.
Lung et al., "A Prospective Survey of Patients with Valvular Heart Disease in Europe: The Euro Heart Survey on Valvular Heart Disease", Euro Heart Journal, Mar. 2003, vol. 24, pp. 1231-1243.
McBride et al "Aortic Valve Decalcification", J Thorac Cardiovas-Surg, Jul. 1990, vol. 100, pp. 36-42.
Miller et al., "Lysis and Sonoporation of Epidermoid and Phagocytic Monolayer Cells by Diagnostic Ultrasound Activation of Contrast Agent Gas Bodies", Ultrasound in Med. & Bioi., May 2007, vol. 27 (8), pp. 1107-1113.
Mohler, "Mechanisms of Aortic Valve Calcificaion", Am J Cardiol, Dec. 2004, vol. 94 (11), pp. 1396-1402.
Otto et al., "Three-Year Outcome After Balloon Aortic Valvuloplasty. Insights into Prognosis of Valvular Aortic Stenosis", Circulation, Feb. 1994, vol. 89, pp. 642-650.
Passik et al., "Temporal Changes in the Causes of Aortic Stenosis: A Surgical Pathologic Study of 646 Cases", Mayo Clin Proc, Feb. 1987, vol. 62, pp. 19-123.
Quaden et al., "Percutaneous Aortic Valve Replacement: Resection Before Implantation", Eur J Cardiothorac Surg, Jan. 2005, vol. 27, pp. 836-840.
Riebman et al., "New Concepts in the Management of Patients with Aortic Valve Disease", Abstract, Valvular Heart Disease, JACC, Mar. 2004, p. 34A.
Rosenschein et al., "Percutaneous Transluminal Therapy of Occluded Saphenous Vein Grafts" Circulation, Jan. 1999, vol. 99, pp. 26-29.
Sakata et al., "Percutaneous Balloon Aortic Valvuloplasty: Antegrade Transseptal vs. Conventional Retrograde Transarterial Approach", Catheter Cardiovasc Interv., Mar. 2005, vol. 64 (3), pp. 314-321.
Sasaki et al., "Scanning Electron Microscopy and Fourier Transformed Infrared Spectroscopy Analysis of Bone Removal Using Er:YAG and C02 Lasers", J Periodontal., Jun. 2002, vol. 73 (6), pp. 643-652.
Search Report and Written Opinion dated Dec. 10, 2012 for PCT Application No. PCT/US2012/043636.
Search Report and Written Opinion dated Dec. 6, 2016 for PCT Application No. PCT/US2016/04 7831.
Search Report and Written Opinion dated Apr. 19, 2014 PCT Application No. PCT/US2012/061215.
Search Report and Written Opinion dated Apr. 19, 2014 PCT Application No. PCT/US2012/061219.
Search Report and Written Opinion dated Mar. 2, 2015 for PCT Application No. PCT/US2014/029549.
Search Report and Written Opinion dated May 1, 2012 for PCT Application No. PCT/US2011/065627.
Search Report and Written Opinion dated May 22, 2007 for PCT Application No. PCT/US2005/044543.
Search Report and Written Opinion dated Oct. 20, 2014 for PCT Application No. PCT/US2014/038849.
Search Report and Written Opinion dated Sep. 4, 2014 for PCT Application No. PCT/US2014/014 704.
The CoreValve System Medtronic, 2012, 4 Pages.
Van Den Brand et al., "Histological Changes in the Aortic Valve after Balloon Dilation: Evidence for a Delayed Healing Process", Br Heart J, Jun. 1992, vol. 67, pp. 445-459.
Verdaadadonk et al., "The Mechanism of Action of the Ultrasonic Tissue Resectors Disclosed Using High-Speed and Thermal Imaging Techniques", SPIE, Jan. 1999, vol. 3594, pp. 221-231.

(56) References Cited

OTHER PUBLICATIONS

Voelker et al., "Inoperative Valvuloplasty in Calcific Aortic Stenosis: a Study Comparing the Mechanism of a Novel Expandable Device with Conventional Balloon Dilation", Am Heart J., Nov. 1991, vol. 122 (5), pp. 1327-1333.
Waller et al., "Catheter Balloon Valvuloplasty of Stenotic Aortic Valves. Part II: Balloon Valvuloplasty During Life Subsequent Tissue Examination", Clin Cardiol., Nov. 1991, vol. 14 (11), pp. 924-930.
Wang, "Balloon Aortic Valvuloplasty", Prog Cardiovasc Dis., Jul.-Aug. 1997, vol. 40 (1), pp. 27-36.
Wilson et al., "Elastography—The movement Begins", Phys. Med. Biol., Jun. 2000, vol. 45, pp. 1409-1421.
Yock et al., "Catheter-Based Ultrasound Thrombolysis", Circulation, Mar. 1997, vol. 95 (6), pp. 1411-1416.
Prosecution History from U.S. Appl. No. 15/490,024, dated Jan. 31, 2019-Aug. 27, 2019, 41 pp.
Notice of First Office Action, China Application No. 201880024834. 2, dated Apr. 6, 2021.

Background

Background

Background

Background

Background

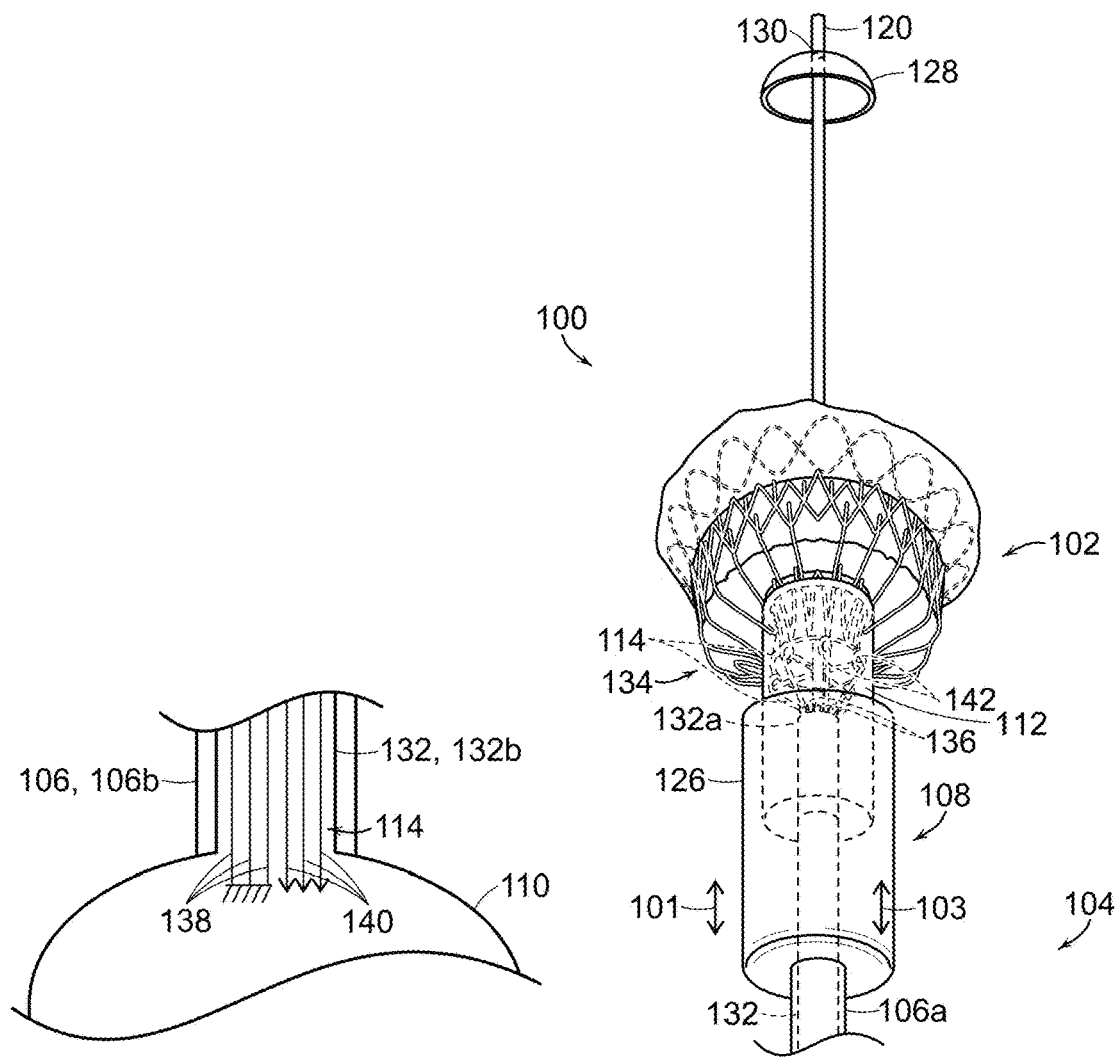
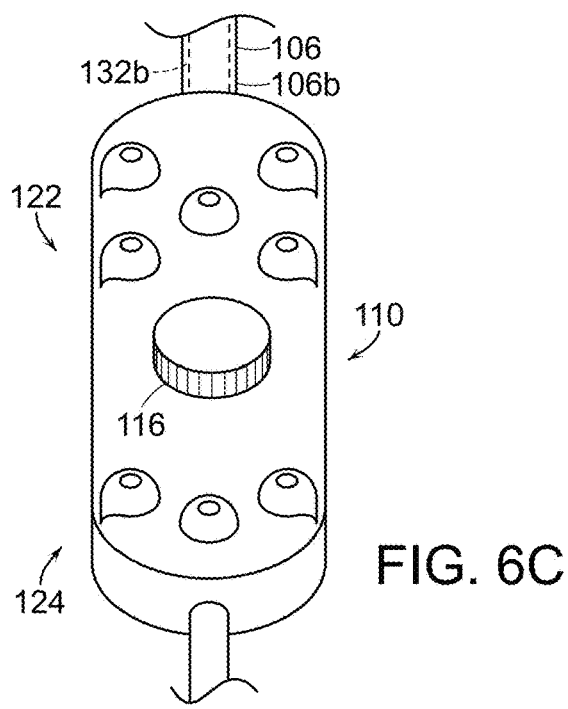
FIG. 6B
FIG. 6C

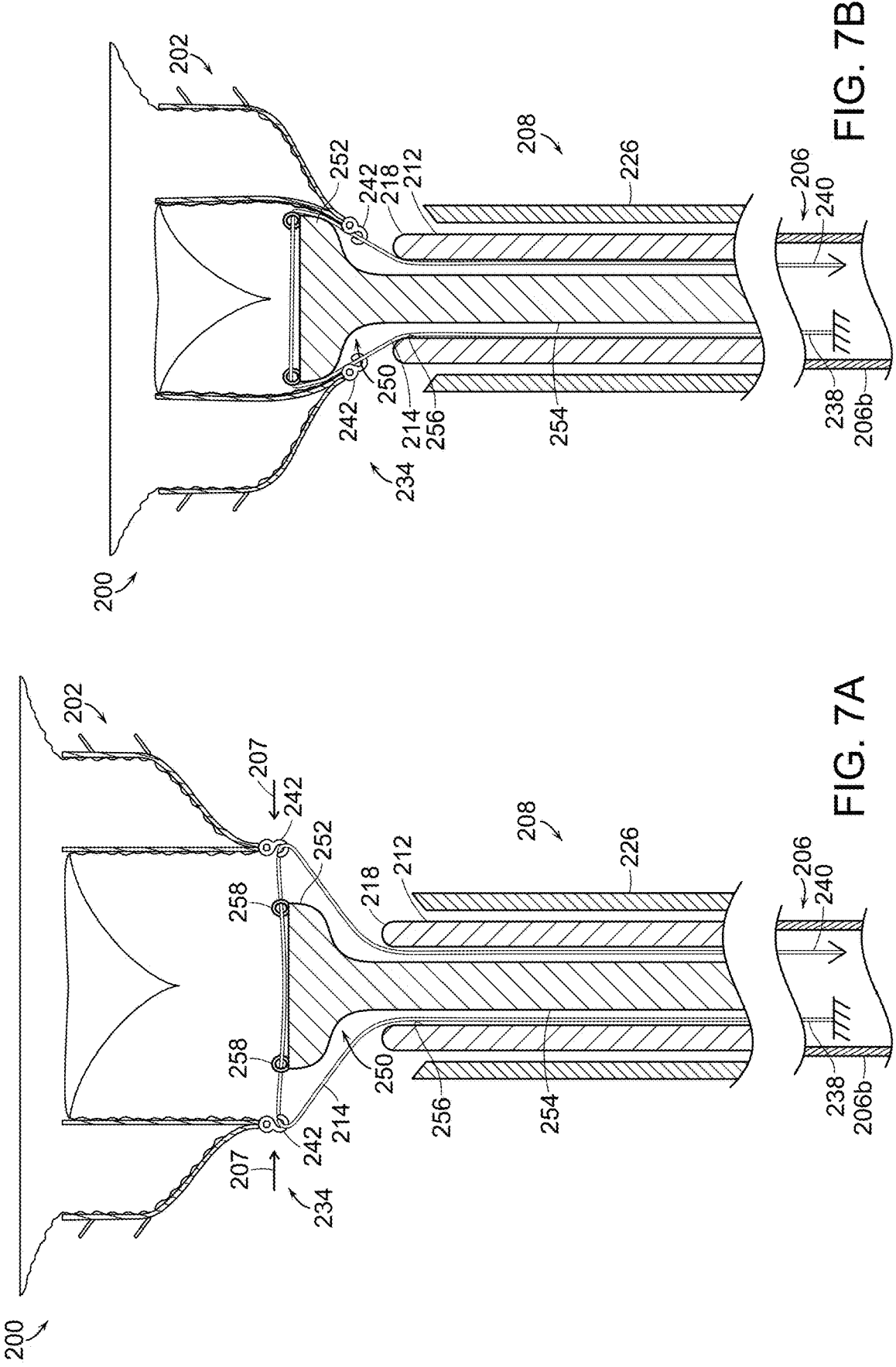

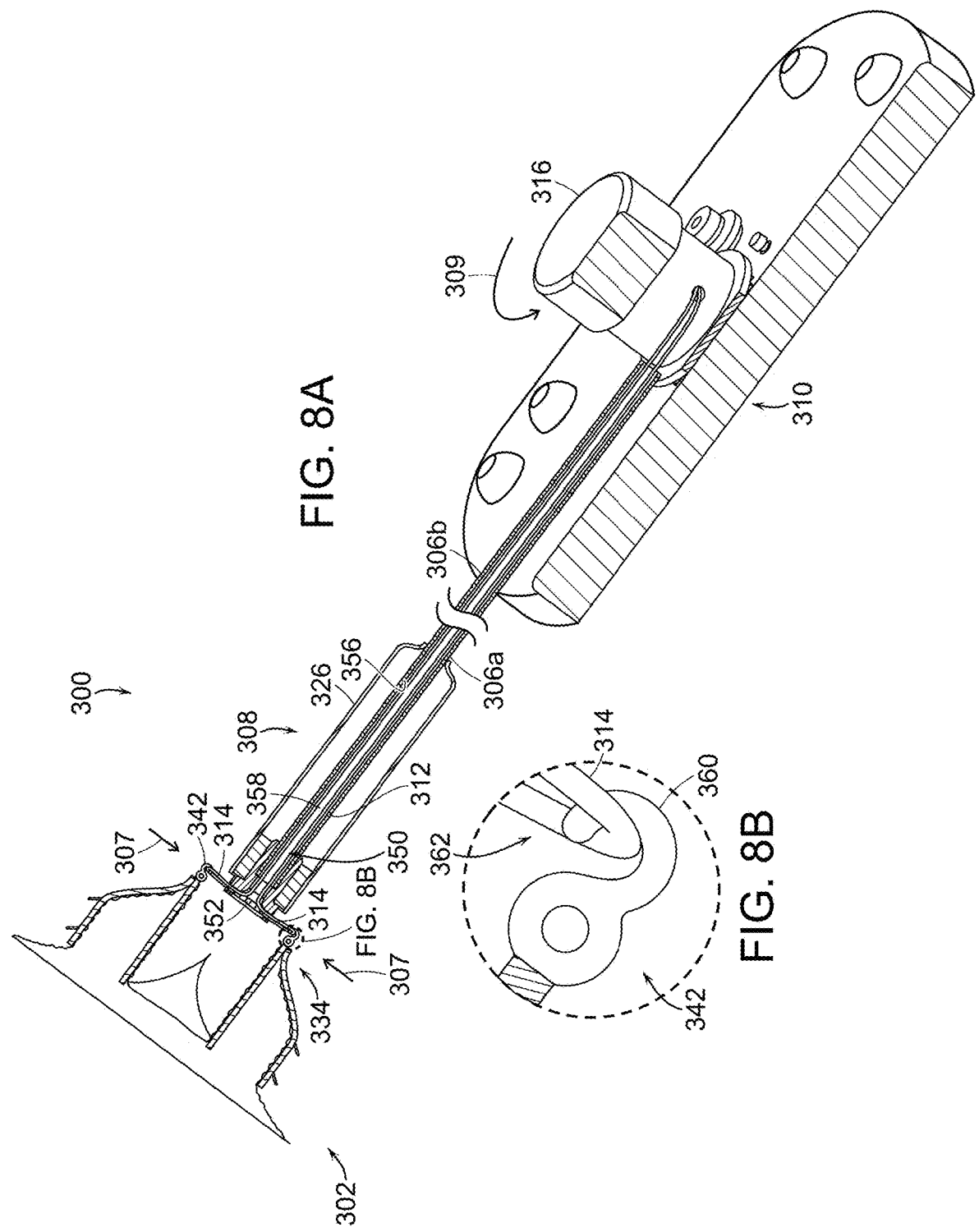

DELIVERY SYSTEMS WITH TETHERS FOR PROSTHETIC HEART VALVE DEVICES AND ASSOCIATED METHODS

CROSS-REFERENCE TO RELATED APPLICATIONS

This application is a divisional of U.S. patent application Ser. No. 15/490,024 filed on Apr. 18, 2017, which is incorporated herein by reference in its entirety. The present application incorporates the subject matter of (1) International Patent Application No. PCT/US2014/029549, filed Mar. 14, 2014, (2) International Patent Application No. PCT/US2012/061219, filed Oct. 19, 2012, (3) International Patent Application No. PCT/US2012/061215, filed Oct. 19, 2012, (4) International Patent Application No. PCT/US2012/043636, filed Jun. 21, 2012. The present application also incorporates the subject matter of U.S. application Ser. No. 15/490,008, filed concurrently herewith.

TECHNICAL FIELD

The present technology relates generally to systems for delivering prosthetic heart valve devices. In particular, several embodiments of the present technology are related to delivery systems with tethers for percutaneously delivering prosthetic heart valve devices into heart valves and associated methods.

BACKGROUND

Heart valves can be affected by several conditions. For example, mitral valves can be affected by mitral valve regurgitation, mitral valve prolapse and mitral valve stenosis. Mitral valve regurgitation is abnormal leaking of blood from the left ventricle into the left atrium caused by a disorder of the heart in which the leaflets of the mitral valve fail to coapt into apposition at peak contraction pressures. The mitral valve leaflets may not coapt sufficiently because heart diseases often cause dilation of the heart muscle, which in turn enlarges the native mitral valve annulus to the extent that the leaflets do not coapt during systole. Abnormal backflow can also occur when the papillary muscles are functionally compromised due to ischemia or other conditions. More specifically, as the left ventricle contracts during systole, the affected papillary muscles do not contract sufficiently to effect proper closure of the leaflets.

Mitral valve prolapse is a condition when the mitral leaflets bulge abnormally up in to the left atrium. This can cause irregular behavior of the mitral valve and lead to mitral valve regurgitation. The leaflets mail prolapse and fail to coapt because the tendons connecting the papillary muscles to the inferior side of the mitral valve leaflets (chordae tendineae) may tear or stretch. Mitral valve stenosis is a narrowing of the mitral valve orifice that impedes filling of the left ventricle in diastole.

Mitral valve regurgitation is often treated using diuretics and/or vasodilators to reduce the amount of blood flowing back into the left atrium. Surgical approaches (open and intravascular) for either the repair or replacement of the valve have also been used to treat mitral valve regurgitation. For example, typical repair techniques involve cinching or resecting portions of the dilated annulus. Cinching, for example, includes implanting annular or peri-annular rings that are generally secured to the annulus or surrounding tissue. Other repair procedures suture or clip the valve leaflets into partial apposition with one another.

Alternatively, more invasive procedures replace the entire valve itself by implanting mechanical valves or biological tissue into the heart in place of the native mitral valve. These invasive procedures conventionally require large open thoracotomies and are thus very painful, have significant morbidity, and require long recovery periods. Moreover, with many repair and replacement procedures, the durability of the devices or improper sizing of annuloplasty rings or replacement valves may cause additional problems for the patient. Repair procedures also require a highly skilled cardiac surgeon because poorly or inaccurately placed sutures may affect the success of procedures.

Less invasive approaches to aortic valve replacement have been implemented in recent years. Examples of pre-assembled, percutaneous prosthetic valves include, e.g., the CoreValve Revalving® System from Medtronic/Corevalve Inc. (Irvine, Calif., USA) and the Edwards-Sapien® Valve from Edwards Lifesciences (Irvine, Calif., USA). Both valve systems include an expandable frame and a tri-leaflet bioprosthetic valve attached to the expandable frame. The aortic valve is substantially symmetric, circular, and has a muscular annulus. The expandable frames in aortic applications have a symmetric, circular shape at the aortic valve annulus to match the native anatomy, but also because tri-leaflet prosthetic valves require circular symmetry for proper coaptation of the prosthetic leaflets. Thus, aortic valve anatomy lends itself to an expandable frame housing a replacement valve since the aortic valve anatomy is substantially uniform, symmetric, and fairly muscular. Other heart valve anatomies, however, are not uniform, symmetric or sufficiently muscular, and thus transvascular aortic valve replacement devises may not be well suited for other types of heart valves.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. The headings provided herein are for convenience only.

FIG. 6B is a partially schematic side view of a proximal portion of the delivery system of FIG. 6A.

FIG. 6C is a side isometric view of the delivery system of FIG. 6A with the prosthetic heart valve device in a partially retracted state.

FIG. 7A is a side cross-sectional view of a delivery system with a prosthetic heart valve device in an expanded state in accordance with another embodiment of the present technology.

FIG. 7B is a side isometric view of the delivery system of FIG. 7A with the prosthetic heart valve device in a partially contracted state.

FIG. 8A is a partial cross-sectional isometric view of a delivery system with a prosthetic heart valve device in an expanded state in accordance with yet another embodiment of the present technology.

FIG. 8B is an enlarged side view of a tether element connection site of the delivery system of FIG. 8A.

DETAILED DESCRIPTION

Figure 1:
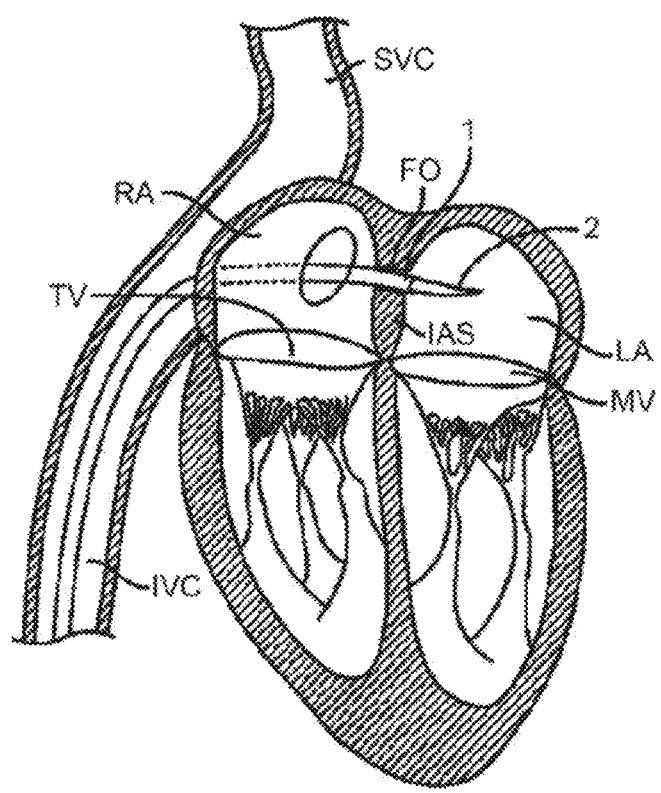
FIG. 1 is a schematic, cross-sectional illustration of the heart showing an antegrade approach to the native mitral valve from the venous vasculature in accordance with various embodiments of the present technology.

The present technology is generally directed to delivery systems with tethering features for prosthetic heart valve devices and associated methods. Specific details of several embodiments of the present technology are described herein with reference to FIGS. 1-24. Although many of the embodiments are described with respect to devices, systems, and methods for delivering prosthetic heart valve devices to a native mitral valve, other applications and other embodiments in addition to those described herein are within the scope of the present technology. For example, at least some embodiments of the present technology may be useful for delivering prosthetics to other valves, such as the tricuspid valve or the aortic valve. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

With regard to the terms "distal" and "proximal" within this description, unless otherwise specified, the terms can reference relative positions of portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a location where blood flows into the device (e.g., inflow region), and distal can refer to a downstream position or a location where blood flows out of the device (e.g., outflow region).

Overview

Several embodiments of the present technology are directed to delivery systems and mitral valve replacement devices that address the unique challenges of percutaneously replacing native mitral valves and are well-suited to be recaptured in a percutaneous delivery device after being partially deployed for repositioning or removing the device. Compared to replacing aortic valves, percutaneous mitral valve replacement faces unique anatomical obstacles that render percutaneous mitral valve replacement significantly more challenging than aortic valve replacement. First, unlike relatively symmetric and uniform aortic valves, the mitral valve annulus has a non-circular D-shape or kidney-like shape, with a non-planar, saddle-like geometry often lacking symmetry. The complex and highly variable anatomy of mitral valves makes it difficult to design a mitral valve prosthesis that conforms well to the native mitral annulus of specific patients. As a result, the prosthesis may not fit well with the native leaflets and/or annulus, which can leave gaps that allows backflow of blood to occur. For example, placement of a cylindrical valve prosthesis in a native mitral valve may leave gaps in commissural regions of the native valve through which perivalvular leaks may occur.

Current prosthetic valves developed for percutaneous aortic valve replacement are unsuitable for use in mitral valves. First, many of these devices require a direct, structural connection between the stent-like structure that contacts the annulus and/or leaflets and the prosthetic valve. In several devices, the stent posts which support the prosthetic valve also contact the annulus or other surrounding tissue.

These types of devices directly transfer the forces exerted by the tissue and blood as the heart contracts to the valve support and the prosthetic leaflets, which in turn distorts the valve support from its desired cylindrical shape. This is a concern because most cardiac replacement devices use tri-leaflet valves, which require a substantially symmetric, cylindrical support around the prosthetic valve for proper opening and closing of the three leaflets over years of life. As a result, when these devices are subject to movement and forces from the annulus and other surrounding tissues, the prostheses may be compressed and/or distorted causing the prosthetic leaflets to malfunction. Moreover, a diseased mitral annulus is much larger than any available prosthetic aortic valve. As the size of the valve increases, the forces on the valve leaflets increase dramatically, so simply increasing the size of an aortic prosthesis to the size of a dilated mitral valve annulus would require dramatically thicker, taller leaflets, and might not be feasible.

In addition to its irregular, complex shape, which changes size over the course of each heartbeat, the mitral valve annulus lacks a significant amount of radial support from surrounding tissue. Compared to aortic valves, which are completely surrounded by fibro-elastic tissue that provides sufficient support for anchoring a prosthetic valve, mitral valves are bound by muscular tissue on the outer wall only. The inner wall of the mitral valve anatomy is bound by a thin vessel wall separating the mitral valve annulus from the inferior portion of the aortic outflow tract. As a result, significant radial forces on the mitral annulus, such as those imparted by an expanding stent prostheses, could lead to collapse of the inferior portion of the aortic tract. Moreover, larger prostheses exert more force and expand to larger dimensions, which exacerbates this problem for mitral valve replacement applications.

The chordae tendineae of the left ventricle may also present an obstacle in deploying a mitral valve prosthesis. Unlike aortic valves, mitral valves have a maze of cordage under the leaflets in the left ventricle that restrict the movement and position of a deployment catheter and the replacement device during implantation. As a result, deploying, positioning and anchoring a valve replacement device on the ventricular side of the native mitral valve annulus is complicated.

Embodiments of the present technology provide systems, methods and apparatus to treat heart valves of the body, such as the mitral valve, that address the challenges associated with the anatomy of the mitral valve and provide for repositioning and removal of a partially deployed device. The apparatus and methods enable a percutaneous approach using a catheter delivered intravascularly through a vein or artery into the heart, or through a cannula inserted through the heart wall. For example, the apparatus and methods are particularly well-suited for trans-septal and trans-apical approaches, but can also be trans-atrial and direct aortic delivery of a prosthetic replacement valve to a target location in the heart. Additionally, the embodiments of the devices and methods as described herein can be combined with many known surgeries and procedures, such as known methods of accessing the valves of the heart (e.g., the mitral valve or triscuspid valve) with antegrade or retrograde approaches, and combinations thereof.

The systems and methods described herein facilitate resheathing of a prosthetic heart valve device after partial or full deployment of the heart valve device. The disclosed delivery systems include tether elements that are releasably attached to the heart valve device and retracted to facilitate resheathing of the device. For example, the retraction of the tether elements can at least partially collapse a ventricular portion of the heart valve device, and an open end of a delivery capsule can receive the cinched end to initiate resheathing. In certain embodiments, the partially collapsed portion of the heart valve device can be received in a cinching member that projects from the delivery capsule and further facilitates contraction of the ventricular portion of the heart valve device. This partial or full resheathing of the heart valve device allows clinicians to reposition the device, in vivo, or remove the device after partial or full deployment of the device.

Access to the Mitral Valve

To better understand the structure and operation of valve replacement devices in accordance with the present technology, it is helpful to first understand approaches for implanting the devices. The mitral valve or other type of atrioventricular valve can be accessed through the patient's vasculature in a percutaneous manner. By percutaneous it is meant that a location of the vasculature remote from the heart is accessed through the skin, typically using a surgical cut down procedure or a minimally invasive procedure, such as using needle access through, for example, the Seldinger technique. The ability to percutaneously access the remote vasculature is well known and described in the patent and medical literature. Depending on the point of vascular access, access to the mitral valve may be antegrade and may rely on entry into the left atrium by crossing the inter-atrial septum (e.g., a trans-septal approach). Alternatively, access to the mitral valve can be retrograde where the left ventricle is entered through the aortic valve. Access to the mitral valve may also be achieved using a cannula via a trans-apical approach. Depending on the approach, the interventional tools and supporting catheter(s) may be advanced to the heart intravascularly and positioned adjacent the target cardiac valve in a variety of manners, as described herein.

FIG. 1 illustrates a stage of a trans-septal approach for implanting a valve replacement device. In a trans-septal approach, access is via the inferior vena cava IVC or superior vena cava SVC, through the right atrium RA, across the inter-atrial septum IAS, and into the left atrium LA above the mitral valve MV. As shown in FIG. 1, a catheter 1 having a needle 2 moves from the inferior vena cava IVC into the right atrium RA. Once the catheter 1 reaches the anterior side of the inter-atrial septum IAS, the needle 2 advances so that it penetrates through the septum, for example at the fossa ovalis FO or the foramen ovale into the left atrium LA. At this point, a guidewire replaces the needle 2 and the catheter 1 is withdrawn.

Figure 2:
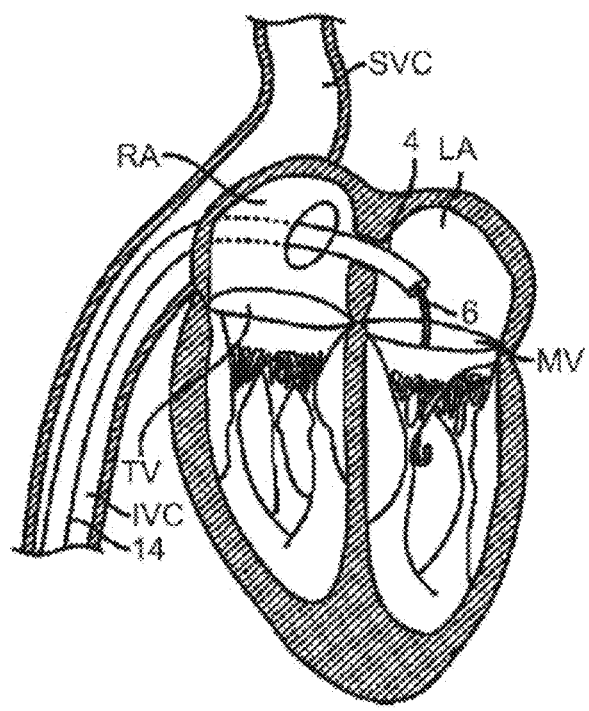
FIG. 2 is a schematic, cross-sectional illustration of the heart showing access through the inter-atrial septum (IAS) maintained by the placement of a guide catheter over a guidewire in accordance with various embodiments of the present technology.

FIG. 2 illustrates a subsequent stage of a trans-septal approach in which guidewire 6 and guide catheter 4 pass through the inter-atrial septum IAS. The guide catheter 4 provides access to the mitral valve for implanting a valve replacement device in accordance with the technology.

In an alternative antegrade approach (not shown), surgical access may be obtained through an intercostal incision, preferably without removing ribs, and a small puncture or incision may be made in the left atrial wall. A guide catheter passes through this puncture or incision directly into the left atrium, sealed by a purse string-suture.

The antegrade or trans-septal approach to the mitral valve, as described above, can be advantageous in many respects. For example, antegrade approaches will usually enable more precise and effective centering and stabilization of the guide catheter and/or prosthetic valve device. The antegrade approach may also reduce the risk of damaging the chordae tendinae or other subvalvular structures with a catheter or other interventional tool. Additionally, the antegrade approach may decrease risks associated with crossing the aortic valve as in retrograde approaches. This can be particularly relevant to patients with prosthetic aortic valves, which cannot be crossed at all or without substantial risk of damage.

Figure 3:
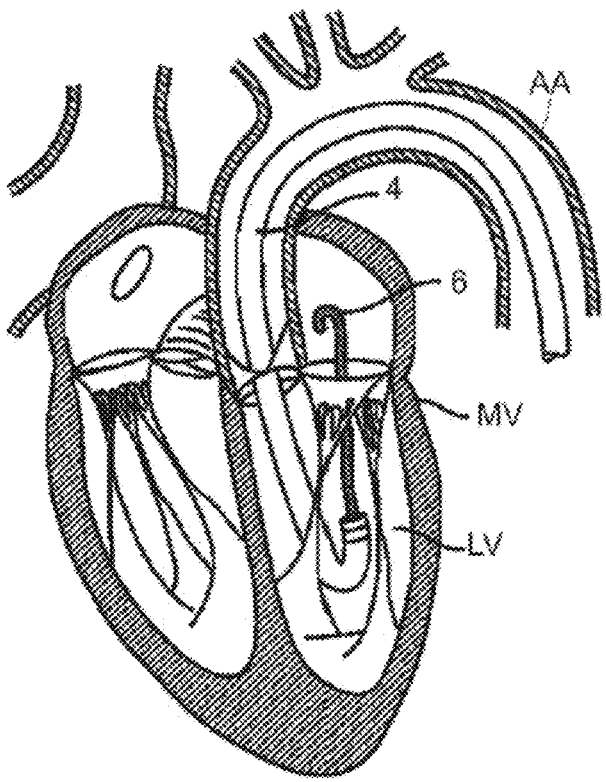
FIGS. 3 and 4 are schematic, cross-sectional illustrations of the heart showing retrograde approaches to the native mitral valve through the aortic valve and arterial vasculature in accordance with various embodiments of the present technology.
Figure 4:
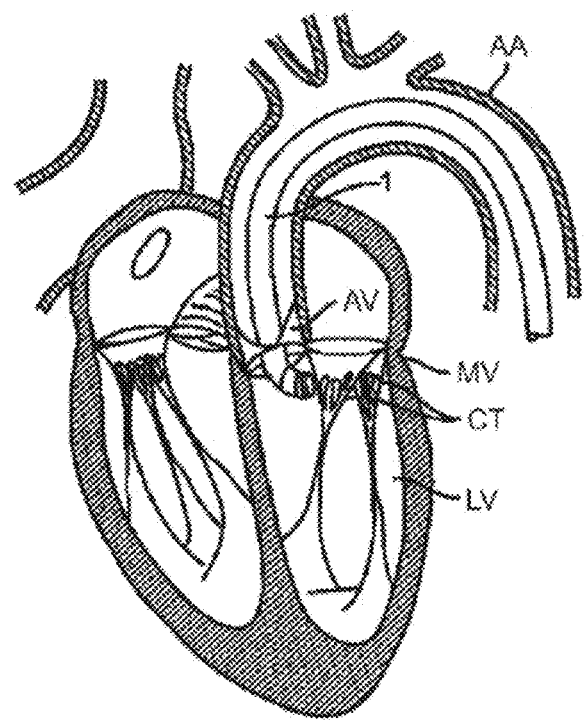

FIGS. 3 and 4 show examples of a retrograde approaches to access the mitral valve. Access to the mitral valve MV may be achieved from the aortic arch AA, across the aortic valve AV, and into the left ventricle LV below the mitral valve MV. The aortic arch AA may be accessed through a conventional femoral artery access route or through more direct approaches via the brachial artery, axillary artery, radial artery, or carotid artery. Such access may be achieved with the use of a guidewire 6. Once in place, a guide catheter 4 may be tracked over the guidewire 6. Alternatively, a surgical approach may be taken through an incision in the chest, preferably intercostally without removing ribs, and placing a guide catheter through a puncture in the aorta itself. The guide catheter 4 affords subsequent access to permit placement of the prosthetic valve device, as described in more detail herein. Retrograde approaches advantageously do not need a trans-septal puncture. Cardiologists also more commonly use retrograde approaches, and thus retrograde approaches are more familiar.

Figure 5:
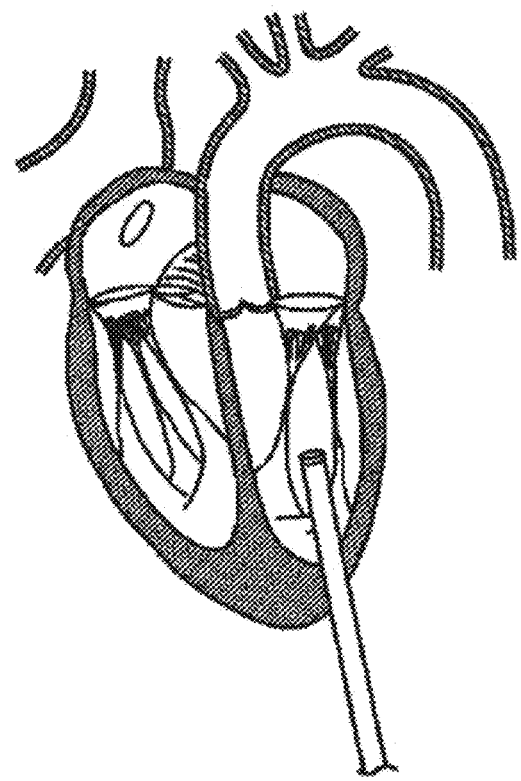
FIG. 5 is a schematic, cross-sectional illustration of the heart showing an approach to the native mitral valve using a trans-apical puncture in accordance with various embodiments of the present technology.

FIG. 5 shows a trans-apical approach via a trans-apical puncture. In this approach, access to the heart is via a thoracic incision, which can be a conventional open thoracotomy or sternotomy, or a smaller intercostal or subxyphoid incision or puncture. An access cannula is then placed through a puncture in the wall of the left ventricle at or near the apex of the heart. The catheters and prosthetic devices of the invention may then be introduced into the left ventricle through this access cannula. The trans-apical approach provides a shorter, straighter, and more direct path to the mitral or aortic valve. Further, because it does not involve intravascular access, the trans-apical approach does not require training in interventional cardiology to perform the catheterizations required in other percutaneous approaches.

Selected Embodiments of Delivery Systems for Prosthetic Heart Valve Devices

Figure 6A:
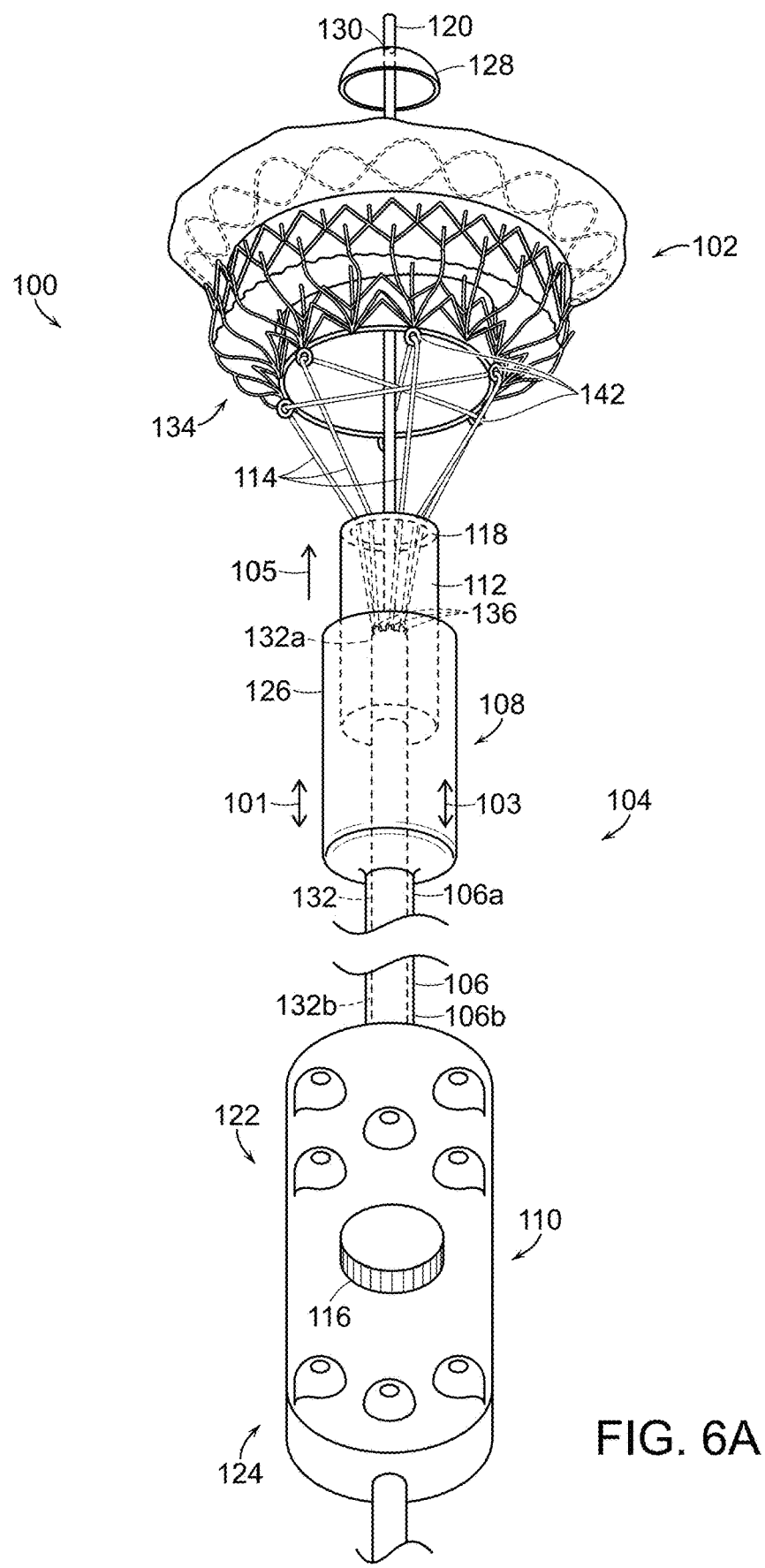
FIG. 6A is a side isometric view of a delivery system with a prosthetic heart valve device in an expanded state in accordance with an embodiment of the present technology.

FIG. 6A is a side isometric view of a delivery system 100 with a prosthetic heart valve device 102 ("device 102") in an expanded state in accordance with an embodiment of the present technology; FIG. 6B is a partially schematic side view of a proximal portion of the delivery system 100; and FIG. 6C is a side isometric view of the delivery system 100 with the device 102 in a partially retracted state. The delivery system 100 includes a catheter 104 having an elongated catheter body 106 ("catheter body 106") with a distal portion 106a carrying a delivery capsule 108 ("capsule 108") and a proximal portion 106b coupled to a control unit or handle assembly 110. The capsule 108 can move between a containment configuration for holding the device 102 in an unexpanded state during delivery of the device 102 and a deployment configuration in which the device 102 is at least partially expanded from the capsule 108. The delivery system 100 further includes a cinching member 112 slidably disposed within at least a distal portion of the capsule 108 and a plurality of tether elements 114 that are releasably coupled to the device 102. The tether elements 114 can be wires, sutures, or cables that extend through the cinching member 112 and through the catheter body 106 to the proximal portion 106b of the catheter body 106. At the proximal portion 106b, the tether elements 114 operably couple to an actuator 116 of the handle assembly 110 that can be manipulated to retract the tether elements 114 proximally or release the tether elements 114 distally.

In certain embodiments, the catheter 104 can be configured to travel over a guidewire 120, which can be used to guide the capsule 108 into a native heart valve. After the device 102 has been deployed (e.g., as shown in FIG. 6A), proximal retraction of the tether elements 114 (e.g., via the actuator 116 of the handle assembly 110) reduces the diameter of a a proximal or ventricular end portion 134 of the device 102 and urges the device 102 and a distal end portion 118 of the cinching member 112 closer together axially to facilitate resheathing at least a portion of the device 102. The partial or full resheathing of the device 102 allows for repositioning of the device 102 relative to the native heart valve (e.g., a native mitral valve) after a portion of the device 102 has contacted tissue of the native valve. As shown in FIG. 6C, in certain embodiments proximal retraction of the tether elements 114 pulls the ventricular end portion 134 of the device 102 into the distal end portion 118 of the cinching member 112 such that the end of the device 102 is covered as the capsule is advanced distally for resheathing.

The handle assembly 110 can provide steering capability (e.g., 360 degree rotation of the delivery capsule 108, 180 degree rotation of the delivery capsule 108, 3-axis steering, 2-axis steering, etc.) for delivering the capsule 108 to a target site (e.g., to a native mitral valve). The handle assembly 110 can also have additional features to initiate deployment of the device 102 at the target site. For example, the handle assembly 110 can include a control assembly 122 and a steering mechanism 124. The control assembly 122 can include rotational elements, such as a knob, that can be rotated to rotate the capsule 108 about its longitudinal axis. The control assembly 122 can also include buttons, levers, and/or other actuators that allow a clinician to control the deployment and/or resheathing mechanisms of the delivery system 100. For example, the illustrated control assembly 122 includes the actuator 116, which can be rotated in a first direction to pull the tether elements 114 proximally to at least partially resheathe the device 102 and rotated in an opposite direction to relax the tether elements 114 to allow for redeployment of the device 102. In other embodiments, the actuator 116 can be manipulated in a different manner (e.g., pulling) to pull and relax the tether elements 114. The actuator 116 can be operably coupled to twisting or pulling mechanisms that interact with the tether elements 114 to provide for the controlled movement of the tether elements 114. The steering mechanism 124 can be used to steer the catheter 104 through the anatomy by bending the distal portion 106a of the catheter body 106 about a transverse axis. In other embodiments, the handle assembly 110 may include additional and/or different features that facilitate delivering the device 102 to the target site.

The capsule 108 at the distal end portion 106a of the catheter body 106 includes a housing 126 configured to carry the device 102 and, optionally, an end cap 128 extending distally from the housing 126. As shown in FIG. 6A, the end cap 128 can include an opening 130 at its distal end through which the guidewire 120 can be threaded to allow for guidewire delivery to the target site. The end cap 128 can also have an atraumatic shape (e.g., a partially spherical shape, a frusto-conical shape, blunt configuration, rounded configuration, etc.) to facilitate atraumatic delivery of the capsule 108 to the target site. In certain embodiments, only the housing 126 carries the device 102 (e.g., the device is contained completely within just the housing 126), while in other embodiments the end cap 128 can have proximal sidewalls such that a portion of the device 102 is contained within the end cap 128. The housing 126 and/or the end cap 128 can be made of metal, polymers, plastic, composites, combinations thereof, or other materials capable of holding the device 102. As discussed in further detail below, manipulating the handle assembly 110 pulls the capsule 108 in a proximal direction to move the capsule 108 from the containment configuration to the deployment configuration and expand the device 102 from the capsule 108. In certain embodiments, manipulating the handle assembly 110 drives the end cap 128 in a distal direction to open the capsule 108. In other embodiments, the end cap 128 can be omitted and the capsule 108 can include a proximal housing and a distal housing, which both enclose portions of the device 102 in the containment configuration. During deployment, the proximal and distal housings can move proximally and distally in a simultaneous or sequential manner to deploy the device 102 from the capsule 108.

As shown in FIG. 6A, the delivery system 100 can further include a push rod 132 that extends through the catheter body 106 and is used to deploy the device 102 from the capsule 108. The push rod 132 has a distal end portion 132a (e.g., a platform) positioned proximate to a ventricular end portion 134 of the device 102 and a proximal end portion 132b coupled to the handle assembly 110. The push rod 132 can be made of metal, polymers, plastic, composites, combinations thereof, or other materials with the flexibility necessary to navigate through the anatomy to the target site and sufficient rigidity to support the device 102 during delivery. In certain embodiments, the distal end portion 132a may have a different flexibility than the proximal end portion 132b.

As indicated by the arrows 101 and 103 of FIGS. 6A and 6C, the push rod 132 and the capsule 108 can move relative to each other to initiate deployment of the device 102 from the capsule 108. For example, the proximal end portion 132b of the push rod 132 can be fixed relative to the handle assembly 110 such that distal movement of the handle assembly 110 drives the push rod 132 distally, causing the distal end portion 132a of the push rod 132 to press against the ventricular end portion 134 of the device 102 and eject at least a portion of the device 102 from the capsule 108. In other embodiments, the proximal portion 132b of the push rod 132 slides with respect to the handle assembly 110 such that the handle assembly 110 can pull the capsule 108 proximally, while the distal end portion 132a of the push rod 132 holds the device 102 in a substantially constant position relative to the longitudinal axis of the catheter body 106 for unsheathing the device 102. In further embodiments, the delivery system 100 can include other mechanisms for deploying the device 102 from the capsule 108.

In the embodiment illustrated in FIGS. 6A and 6C, the cinching member 112 is a tubular structure fixedly coupled to the distal end portion 132a of the push rod 132 and axially movable with respect to the capsule 108. Thus, movement of the push rod 132 (e.g., via the handle assembly 110 fixedly attached thereto) also moves the cinching member 112. The cinching member 112 and the distal end portion 132a of the push rod 132 can be housed in the capsule 108 or the distal portion 106a of the catheter body 106. Accordingly, the cinching member 112 has a diameter or outer dimension that is less than the diameter or inner dimension of the capsule 108 or, if housed in the catheter body 106, less than the diameter or inner dimension of the distal portion 106a of the catheter body 106. The cinching member 112 can be made from similar materials as the push rod 132, such as metals, polymers, and/or other materials with sufficient rigidity to allow a portion of the device 102 to contract into the distal end portion 118 of the cinching member 112. The cinching member 112 can be attached to the push rod 132 via welding, gluing, and/or other attachment methods. In other embodiments, the cinching member 112 can be integrally formed as an extension of the push rod 132. In further embodiments, the cinching member 112 and the push rod 132 can be separate elements extending alongside each other along the length of the catheter body 106. In this embodiment, the cinching member 112 and the push rod 132 can be fixedly attached to each other such that proximal and distal movement of the cinching member 112 or the push rod 132 imparts movement on the other of the cinching member or the push rod 132. Alternatively, the push rod 132 and the cinching member 112 may be configured to move independently of each other, and in such an embodiment the push rod 132 and the cinching member 112 can be arrange coaxially with each other or side-by-side along the length of the catheter body 106.

The cinching member 112 can be used to facilitate resheathing of the device 102 after partial or full deployment of the device 102. For example, after the device 102 has been deployed from the capsule 108, the clinician can move the push rod 132 in a distal direction until the distal end portion 118 of the cinching member 112 is exposed from the distal end of the capsule 108 (e.g., as shown in FIG. 6A). As explained in further detail below, this distal movement of the cinching member 112 constrains distal portions of the tether elements 114 within the inner diameter of the cinching member 112, which can cause the ventricular end portion 134 of the device 102 to partially collapse or be constrained in the distal end portion 118 of the cinching member 112.

The tether elements 114 are releasably coupled to the ventricular end portion 134 of the device 102 via a plurality of attachment features 142. As shown in FIGS. 6A and 6C, the attachment features 142 can be loops or eyelets spaced around the perimeter of the device 102. In the illustrated embodiment, the device 102 includes six attachment features 142 and three tether elements 114 attached thereto. Each tether element 114 is threaded through a first loop and through a second loop spaced circumferentially apart from the first loop on the ventricular end portion 134 of the device 102 such that each tether element 114 extends across a portion (e.g., a diameter or a chord) of the device 102. In other embodiments, each tether element 114 can attached to only one attachment feature 142 or connect to more than two attachment features 142. In further embodiments, the attachment features 142 can have different configurations, such as hooks or clasps that releasably attach the tether elements 114 to the device 102. In still further embodiments, the delivery system 100 includes different quantities of attachment features 142 and/or tether elements 114.

The tether elements 114 extend through the catheter body 106 to the proximal portion 106b of the catheter body 106 where they are operably coupled to the actuator 116 of the handle assembly 110. In the illustrated embodiment, the tether elements 114 extend through the cinching member 112 and into the push rod 132 to the proximal end portion 106b of the catheter body 106. As shown in FIG. 6A, the distal end portion 132a of the push rod 132 can include guide structures 136, such as eyelets, channels, or loops, that route the tether elements 114 into an opening of the push rod 132 and space the tether elements 114 apart from each other about the perimeter of the distal end of the push rod 132. In other embodiments, the push rod 132 and/or the cinching member 112 can include additional guide structures 136 that route the tether elements 114 along the length of push rod 132 and/or the cinching member 112. In further embodiments, the tether elements 114 may extend alongside the exterior of the push rod 132 rather than through the push rod 132. In this embodiment, the cinching member 112 may have openings through which the tether elements extend outside of the push rod 132 or the cinching member 112 may be a separate tubular structure around the push rod 132 that contains the tether elements 114.

Referring to FIG. 6B, each tether element 114 has a first end 138 fixed at the handle assembly 110 and a movable second end 140 that can be pulled proximally and relaxed to collapse or re-expand the device 102. The individual tether elements 114 extend from the fixed first ends 138, through the catheter body 106, to the device 102 where they are releasably coupled thereto, and extend back through the catheter body 106 to the movable second ends 140. The second ends 140 of the tether elements 114 can be operably coupled to the actuator 116 (FIG. 6A) and the actuator can be manipulated in one manner (e.g., pulled or rotated in a first direction) to tighten and proximally retract the tether elements 114 and can be manipulated in another manner (e.g., pushed or rotated in a second direction) to relax and distally advance the tether elements 114. In other embodiments, the second end 140 of each tether element 114 can be individually manipulated by individual actuators to selectively pull and release the individual tether elements 114.

During deployment of the device 102 at native mitral valve, the end cap 128 can be moved distally and the capsule 108 can be moved to the deployment configuration (FIG. 6A) using the push rod 132 and/or other suitable mechanical or hydraulic deployment mechanisms to unsheathe the device 102 from housing 126 of the capsule 108. As the device 102 exits the housing 126, the device 102 expands and presses against tissue on an inner surface of the annulus of the mitral valve to secure the device 102 in the mitral valve. If the clinician elects to reposition or remove the device 102, the cinching member 112 and the tether elements 114 can be used to partially or fully resheathe the device 102 after full deployment from the capsule 108. More specifically, a clinician can move the cinching member 112 distally (as indicated by arrow 105) by manipulating the push rod 132 via the handle assembly 110 such that the cinching member 112 projects from the distal end of the capsule 108 (e.g., as shown in FIG. 6A). This distal movement of the cinching member 112 constrains the tether elements 114 together within the cinching member 112, which can in turn cinch up the ventricular end portion 134 of the device 102. The clinician can also move (e.g., rotate) the actuator 116 at the handle assembly 110 to pull the tether elements 114 in a proximal direction. This too can cinch the ventricular end portion 134 of the device 102 and allows the clinician to move the delivery catheter 104 distally toward the device 102.

As shown in FIG. 6C, the interplay between the cinching member 112 and the proximal retraction of the tether elements 114 can at least partially collapse the ventricular end portion 134 of the device 102 to a diameter or outer dimension that allows the device 102 to be at least partially received within the distal end portion 118 of the cinching member 112. This pre-collapses the ventricular end portion 134 of the device 102 before resheathing the device 102 within the capsule 108. The clinician can then move the cinching member 112 with the device 102 partially contained therein in a proximal direction toward the capsule 108 so that the device 102 can be partially or fully resheathed within the capsule 108. Alternatively, the capsule 108 can be moved in a distal direction over the cinched end of the device 102 to at least partially resheathe the device 102 within the capsule 108. In other embodiments, the capsule 108 can be moved distally while the cinching member 112 with the device 102 is drawn proximally to initiate resheathing. The partial contraction of the device 102 provided by the tether elements 114 and the cinching member 112 allows the open end of the capsule 108 to easily receive the cinched end because the cinched ventricular end portion 134 has a diameter smaller than that of the delivery capsule 108. For further resheathing, the partial contraction of the device 102 provided by the tether elements 114 and the cinching member 112 allows the capsule 108 to glide along the peripheral walls of the device 102 to further contract the device 102 and move it back into the sheathed, containment configuration in the capsule 108. As described in further detail below with reference to FIGS. 11-24, the device 102 itself can include smooth and continuous outer walls that further facilitate this resheathing. This partial or full resheathing of the device 102 allows clinicians to reposition the device 102, in vivo, or remove the device 102 after full deployment and after the device 102 has contacted tissue of the native valve.

Once the device 102 has been fully deployed within the native valve at its final position, the tether elements 114 can be disengaged from the device 102 to release the device 102 from the delivery system 100. For example, the first ends 138 (FIG. 6B) of the tether elements 114 can be released from their fixed positioned by cutting or otherwise freeing the fixed first ends 138, and the second ends 240 (FIG. 6B) of the tether elements 114 can be pulled in a proximal direction (e.g., by rotating about a spindle on the actuator 116). As the second ends 140 are retracted, the first ends 138 move through the catheter body 106, thread through the attachment features 142 of the device 102, and back into the catheter body 106 such that the tether elements 114 are no longer connected to the device 102. In other embodiments, the tether elements 114 can disengage from the device 102 using other suitable mechanism, such as cutting the tethers at a region closer to the capsule 108. After the tether elements 114 are released from the device 102, the delivery system 100 to be removed from the patient while the device 102 remains implanted at the native valve.

FIG. 7A is a side cross-sectional view of a delivery system 200 with a prosthetic heart valve device 202 ("device 202") in an expanded state in accordance with another embodiment of the present technology, and FIG. 7B is a side isometric view of the delivery system 200 of FIG. 7A with the device 202 in a partially contracted state. The delivery system 200 includes various features at least generally similar to the features of the system 100 described above with reference to FIGS. 6A-6C. For example, the delivery system 200 includes a delivery capsule 208 having a housing 226 that holds the device 202 in a containment configuration, a cinching member 212 extending at least partially through the capsule 208, and at least one tether element 214 that can be used to at least partially resheathe the device 202 after full deployment at a target site (e.g., a native mitral valve). The cross-sectional view of FIGS. 7A and 7B shows only one tether element 214, but the delivery system 200 can include additional tether elements 214 arranged around the device 202 in a similar manner as the illustrated tether element 214. For example, the delivery system 200 may include two, three, four, five, six, or more tether elements 214 spaced apart around the circumference of the device 202. In the embodiment illustrated in FIGS. 7A and 7B, the cinching member 212 has a tubular structure that extends through a catheter body 206 to a proximal portion 206b of the catheter body 206 (distal portion of the catheter body 206 not shown for illustrative purposes) and contains the tether element(s) 214. At the proximal portion 206b of the catheter body 206, a first end 238 of each tether element 214 can be fixed and a second end 240 can be movable to allow a clinician to retract the tether element(s) 214 proximally and release the tether element(s) 214 distally to facilitate resheathing of the device 202. For example, the second end 240 of the tether element 214 can be attached to an actuator (not shown; e.g., the actuator 116 of FIGS. 6A and 6C) at a handle assembly (not shown; e.g., the handle assembly 110 of FIGS. 6A and 6C), which can be used to move the tether element 214.

In the embodiment illustrated in FIGS. 7A and 7B, the delivery system 200 includes a platform 250 that is operably coupled to the capsule 208 to initiate deployment of the device 202 from the capsule 208. The platform 250 can include a distal end portion 252, such as a flange or a pedestal, configured to support a ventricular end portion 234 of the device 202 during deployment and a shaft portion 254 extending proximally from the distal end portion 252 and at least partially through the capsule 208. In various embodiments, the platform 250 maintains the position of the device 202 at a desired target site relative to the longitudinal axis of the catheter body 206 as the capsule 208 is pulled in a proximal direction to unsheathe the device 202. As shown in FIGS. 7A and 7B, the shaft portion 254 of the platform 250 extends through the tubular cinching member 212 to create a tether channel 256 defined by an inner surface of the cinching member 212 and an outer surface of the platform 250 and configured to receive the tether element(s) 214. Each tether element 214 extends from the first end 238, through the tether channel 256, through one or more attachment features 242 on the ventricular end portion 234 of the device 202, and back through the tether channel 256 to the proximal portion 206b of the catheter body 206 where the second end 240 can be operably coupled to an actuator for controlling the tether element 214. As shown in FIGS. 7A and 7B, the distal end portion 252 of the platform 250 can also include one or more attachment elements 258 that releasably connect the tether element(s) 214 to the platform 250. In the illustrated embodiment, the attachment elements 258 are eyelets or loops through which the tether element(s) 214 can be threaded. In other embodiments, the attachment elements are hooks or other features for releasably engaging the tether elements 214.

In certain embodiments, the cinching member 212 and the platform 250 are fixed relative to each other such that movement of the platform 250 translates to movement of the cinching member 212 and vice versa. During deployment, the device 202 expands from the capsule 208 as the housing 226 of the capsule 208 moves proximally and/or the platform 250 pushes the device 202 distally. After the device 202 has been fully expanded, a distal end portion 218 of the cinching member 212 can be moved such that it projects distally from the capsule 208 and, due to the fixed relationship between the platform 250 and the cinching member 212, the distal end portion 252 of the platform 250 projects distally from the cinching member 212. In this fully expanded state shown in FIG. 7A, the clinician can pull the tether elements 214 in a proximal direction to at least partially resheathe the device 202 to reposition or otherwise manipulate the device 202. The proximal retraction of the tether elements 214 partially collapses the ventricular end portion 234 of the device 202 such that it moves inward in the direction of arrows 207 (FIG. 7A) toward the distal end portion 252 of the platform 250 and hugs the platform 250. As shown in FIG. 7B, proximal retraction of the tether elements 214 may also move the device 202 in a proximal direction toward the cinching member 212 and cause the ventricular end portion 234 to wrap around the distal end portion 252 of the platform 250. In certain embodiments, the partially collapsed ventricular end portion 234 of the device 202 may cinch against the area between the platform 250 and the distal end portion 218 of the cinching member 212 or the ventricular end portion 234 may be at least partially received within the distal end portion 218 of the cinching member 212. In this embodiment, the ventricular end portion 234 of the device 202 contracts to the inner diameter of the cinching member 212, which is less than the diameter of the capsule 208.

When the device 202 is in the partially collapsed state (FIG. 7B), the clinician can move the cinching member 212 and/or the platform 250 in a proximal direction to partially or fully resheathe the device 202 in the capsule 208, and/or the clinician can move the capsule 208 in a distal direction over the cinched end of the device 202. The partially collapsed device 202 allows the open end of the capsule 208 to easily slide over the cinched end because the cinched ventricular end portion 234 has a diameter smaller than that of the delivery capsule 208. In addition, the arrangement shown in FIG. 7B in which the ventricular end portion 234 of the device 202 hugs or wraps around the distal end portion 252 of the platform 250 allows the platform 250 to provide support to the collapsed portion of the device 202 during resheathing and is expected to enhance stability at the ventricular end portion 234 during resheathing. After the cinched ventricular end portion 234 has been received in the capsule 208, resheathing can continue by sliding the capsule 208 along the peripheral walls of the device 202 to further collapse the device 102 and move the device 102 back into its unexpanded state to the containment configuration in the capsule 208. The partially or fully sheathed device 202 can then be repositioned and redeployed at a desired location. After final deployment at the target site, the clinician can disengage the tether elements 214 from the device 202 by severing the fixed first ends 238 to release the device 202 from the delivery system 200 and remove the delivery system 200 from the patient.

FIG. 8A is a is a partial cross-sectional isometric view of a delivery system 300 with a prosthetic heart valve device 302 ("device 302") in an expanded state in accordance with yet another embodiment of the present technology, and FIG. 8B is an enlarged side view of a tether element connection site for the delivery system 300. The delivery system 300 includes various features at least generally similar to the features of the delivery system 200 described above with reference to FIGS. 7A and 7B. For example, the delivery system 300 includes an elongated catheter body 306 ("catheter body 306"), a delivery capsule 308 carried by a distal portion 306a of the catheter body 306, a cinching member 312 extending at least partially through the capsule 308, and a platform 350 with a distal end portion 352 and a shaft portion 354 that extends through the cinching member 312. In the illustrated embodiment, the cinching member 312 attaches to a distal region of the shaft portion 354 of the platform 350 and, therefore, the platform 350 and the cinching member 312 are fixed relative to each other. The platform 350 can be configured to move the capsule 308 between the containment configuration and the deployment configuration (FIG. 8A) to unsheathe and resheathe the device 302.

As shown in FIG. 8A, the delivery system 300 further includes tether elements 314 that extend along the length of the catheter body 306 and through a tether channel 358 defined by the platform 350. Accordingly, the shaft portion 354 of the platform 350 may be a tubular structure. In other embodiments, the cinching member 312 extends alongside a greater length of the shaft portion 354 and/or has a tubular structure that defines a channel for receiving the tether elements 314. The tether elements 314 are releasably coupled to attachment features 342 at a ventricular end portion 334 of the device 302. An actuator 316 can be rotated (as indicated by arrow 309) to proximally retract the tether elements 314, which in turn pulls the ventricular end portion 334 of the device 302 inward toward a distal end portion 352 of the platform 350 (as indicated by arrows 307) to partially collapse the device 302. In other embodiments, the actuator 316 can be manipulated using other suitable means for retracting and releasing the tether elements 314. Similar to the delivery system 200 of FIGS. 7A and 7B, the partially collapsed device 302 can hug and/or wrap around the distal end portion 352 of the platform 350 to facilitate resheathing the device 302 after full deployment.

As shown best in FIG. 8B, the attachment features 342 of the delivery system 300 are hooks 360 positioned at the ventricular end portion 334 of the device 302, and the tether elements 314 form loops 362 that extend around the hooks 360. The hooks 360 may each have a one-way notch that allows the hook 360 to flex open to receive the tether element 314, and flex closed after insertion to prevent disengagement of the tether element 314 from the hook 360. In other embodiments, the delivery system 300 can include both hooks 360 and the eyelet attachment structures of FIGS. 6A-7B or the hooks 360 can be replaced by the eyelet attachment structures such that the tether elements 314 are threaded through the eyelets.

Figure 8C:
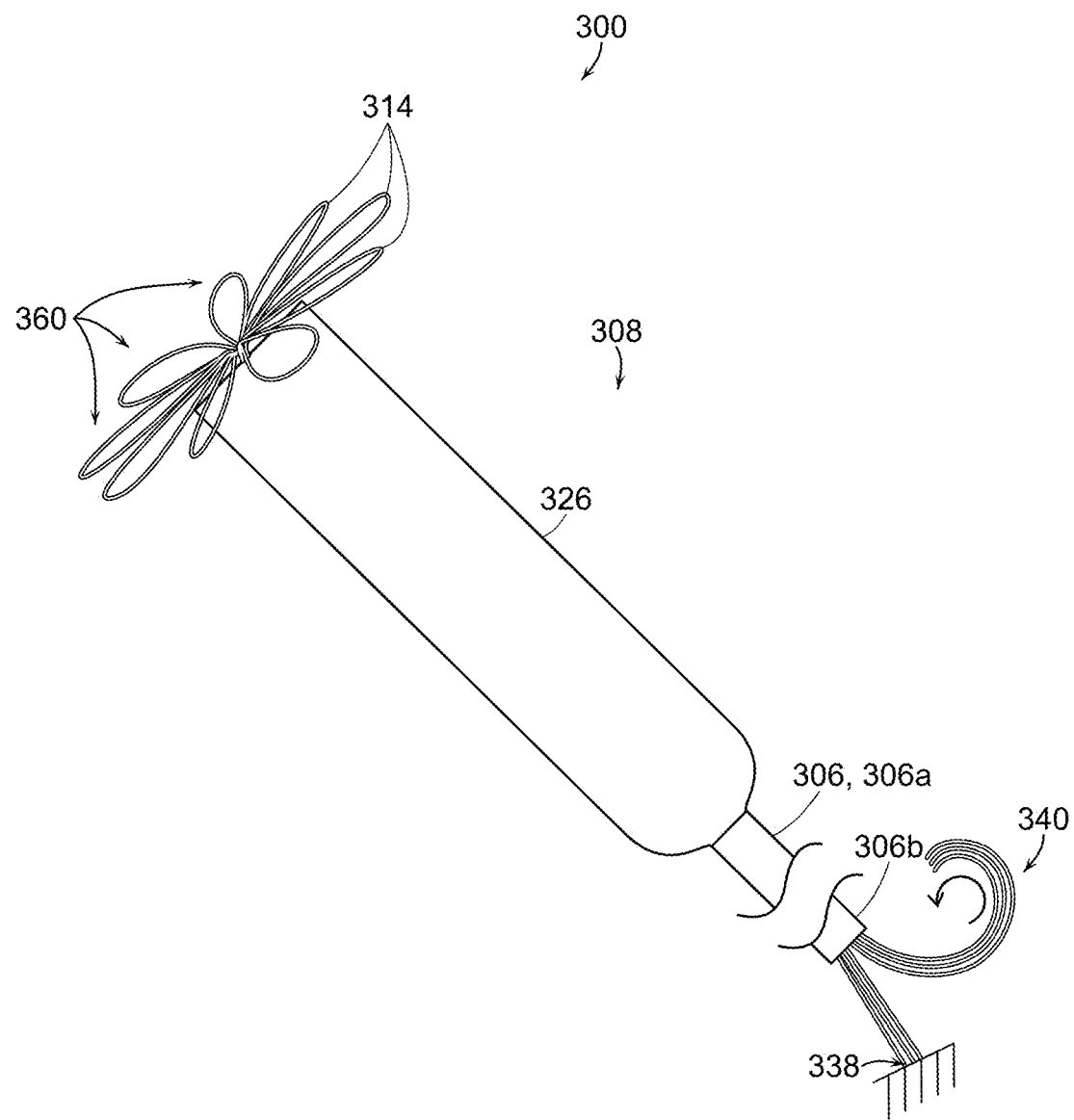
FIG. 8C is a partially schematic isometric illustration of a tethering arrangement for the delivery system of FIG. 8A.

Unlike the tether elements of FIGS. 6A-7B that extend across the prosthetic device between two or more attachment features, the individual tether elements 314 of the delivery system 300 extend from of the distal end portion 318 of the cinching member 312, wrap around a single hook 360, and extend back through the distal end portion 318 of the cinching member 312 into the tether channel 356 to form individual loops 362. FIG. 8C, for example, is a partially schematic isometric illustration of the tethering arrangement for the delivery system 300. As shown in FIG. 8C, the loops 362 of the tether elements 314 extend from the housing 326 of the capsule 308 and splay outward into a petal-like configuration with loops 362 arranged in a manner to engage corresponding attachment features 342 (e.g., hooks 360 of FIGS. 8A and 8B) positioned circumferentially around the device 302. Each loop 362 is defined by a single tether element 314 that extends from a fixed first end 338 at the proximal portion 306b of the catheter body 306, through the catheter body 306 into engagement with an attachment feature 342 (FIG. 8A), and back through the catheter body 306 where a second end 340 of the tether element 314 attaches to the actuator 316 (FIG. 8A) that can be manipulated to proximally retract the tether element 314. In the illustrated embodiment, the delivery system 300 includes nine loops 362, but in other embodiments the delivery system 300 can include fewer than nine loops 362 or more than nine loops 362 that attach to one or more corresponding attachment features 342 on the ventricular end portion 334 of the device 302 (FIG. 8A). The looped tether elements 314 can be attached to the hooks 360 when the device 302 is loaded in the capsule 308 and continuously engage the hooks 360 until the clinician is ready to fully release the device 302 from the delivery system 300. After deployment and optional resheathing, the tether elements 314 can be disconnected from the hooks 360 by releasing the fixed ends of the tether elements 314 and pulling the tether elements 314 proximally until the tether elements 314 no longer loop around the hooks 360.

Figure 9A:
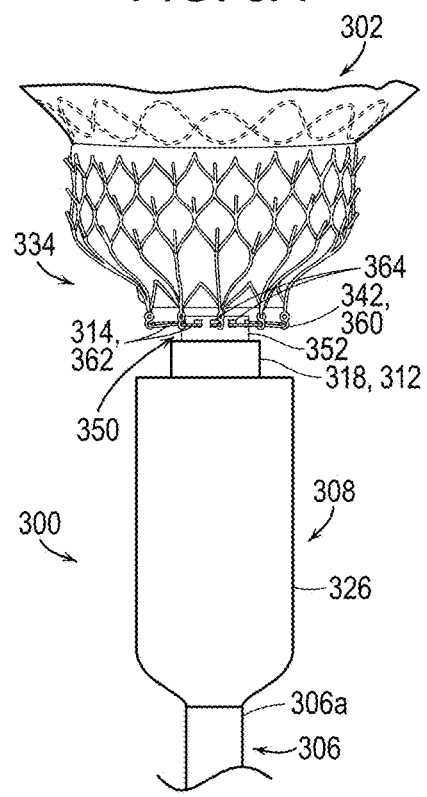
FIGS. 9A-9C are a series of illustrations showing the resheathing of a prosthetic heart valve device using the delivery system of FIGS. 8A-8C in accordance with embodiments of the present technology
Figure 9B:
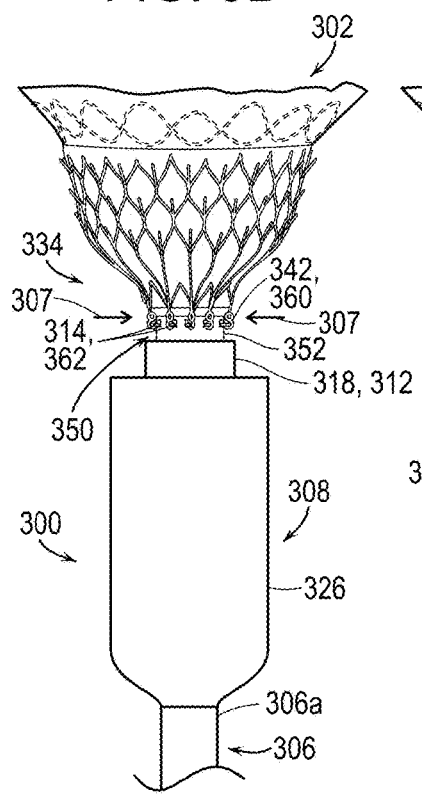
Figure 9C:
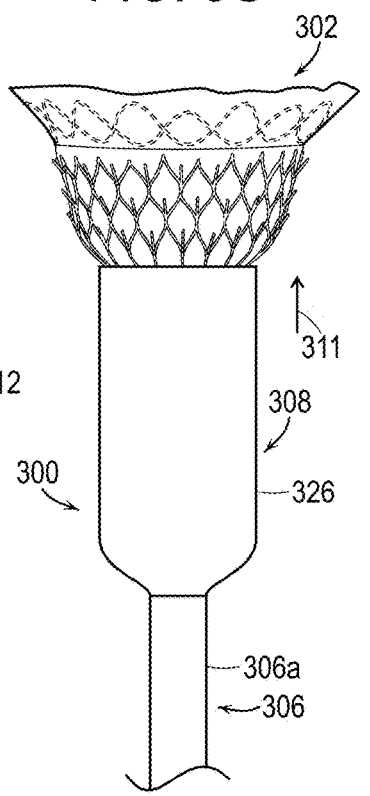

FIGS. 9A-9C are a series of illustrations showing the resheathing of the device 302 using the delivery system 300 of FIGS. 8A-8C in accordance with embodiments of the present technology. In FIG. 9A, the device 302 has been fully deployed from the housing 326 of the capsule 308, and the tether elements 314 maintain engagement with the device 302 while the device 302 is in the fully expanded state. The distal portion 318 of the cinching member 312 extends distally from the open capsule 308, and the distal end portion 352 of the platform 350 projects distally therefrom. As shown in FIG. 9A, the distal end portion 352 of the platform 350 includes a plurality of openings 364 through which the loop 362 of each tether element 314 extends so that the individual loops 362 can attach to corresponding hooks 360 on the ventricular end portion 334 of the device 302. In other embodiments, the distal end portion 352 of the platform 350 has a single opening at the distal-most end through which all of the tether elements 314 exit the tether channel 358 of the platform 350.

Referring to FIG. 9B, if the clinician elects to resheathe the device 302, the tether elements 314 can be retracted proximally using the actuator 316. This proximal retraction pulls the tether elements 314 inward toward the platform 350 in the direction of arrows 307, and this in turn cinches the ventricular end portion 334 of the device 302 such that it hugs the distal end portion 352 of the platform 350. As shown in FIG. 9C, the capsule 308 can then be moved in a distal direction (as indicated by arrow 311) to slide over the partially collapsed device 302 and at least partially resheathe the device 302 to allow for in vivo repositioning or removal of the device. The cinched ventricular end portion 334 and the support provided by the platform 350 are expected to facilitate resheathing of the device 302 after full deployment. After final deployment at the target site, the clinician can fully release the device 302 from the delivery system 300 by releasing (e.g., cutting) the first ends 338 (FIG. 8C) of the tether elements 314, and manipulating the actuator 316 to proximally retract the tether elements 314 until they disengage from the hooks 360 on the device 302.

Figure 10:
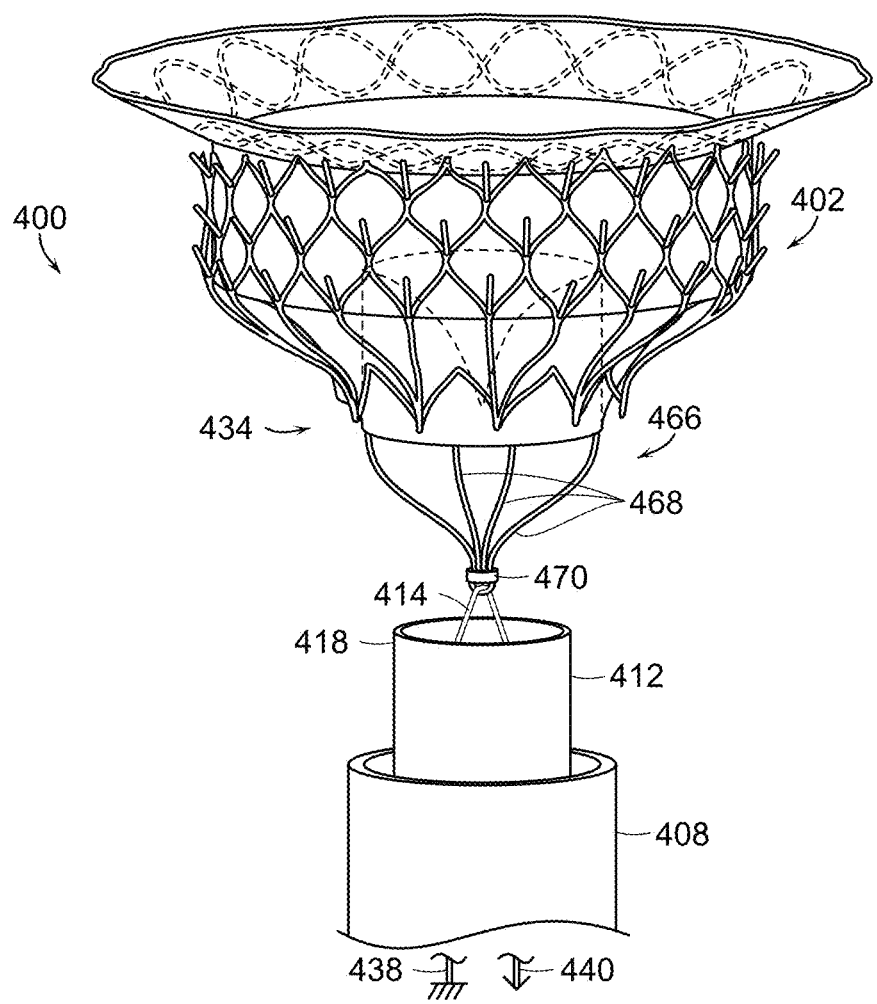
FIG. 10 is a side isometric view of a delivery system for a prosthetic heart valve device configured in accordance with a further embodiment of the present technology.

FIG. 10 is a side isometric view of a portion of a delivery system 400 for a prosthetic heart valve device 402 ("device 402") configured in accordance with a further embodiment of the present technology. The delivery system 400 can include certain features at least generally similar to the features of the delivery systems 100, 200 and 300 described above with reference to FIGS. 6A-9C. For example, the delivery system 400 includes at least one tether element 414 that extends through an elongated catheter body (not shown), a delivery capsule 408, and a cinching member 412 at a distal portion of the catheter body. The tether element 414 has a fixed first end 438 and a second end 440 operably coupled to an actuator (not shown) that can be manipulated to retract the tether element 414 proximally. As shown in FIG. 10, the device 402 includes a permanently attached tethering assembly 466 extending proximally from a ventricular end portion 434 of the device 402. The tethering assembly 466 includes a plurality of arm members 468 that are fixedly attached at one end to the ventricular end portion 434 of the device 402 via permanent attachment features, such as fasteners or stitches. The opposite ends of the arm members 468 are attached to an engagement feature 470, which can include a loop or other structure through which the tether element 414 can be threaded. The arm members 468 can be made of metal or polymeric wires, cables, or other suitable structures similar to the tether elements 114, 214 and 314 described above.

The device 402 can be fully deployed (FIG. 10) from the capsule 408 at a target site (e.g., a native mitral valve). The tether element 414 in conjunction with the permanent tether assembly 466 of the device 402 can then be used to facilitate partial or full resheathing of the fully deployed device 402. More specifically, an actuator (not shown; e.g., the actuators 116, 216 and 316 described above) can be manipulated (e.g., twisted or pulled) to proximally retract the tether element(s) 414. This pulls the ventricular end portion 434 of the device 402 toward a distal end portion 418 of the cinching member 412 and may partially collapse the ventricular end portion 434 of the device 402. When the distal end portion 418 of the cinching member 412 meets the tethering assembly 466 (via distal movement of the cinching member 412 or proximal movement of the device 402), the distal end portion 418 can slide along the taught arm members 468 and allow the ventricular end portion 434 of the device 402 to contract into the cinching member 412. The taught arm members 468 can serve as rails the guide the device 402 into the cinching member 412 and smoothly glide into it. The capsule 408 can then move over the partially collapsed device 402 to partially or fully resheathe the device 402. After final positioning of the device 402, the first end 438 of the tether element(s) 414 can be severed and threaded through the engagement feature 470 disengage the device 402 from the delivery system 400. After the device 402 has been released from the delivery system 400, the tethering assembly 466 can be used to recapture the device 402 and allow for subsequent resheathing.

Selected Embodiments of Prosthetic Heart Valve Devices

The delivery systems 100, 200, 300 and 400 described above with reference to FIGS. 6A-10 can be configured to deliver various prosthetic heart valve devices, such as prosthetic valve devices for replacement of the mitral valve and/or other valves (e.g., a bicuspid or tricuspid valve) in the heart of the patient. Examples of these prosthetic heart valve devices, system components, and associated methods are described in this section with reference to FIGS. 11A-24. Specific elements, substructures, advantages, uses, and/or other features of the embodiments described with reference to FIGS. 11A-24 can be suitably interchanged, substituted or otherwise configured with one another. Furthermore, suitable elements of the embodiments described with reference to FIGS. 11A-24 can be used as stand-alone and/or self-contained devices.

Figure 11A:
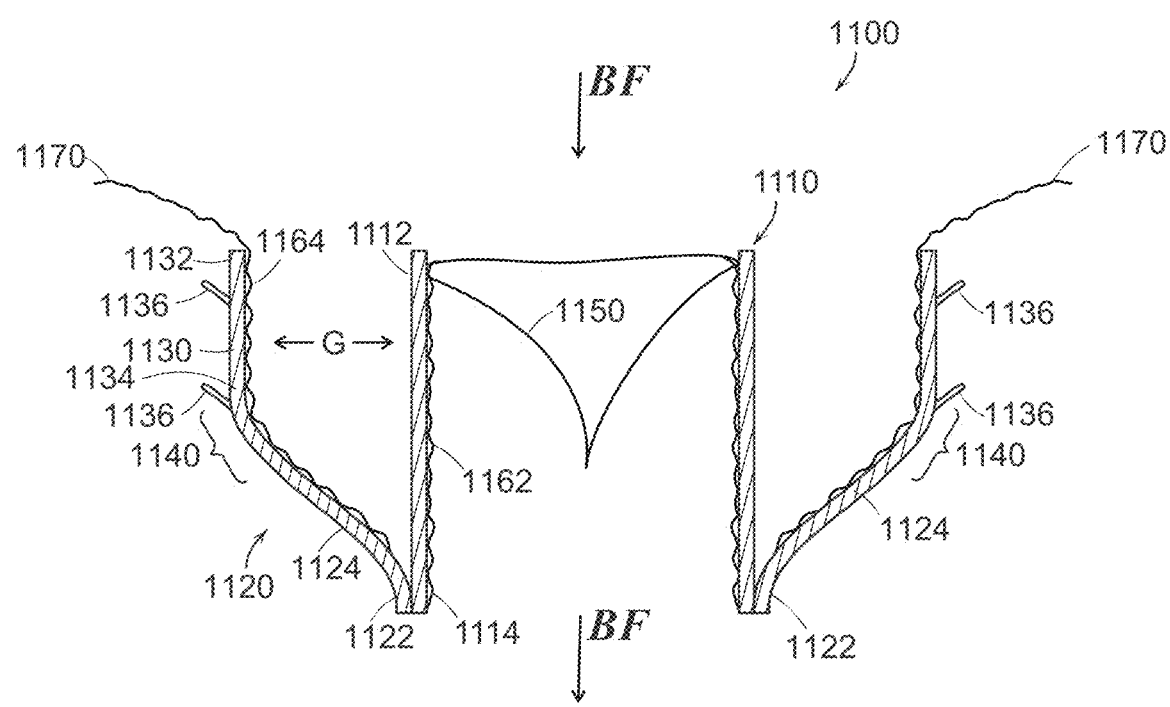
FIG. 11A is a cross-sectional side view and FIG. 11B is a top view schematically illustrating a prosthetic heart valve device in accordance with an embodiment of the present technology.
Figure 11B:
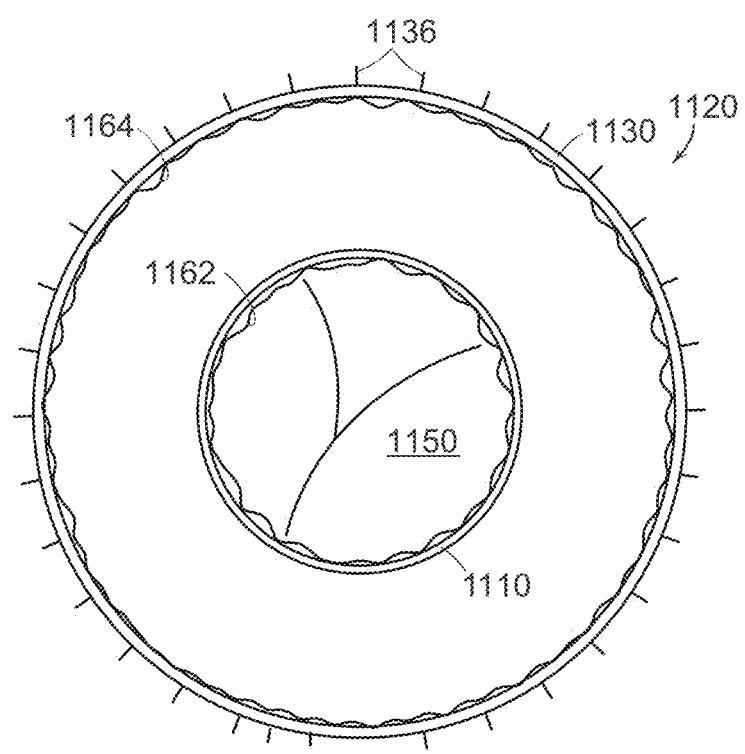

FIG. 11A is a side cross-sectional view and FIG. 11B is a top plan view of a prosthetic heart valve device ("device") 1100 in accordance with an embodiment of the present technology. The device 1100 includes a valve support 1110, an anchoring member 1120 attached to the valve support 1110, and a prosthetic valve assembly 1150 within the valve support 1110. Referring to FIG. 11A, the valve support 1110 has an inflow region 1112 and an outflow region 1114. The prosthetic valve assembly 1150 is arranged within the valve support 1110 to allow blood to flow from the inflow region 1112 through the outflow region 1114 (arrows BF), but prevent blood from flowing in a direction from the outflow region 1114 through the inflow region 1112.

In the embodiment shown in FIG. 11A, the anchoring member 1120 includes a base 1122 attached to the outflow region 1114 of the valve support 1110 and a plurality of arms 1124 projecting laterally outward from the base 1122. The anchoring member 1120 also includes a fixation structure 1130 extending from the arms 1124. The fixation structure 1130 can include a first portion 1132 and a second portion 1134. The first portion 1132 of the fixation structure 1130, for example, can be an upstream region of the fixation structure 1130 that, in a deployed configuration as shown in FIG. 11A, is spaced laterally outward apart from the inflow region 1112 of the valve support 1110 by a gap G. The second portion 1134 of the fixation structure 1130 can be a downstream-most portion of the fixation structure 1130. The fixation structure 1130 can be a cylindrical ring (e.g., straight cylinder or conical), and the outer surface of the fixation structure 1130 can define an annular engagement surface configured to press outwardly against a native annulus of a heart valve (e.g., a mitral valve). The fixation structure 1130 can further include a plurality of fixation elements 1136 that project radially outward and are inclined toward an upstream direction. The fixation elements 1136, for example, can be barbs, hooks, or other elements that are inclined only in the upstream direction (e.g., a direction extending away from the downstream portion of the device 1100).

Referring still to FIG. 11A, the anchoring member 1120 has a smooth bend 1140 between the arms 1124 and the fixation structure 1130. For example, the second portion 1134 of the fixation structure 1130 extends from the arms 1124 at the smooth bend 1140. The arms 1124 and the fixation structure 1130 can be formed integrally from a continuous strut or support element such that the smooth bend 1140 is a bent portion of the continuous strut. In other embodiments, the smooth bend 1140 can be a separate component with respect to either the arms 1124 or the fixation structure 1130. For example, the smooth bend 1140 can be attached to the arms 1124 and/or the fixation structure 1130 using a weld, adhesive or other technique that forms a smooth connection. The smooth bend 1140 is configured such that the device 1100 can be recaptured in a capsule or other container after the device 1100 has been at least partially deployed.

The device 1100 can further include a first sealing member 1162 on the valve support 1110 and a second sealing member 1164 on the anchoring member 1120. The first and second sealing members 1162, 1164 can be made from a flexible material, such as Dacron® or another type of polymeric material. The first sealing member 1162 can cover the interior and/or exterior surfaces of the valve support 1110. In the embodiment illustrated in FIG. 11A, the first sealing member 1162 is attached to the interior surface of the valve support 1110, and the prosthetic valve assembly 1150 is attached to the first sealing member 1162 and commissure portions of the valve support 1110. The second sealing member 1164 is attached to the inner surface of the anchoring member 1120. As a result, the outer annular engagement surface of the fixation structure 1130 is not covered by the second sealing member 1164 so that the outer annular engagement surface of the fixation structure 1130 directly contacts the tissue of the native annulus.

The device 1100 can further include an extension member 1170. The extension member 1170 can be an extension of the second sealing member 1164, or it can be a separate component attached to the second sealing member 1164 and/or the first portion 1132 of the fixation structure 1130. The extension member 1170 can be a flexible member that, in a deployed state (FIG. 11A), flexes relative to the first portion 1132 of the fixation structure 1130. In operation, the extension member 1170 provides tactile feedback or a visual indicator (e.g., on echocardiographic or fluoroscopic imaging systems) to guide the device 1100 during implantation such that the device 1100 is located at a desired elevation and centered relative to the native annulus. As described below, the extension member 1170 can include a support member, such as a metal wire or other structure, that can be visualized via fluoroscopy or other imaging techniques during implantation. For example, the support member can be a radiopaque wire.

Figure 12A:
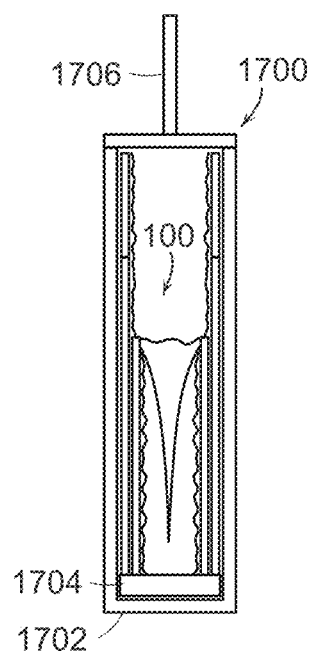
FIGS. 12A and 12B are cross-sectional side views schematically illustrating aspects of delivering a prosthetic heart valve device in accordance with an embodiment of the present technology.
Figure 12B:
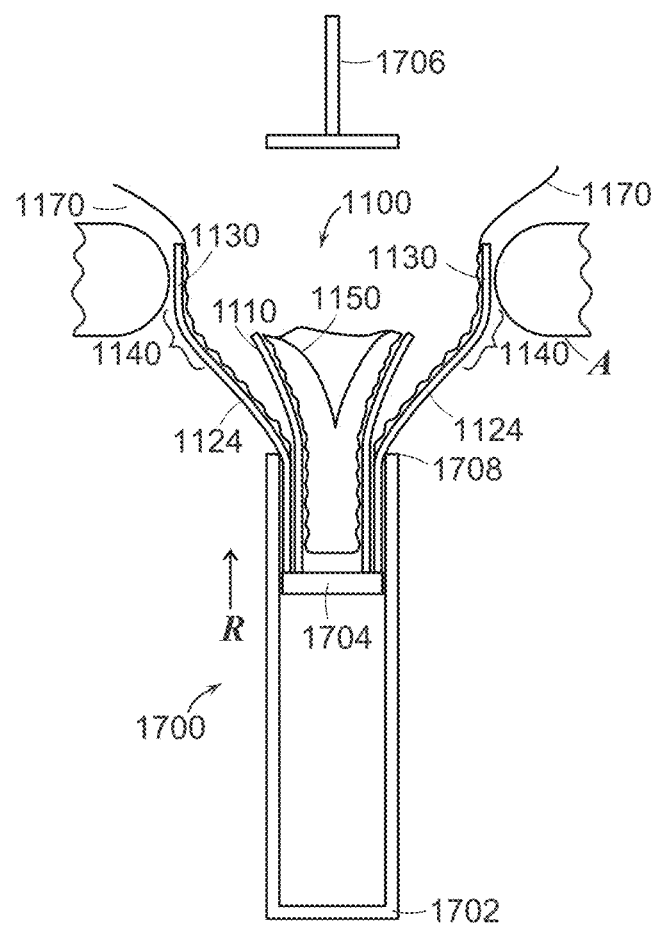

FIGS. 12A and 12B are cross-sectional views illustrating an example of the operation of the smooth bend 1140 between the arms 1124 and the fixation structure 1130 in the recapturing of the device 1100 after partial deployment. FIG. 12A schematically shows the device 1100 loaded into a capsule 1700 of a delivery system in a delivery state, and FIG. 12B schematically shows the device 1100 in a partially deployed state. Referring to FIG. 12A, the capsule 1700 has a housing 1702, a platform or support 1704, and a top 1706. In the delivery state shown in FIG. 12A, the device 1100 is in a low-profile configuration suitable for delivery through a catheter or cannula to a target implant site at a native heart valve.

Referring to FIG. 12B, the housing 1702 of the capsule 1700 has been moved distally such that the extension member 1170, fixation structure 1130 and a portion of the arms 1124 have been released from the housing 1702 in a partially deployed state. This is useful for locating the fixation structure 1130 at the proper elevation relative to the native valve annulus A such that the fixation structure 1130 expands radially outward into contact the inner surface of the native annulus A. However, the device 1100 may need to be repositioned and/or removed from the patient after being partially deployed. To do this, the housing 1702 is retracted (arrow R) back toward the fixation structure 1130. As the housing 1702 slides along the arms 1124, the smooth bend 1140 between the arms 1124 and the fixation structure 1130 allows the edge 1708 of the housing 1702 to slide over the smooth bend 1140 and thereby recapture the fixation structure 1130 and the extension member 1170 within the housing 1702. The device 1100 can then be removed from the patient or repositioned for redeployment at a better location relative to the native annulus A. Further aspects of prosthetic heart valve devices in accordance with the present technology and their interaction with corresponding delivery devices are described below with reference to FIGS. 13-24.

Figure 13:
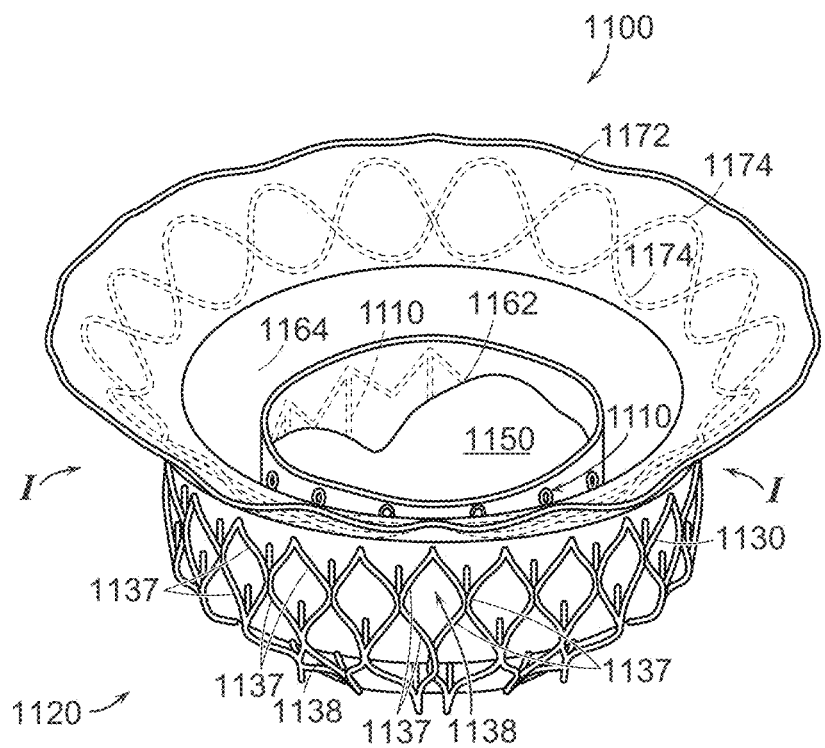
FIG. 13 is a top isometric view of a prosthetic heart valve device in accordance with an embodiment of the present technology.

FIG. 13 is a top isometric view of an example of the device 1100. In this embodiment, the valve support 1110 defines a first frame (e.g., an inner frame) and fixation structure 1130 of the anchoring member 1120 defines a second frame (e.g., an outer frame) that each include a plurality of structural elements. The fixation structure 1130, more specifically, includes structural elements 1137 arranged in diamond-shaped cells 1138 that together form at least a substantially cylindrical ring when freely and fully expanded as shown in FIG. 13. The structural elements 1137 can be struts or other structural features formed from metal, polymers, or other suitable materials that can self-expand or be expanded by a balloon or other type of mechanical expander.

In several embodiments, the fixation structure 1130 can be a generally cylindrical fixation ring having an outwardly facing engagement surface. For example, in the embodiment shown in FIG. 13, the outer surfaces of the structural elements 1137 define an annular engagement surface configured to press outwardly against the native annulus in the deployed state. In a fully expanded state without any restrictions, the walls of the fixation structure 1130 are at least substantially parallel to those of the valve support 1110. However, the fixation structure 1130 can flex inwardly (arrow I) in the deployed state when it presses radially outwardly against the inner surface of the native annulus of a heart valve.

The embodiment of the device 1100 shown in FIG. 13 includes the first sealing member 1162 lining the interior surface of the valve support 1110, and the second sealing member 1164 along the inner surface of the fixation structure 1130. The extension member 1170 has a flexible web 1172 (e.g., a fabric) and a support member 1174 (e.g., metal or polymeric strands) attached to the flexible web 1172. The flexible web 1172 can extend from the second sealing member 1164 without a metal-to-metal connection between the fixation structure 1130 and the support member 1174. For example, the extension member 1170 can be a continuation of the material of the second sealing member 1164. Several embodiments of the extension member 1170 are thus a malleable or floppy structure that can readily flex with respect to the fixation structure 1130. The support member 1174 can have a variety of configurations and be made from a variety of materials, such as a double-serpentine structure made from Nitinol.

Figure 14:
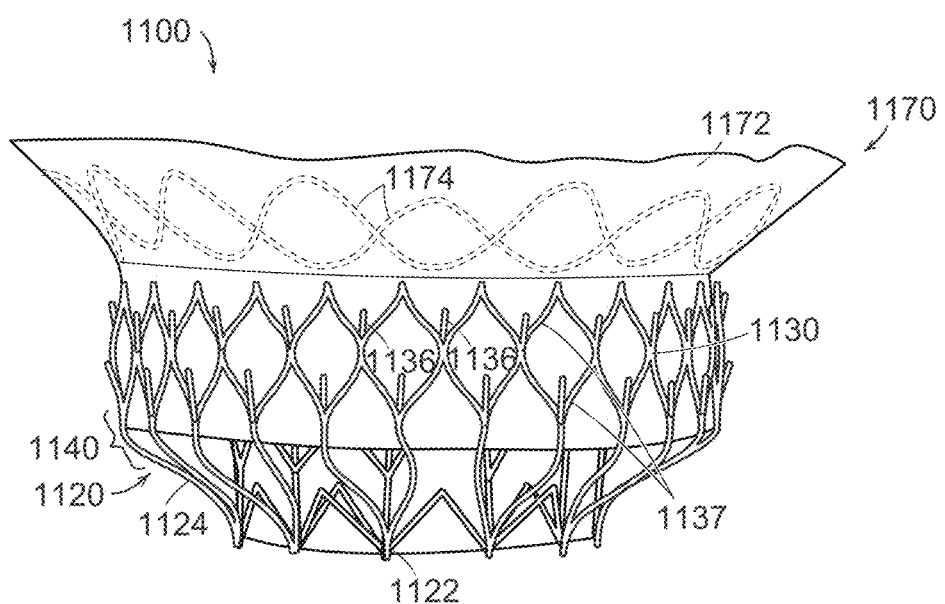
FIG. 14 is a side view and FIG. 15 is a bottom isometric view of the prosthetic heart valve device of FIG. 13.
Figure 15:
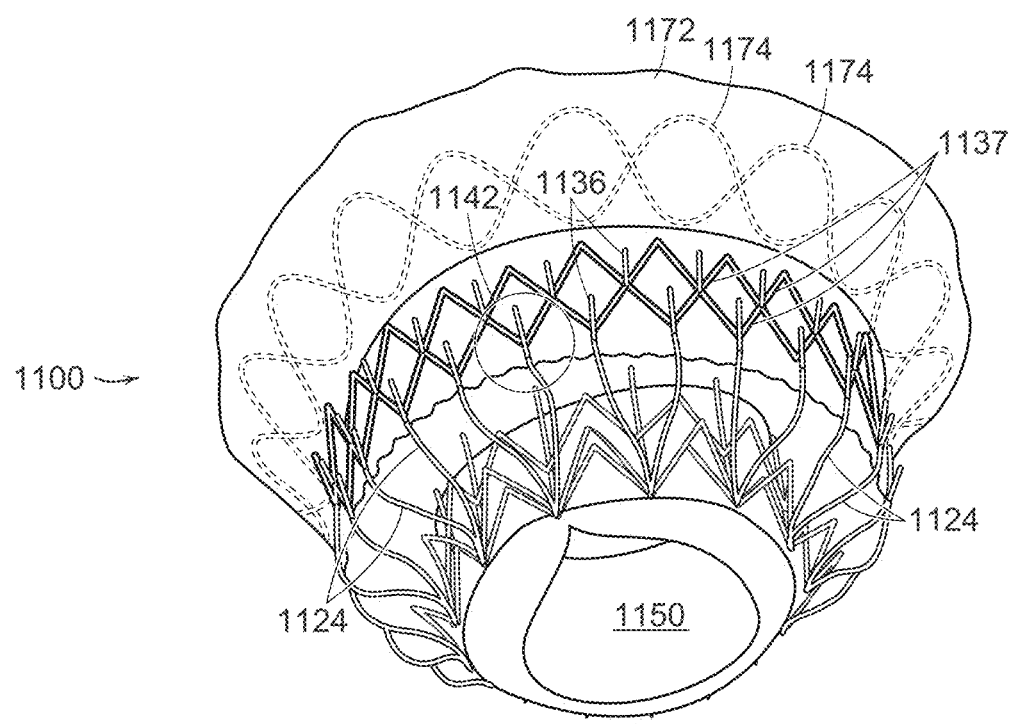

FIG. 14 is a side view and FIG. 15 is a bottom isometric view of the device 1100 shown in FIG. 13. Referring to FIG. 14, the arms 1124 extend radially outward from the base portion 1122 at an angle α selected to position the fixation structure 1130 radially outward from the valve support 1110 (FIG. 13) by a desired distance in a deployed state. The angle α is also selected to allow the edge 1708 of the delivery system housing 1702 (FIG. 12B) to slide from the base portion 1122 toward the fixation structure 1130 during recapture. In many embodiments, the angle α is 15°-75°, or more specifically 15°-60°, or still more specifically 30°-45°. The arms 1124 and the structural elements 1137 of the fixation structure 1130 can be formed from the same struts (i.e., formed integrally with each other) such that the smooth bend 1140 is a continuous, smooth transition from the arms 1124 to the structural elements 1137. This is expected to enable the edge 1708 of the housing 1702 to more readily slide over the smooth bend 1140 in a manner that allows the fixation structure 1130 to be recaptured in the housing 1702 of the capsule 1700 (FIG. 12B). Additionally, by integrally forming the arms 1124 and the structural elements 1137 with each other, it inhibits damage to the device 1100 at a junction between the arms 1124 and the structural elements 1137 compared to a configuration in which the arms 1124 and structural elements 1137 are separate components and welded or otherwise fastened to each other.

Referring to FIGS. 14 and 15, the arms 1124 are also separated from each other along their entire length from where they are connected to the base portion 1122 through the smooth bend 1140 (FIG. 14) to the structural elements 1137 of the fixation structure 1130. The individual arms 1124 are thus able to readily flex as the edge 1708 of the housing 1702 (FIG. 12B) slides along the arms 1124 during recapture. This is expected to reduce the likelihood that the edge 1708 of the housing 1702 will catch on the arms 1124 and prevent the device 1100 from being recaptured in the housing 1702.

In one embodiment, the arms 1124 have a first length from the base 1122 to the smooth bend 1140, and the structural elements 1137 of the fixation structure 1130 at each side of a cell 1138 (FIG. 13) have a second length that is less than the first length of the arms 1124. The fixation structure 1130 is accordingly less flexible than the arms 1124. As a result, the fixation structure 1130 is able to press outwardly against the native annulus with sufficient force to secure the device 1100 to the native annulus, while the arms 1124 are sufficiently flexible to fold inwardly when the device is recaptured in a delivery device.

In the embodiment illustrated in FIGS. 13-15, the arms 1124 and the structural elements 1137 are configured such that each arm 1124 and the two structural elements 1137 extending from each arm 1124 formed a Y-shaped portion 1142 (FIG. 15) of the anchoring member 1120. Additionally, the right-hand structural element 1137 of each Y-shaped portion 1142 is coupled directly to a left-hand structural element 1137 of an immediately adjacent Y-shaped portion 1142. The Y-shaped portions 1142 and the smooth bends 1140 are expected to further enhance the ability to slide the housing 1702 along the arms 1124 and the fixation structure 1130 during recapture.

Figure 16:
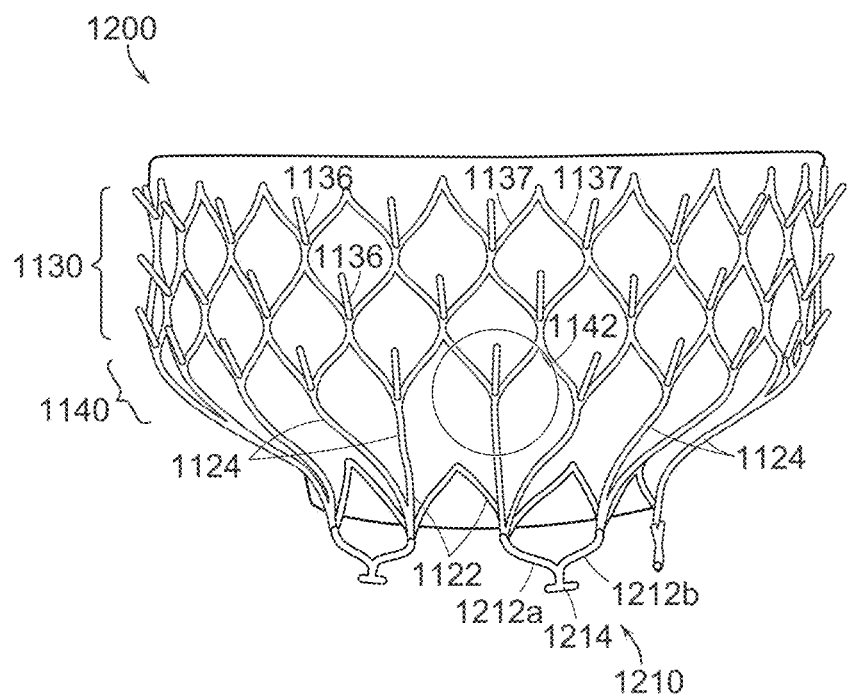
FIG. 16 is a side view and FIG. 17 is a bottom isometric view of a prosthetic heart valve device in accordance with an embodiment of the present technology.
Figure 17:
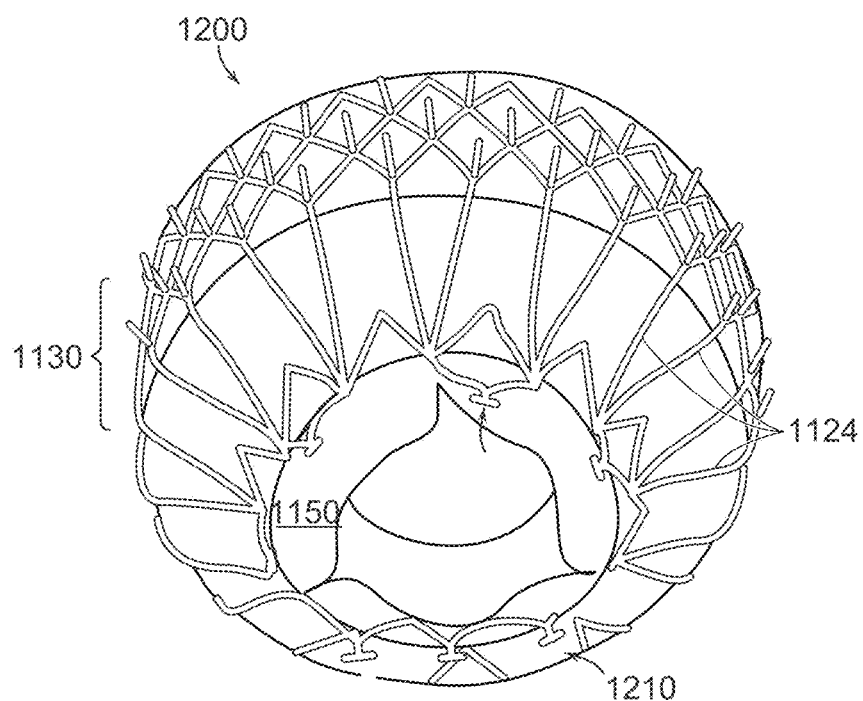

FIG. 16 is a side view and FIG. 17 is a bottom isometric view of a prosthetic heart valve device ("device") 1200 in accordance with another embodiment of the present technology. The device 1200 is shown without the extension member 1170 (FIGS. 13-15), but the device 1200 can further include the extension member 1170 described above. The device 1200 further includes extended connectors 1210 projecting from the base 1122 of the anchoring member 1120. Alternatively, the extended connectors 1210 can extend from the valve support 1110 (FIGS. 11A-15) in addition to or in lieu of extending from the base 1122 of the anchoring member 1120. The extended connectors 1210 can include a first strut 1212a attached to one portion of the base 1122 and a second strut 1212b attached to another portion of the base 1122. The first and second struts 1212a-b are configured to form a V-shaped structure in which they extend toward each other in a downstream direction and are connected to each other at the bottom of the V-shaped structure. The V-shaped structure of the first and second struts 1212a-b causes the extension connector 1210 to elongate when the device 1200 is in a low-profile configuration within the capsule 1700 (FIG. 12A) during delivery or partial deployment. When the device 1200 is fully released from the capsule 1700 (FIG. 12A) the extension connectors 1210 foreshorten to avoid interfering with blood flow along the left ventricular outflow tract.

The extended connectors 1210 further include an attachment element 1214 configured to releasably engage a delivery device. The attachment element 1214 can be a T-bar or other element that prevents the device 1200 from being released from the capsule 1700 (FIG. 12A) of a delivery device until desired. For example, a T-bar type attachment element 1214 can prevent the device 1200 from moving axially during deployment or partial deployment until the housing 1702 (FIG. 12A) moves beyond the portion of the delivery device engaged with the attachment elements 1214. This causes the attachment elements 1214 to disengage from the capsule 1700 (FIG. 12A) as the outflow region of the valve support 1110 and the base 1122 of the anchoring member 1120 fully expand to allow for full deployment of the device 1200.

Figure 18:
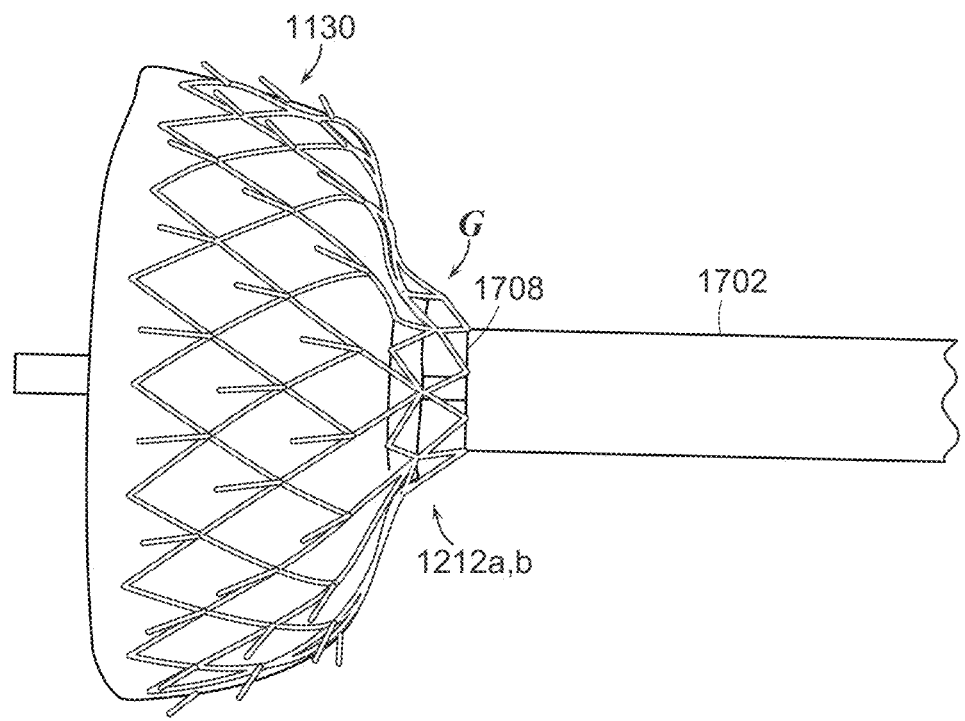
FIG. 18 is a side view and FIG. 19 is a bottom isometric view of the prosthetic heart valve device of FIGS. 17 and 18 at a partially deployed state with respect to a delivery device.
Figure 19:
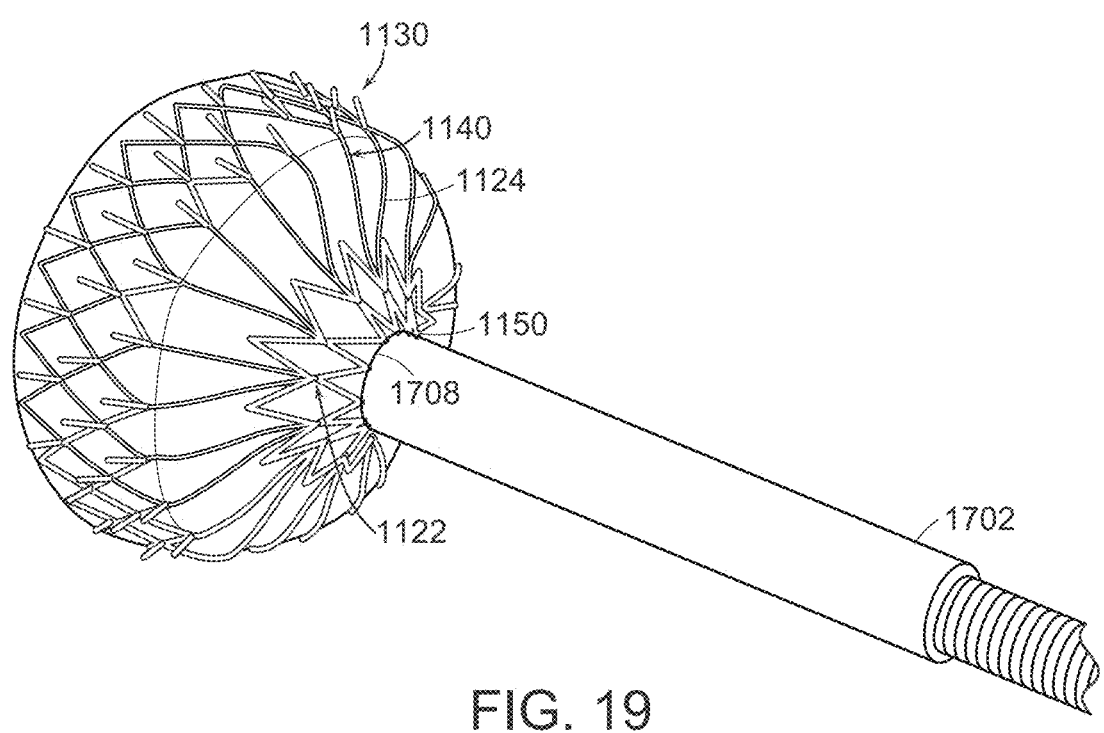

FIG. 18 is a side view and FIG. 19 is a bottom isometric view of the device 1200 in a partially deployed state in which the device 1200 is still capable of being recaptured in the housing 1702 of the delivery device 1700. Referring to FIG. 18, the device 1200 is partially deployed with the fixation structure 1130 substantially expanded but the attachment elements 1214 (FIG. 16) still retained within the capsule 1700. This is useful for determining the accuracy of the position of the device 1200 and allowing blood to flow through the functioning replacement valve during implantation while retaining the ability to recapture the device 1200 in case it needs to be repositioned or removed from the patient. In this state of partial deployment, the elongated first and second struts 1212a-b of the extended connectors 1210 space the base 1122 of the anchoring member 1120 and the outflow region of the valve support 1110 (FIG. 11A) apart from the edge 1708 of the capsule 1700 by a gap G.

Referring to FIG. 19, the gap G enables blood to flow through the prosthetic valve assembly 1150 while the device 1200 is only partially deployed. As a result, the device 1200 can be partially deployed to determine (a) whether the device 1200 is positioned correctly with respect to the native heart valve anatomy and (b) whether proper blood flow passes through the prosthetic valve assembly 1150 while the device 1200 is still retained by the delivery device 1700. As such, the device 1200 can be recaptured if it is not in the desired location and/or if the prosthetic valve is not functioning properly. This additional functionality is expected to significantly enhance the ability to properly position the device 1200 and assess, in vivo, whether the device 1200 will operate as intended, while retaining the ability to reposition the device 1200 for redeployment or remove the device 1200 from the patient.

Figure 20:
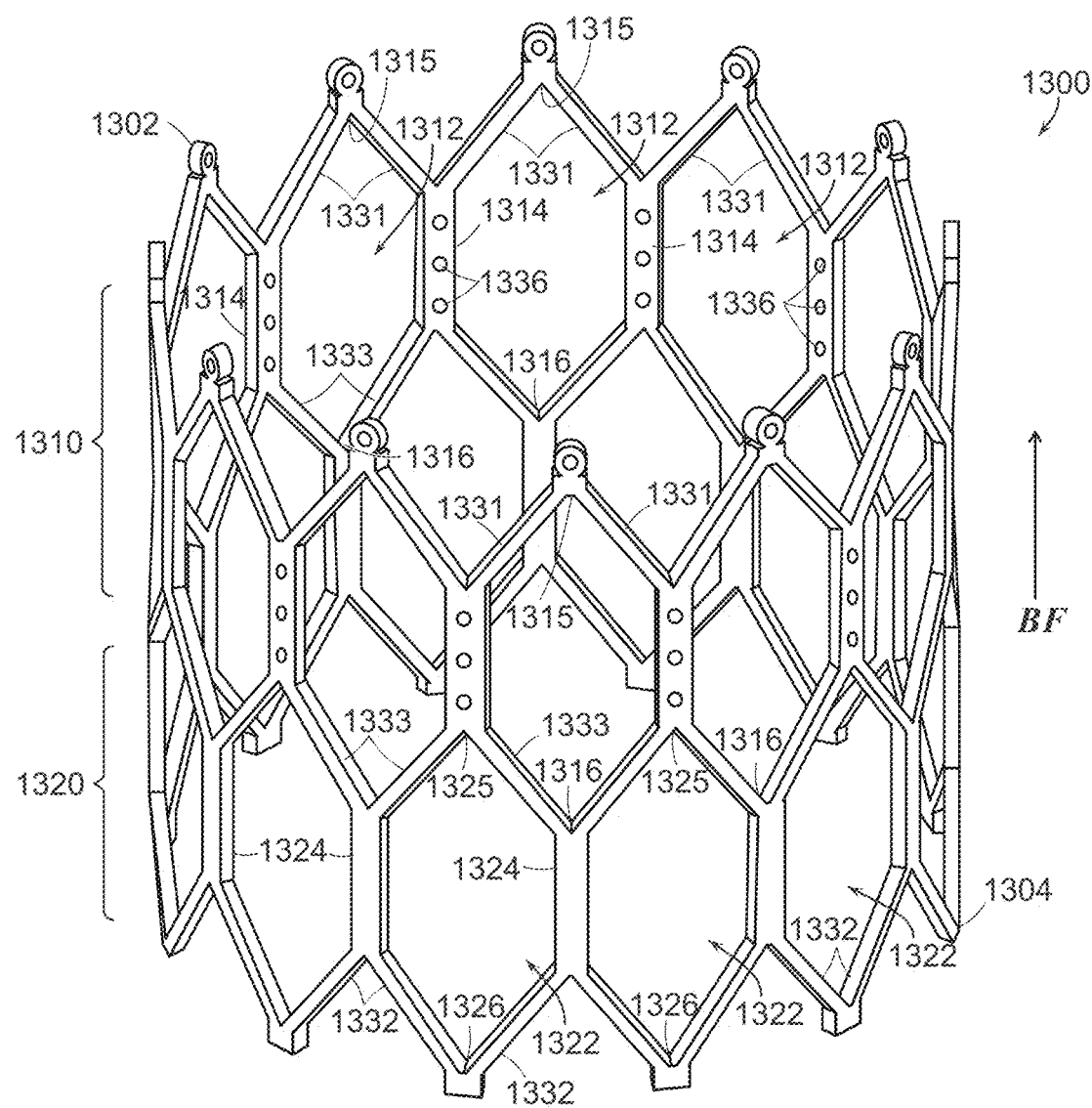
FIG. 20 is an isometric view of a valve support for use with prosthetic heart valve devices in accordance with the present technology.

FIG. 20 is an isometric view of a valve support 1300 in accordance with an embodiment of the present technology. The valve support 1300 can be an embodiment of the valve support 1110 described above with respect to FIGS. 11A-19. The valve support 1300 has an outflow region 1302, an inflow region 1304, a first row 1310 of first hexagonal cells 1312 at the outflow region 1302, and a second row 1320 of second hexagonal cells 1322 at the inflow region 1304. For purposes of illustration, the valve support shown in FIG. 20 is inverted compared to the valve support 1110 shown in FIGS. 11A-19 such that the blood flows through the valve support 1300 in the direction of arrow BF. In mitral valve applications, the valve support 1300 would be positioned within the anchoring member 1120 (FIG. 11A) such that the inflow region 1304 would correspond to orientation of the inflow region 1112 in FIG. 11A and the outflow region 1302 would correspond to the orientation of the outflow region 1114 in FIG. 11A.

Each of the first hexagonal cells 1312 includes a pair of first longitudinal supports 1314, a downstream apex 1315, and an upstream apex 1316. Each of the second hexagonal cells 1322 can include a pair of second longitudinal supports 1324, a downstream apex 1325, and an upstream apex 1326. The first and second rows 1310 and 1312 of the first and second hexagonal cells 1312 and 1322 are directly adjacent to each other. In the illustrated embodiment, the first longitudinal supports 1314 extend directly from the downstream apexes 1325 of the second hexagonal cells 1322, and the second longitudinal supports 1324 extend directly from the upstream apexes 1316 of the first hexagonal cells 1312. As a result, the first hexagonal cells 1312 are offset from the second hexagonal cells 1322 around the circumference of the valve support 1300 by half of the cell width.

In the embodiment illustrated in FIG. 20, the valve support 1300 includes a plurality of first struts 1331 at the outflow region 1302, a plurality of second struts 1332 at the inflow region 1304, and a plurality of third struts 1333 between the first and second struts 1331 and 1332. Each of the first struts 1331 extends from a downstream end of the first longitudinal supports 1314, and pairs of the first struts 1331 are connected together to form first downstream V-struts defining the downstream apexes 1315 of the first hexagonal cells 1312. In a related sense, each of the second struts 1332 extends from an upstream end of the second longitudinal supports 1324, and pairs of the second struts 1332 are connected together to form second upstream V-struts defining the upstream apexes 1326 of the second hexagonal cells 1322. Each of the third struts 1333 has a downstream end connected to an upstream end of the first longitudinal supports 1314, and each of the third struts 1333 has an upstream end connected to a downstream end of one of the second longitudinal supports 1324. The downstream ends of the third struts 1333 accordingly define a second downstream V-strut arrangement that forms the downstream apexes 1325 of the second hexagonal cells 1322, and the upstream ends of the third struts 1333 define a first upstream V-strut arrangement that forms the upstream apexes 1316 of the first hexagonal cells 1312. The third struts 1333, therefore, define both the first upstream V-struts of the first hexagonal cells 1312 and the second downstream V-struts of the second hexagonal cells 1322.

The first longitudinal supports 1314 can include a plurality of holes 1336 through which sutures can pass to attach a prosthetic valve assembly and/or a sealing member. In the embodiment illustrated in FIG. 20, only the first longitudinal supports 1314 have holes 1336. However, in other embodiments the second longitudinal supports 1324 can also include holes either in addition to or in lieu of the holes 1336 in the first longitudinal supports 1314.

Figure 21:
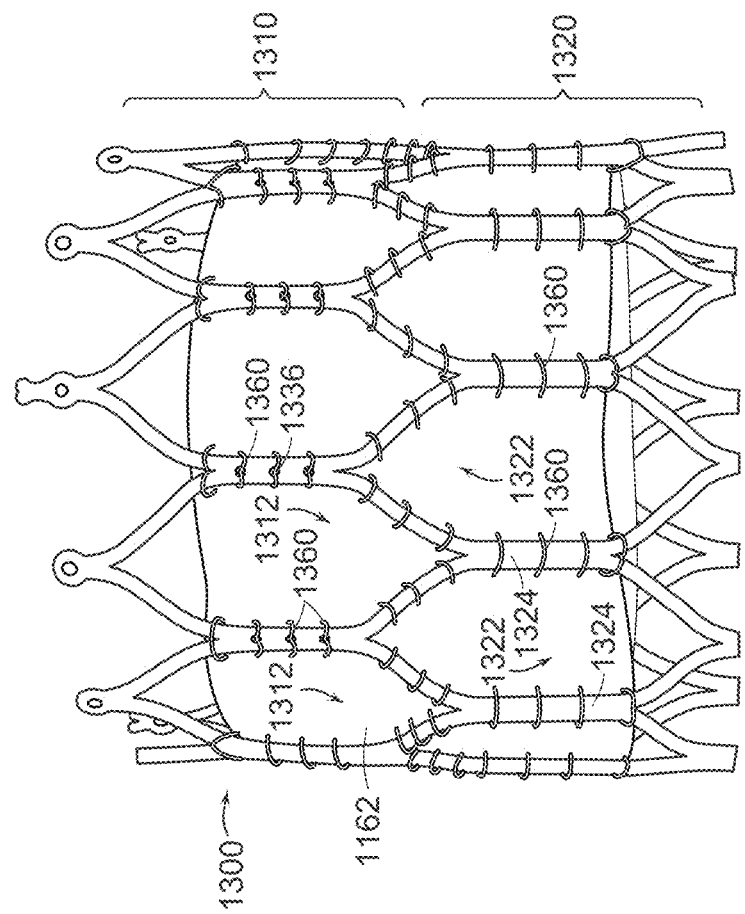
FIGS. 21 and 22 are side and bottom isometric views, respectively, of a prosthetic heart valve attached to the valve support of FIG. 20.
Figure 22:
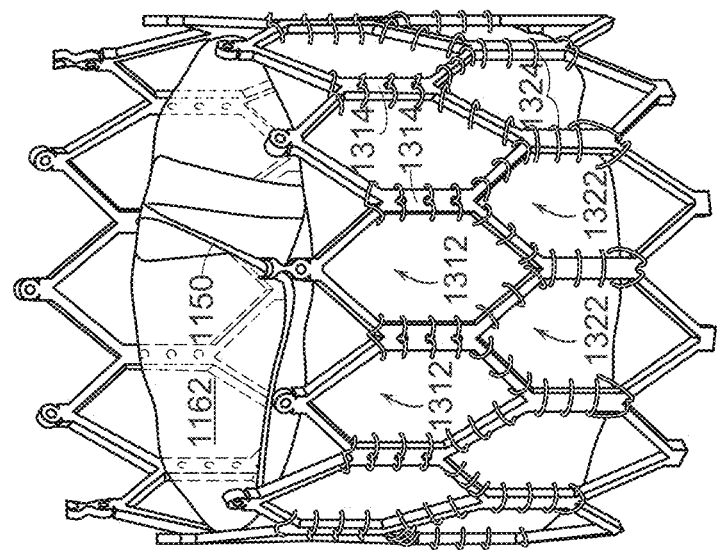

FIG. 21 is a side view and FIG. 22 is a bottom isometric view of the valve support 1300 with a first sealing member 1162 attached to the valve support 1300 and a prosthetic valve 1150 within the valve support 1300. The first sealing member 1162 can be attached to the valve support 1300 by a plurality of sutures 1360 coupled to the first longitudinal supports 1314 and the second longitudinal supports 1324. At least some of the sutures 1360 coupled to the first longitudinal supports 1314 pass through the holes 1336 to further secure the first sealing member 1162 to the valve support 1300.

Referring to FIG. 22, the prosthetic valve 1150 can be attached to the first sealing member 1162 and/or the first longitudinal supports 1314 of the valve support 1300. For example, the commissure portions of the prosthetic valve 1150 can be aligned with the first longitudinal supports 1314, and the sutures 1360 can pass through both the commissure portions of the prosthetic valve 1150 and the first sealing member 1162 where the commissure portions of the prosthetic valve 1150 are aligned with a first longitudinal support 1314. The inflow portion of the prosthetic valve 1150 can be sewn to the first sealing member 1162.

The valve support 1300 illustrated in FIGS. 20-22 is expected to be well suited for use with the device 1200 described above with reference to FIGS. 16-19. More specifically, the first struts 1331 cooperate with the extended connectors 1210 (FIGS. 16-19) of the device 1200 to separate the outflow portion of the prosthetic valve 1150 from the capsule 1700 (FIGS. 16-19) when the device 1200 is in a partially deployed state. The first struts 1331, for example, elongate when the valve support 1300 is not fully expanded (e.g., at least partially contained within the capsule 1700) and foreshorten when the valve support is fully expanded. This allows the outflow portion of the prosthetic valve 1150 to be spaced further apart from the capsule 1700 in a partially deployed state so that the prosthetic valve 1150 can at least partially function when the device 1200 (FIGS. 16-19) is in the partially deployed state. Therefore, the valve support 1300 is expected to enhance the ability to assess whether the prosthetic valve 1150 is fully operational in a partially deployed state.

Figure 23:
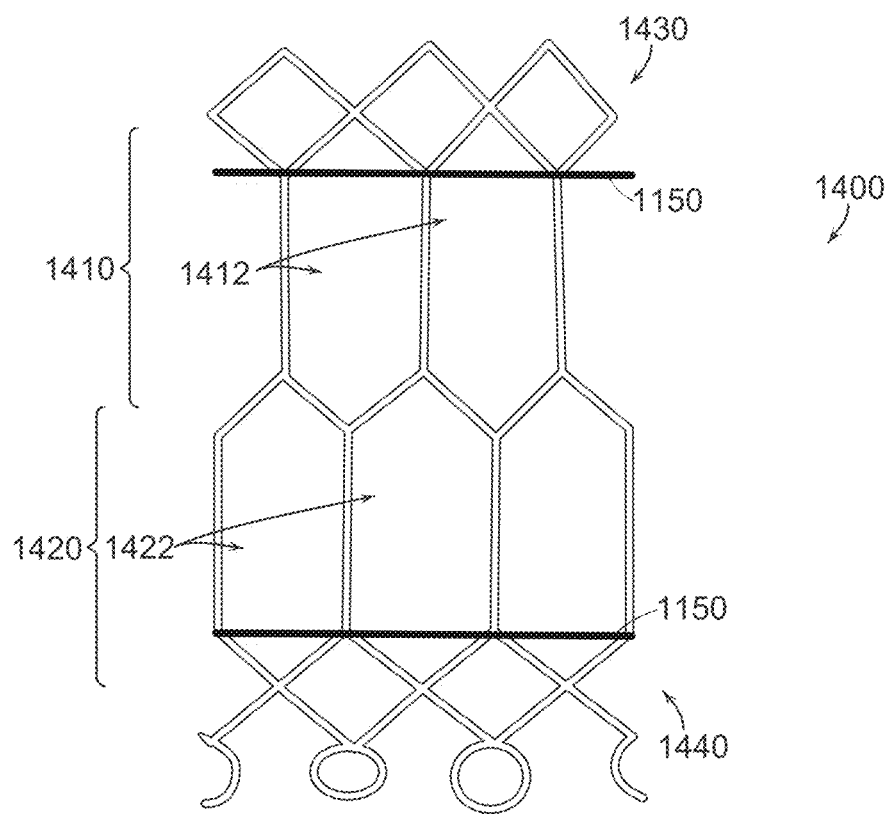
FIGS. 23 and 24 are side views schematically showing valve supports in accordance with additional embodiments of the present technology.
Figure 24:
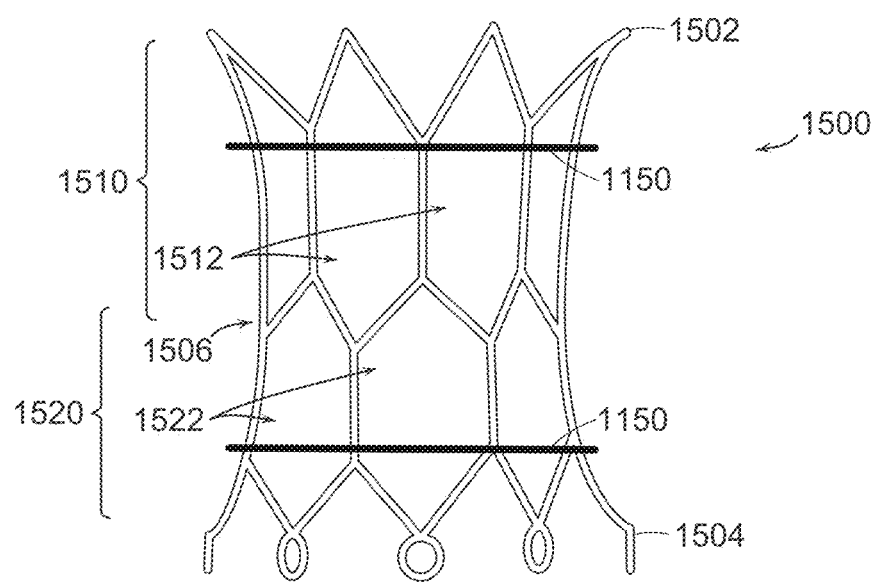

FIGS. 23 and 24 are schematic side views of valve supports 1400 and 1500, respectively, in accordance with other embodiments of the present technology. Referring to FIG. 23, the valve support 1400 includes a first row 1410 of first of hexagonal cells 1412 and a second row 1420 of second hexagonal cells 1422. The valve 1400 can further include a first row 1430 of diamond-shaped cells extending from the first hexagonal cells 1412 and a second row 1440 of diamond-shaped cells extending from the second hexagonal cells 1422. The additional diamond-shaped cells elongate in the low-profile state, and thus they can further space the prosthetic valve 1150 (shown schematically) apart from a capsule of a delivery device. Referring to FIG. 24, the valve support 1500 includes a first row 1510 of first hexagonal cells 1512 at an outflow region 1502 and a second row 1520 of second hexagonal cells 1522 at an inflow region 1504. The valve support 1500 is shaped such that an intermediate region 1506 (between the inflow and outflow regions 1502 and 1504) has a smaller cross-sectional area than that of the outflow region 1502 and/or the inflow region 1504. As such, the first row 1510 of first hexagonal cells 1512 flares outwardly in the downstream direction and the second row 1520 of second hexagonal cells 1522 flares outwardly in the upstream direction.

EXAMPLES

Several aspects of the present technology are set forth in the following examples.

1. A delivery system for delivering a prosthetic heart valve device into a heart of a human patient, the delivery system comprising:
   an elongated catheter body;
   a capsule carried by the elongated catheter body and configured to be moved between
      (a) a containment configuration for holding the prosthetic heart valve device and
      (b) a deployment configuration for at least partially deploying the prosthetic heart valve device;
   a cinching member slidably disposed within at least a portion of a distal region of the capsule;
   a plurality of tether elements extending through the cinching member and the catheter body to a proximal end thereof, wherein the tether elements are releasably coupled to the prosthetic heart valve; and
   wherein proximal retraction of the tether elements is configured to urge at least a portion of the prosthetic heart valve device toward a distal end portion of the cinching member to resheathe at least a portion of the prosthetic heart valve device and allow repositioning of the prosthetic heart valve device relative to a native valve after a portion of the prosthetic heart valve device has contacted tissue of the native valve of the heart of the patient.

2. The delivery system of example 1 wherein the tether elements are releasably attached to a ventricular end of the prosthetic heart valve device.

3. The delivery system of example 1 or 2 wherein the tether elements are removably coupled to hook elements on a ventricular end of the prosthetic heart valve device.

4. The delivery system of example 1 or 2 wherein each tether element extends through a first loop and a second loop on a ventricular end of the prosthetic heart valve device, and wherein the first and second loops are spaced circumferentially apart from each other on the ventricular end of the prosthetic heart valve device.

5. The delivery system of any one of examples 1-4, further comprising:
a handle assembly at a proximal portion of the elongated catheter body, the handle assembly having an actuator, wherein each tether element has a first end and a second end, wherein the first end is fixed and the second end is coupled to the actuator, and
wherein the actuator is configured to proximally retract and distally advance the tether elements.

6. The delivery system of any one of examples 1-5, further comprising a push rod extending through the catheter body and having a distal end portion coupled to the cinching member.

7. The delivery system of example 6 wherein the distal end portion of the push rod comprises a plurality of loops, and wherein the tether elements extend through the loops and through the push rod.

8. The delivery system of any one of examples 1-5, further comprising:
a distal platform movably positioned in the capsule, wherein the distal platform is configured to allow the prosthetic heart valve device to at least partially expand out of the capsule.

9. The delivery system of example 8 wherein the tether elements extend through eyelets on the distal platform and are removably coupled to corresponding engagement features of the prosthetic heart valve.

10. The delivery system of example 8 wherein the distal platform and the cinching member are fixed relative to a handle assembly at the proximal portion of the catheter body.

11. The delivery system of any one of examples 1-10 wherein the cinching member is axially movable relative to the capsule.

12. The delivery system of any one of examples 1-11 wherein the cinching member is independently movable with respect to the elongated catheter body and the capsule.

13. The delivery system of any one of examples 1-12 wherein the capsule has a first diameter and the cinching member has a second diameter less than the first diameter.

14. The delivery system of any one of examples 1-4, further comprising a handle assembly at a proximal portion of the elongated catheter body, the handle assembly having an actuator configured to pull and relax the tether elements.

15. The delivery system of example 14 wherein the actuator comprises a rotational actuator mechanism at the handle assembly.

16. The delivery system of any one of examples 1-15 wherein the plurality of tether elements comprises three tether elements.

17. The delivery system of any one of examples 1-16 wherein proximal retraction of the tether elements is configured to urge at least a portion of the prosthetic heart valve device into the distal end portion of the cinching member to resheathe at least a portion of the prosthetic heart valve device.

18. A delivery system, comprising:
an elongated catheter body having a distal portion and a proximal portion;
a handle assembly at the proximal portion of the elongated catheter body;
a delivery capsule coupled to the elongated catheter body and configured to be moved between a delivery arrangement for holding a prosthetic heart valve device and a deployment arrangement for at least partially deploying the prosthetic heart valve device into a heart of a human patient, wherein the delivery capsule has a first diameter;
a cinching member slidably disposed within at least a portion of a distal region of the catheter body and the delivery capsule, wherein the cinching member has a second diameter less than the first diameter and is axially movable with respect to the catheter body and the delivery capsule; and
a plurality of tether elements releasably coupled to the prosthetic heart valve, wherein the tether elements extend from the prosthetic heart valve device through the cinching member and the catheter body to the handle assembly,
wherein retraction of the tether elements toward the handle assembly is configured to cause a ventricular end of the prosthetic heart valve device to move from an at least partially deployed arrangement to a contracted arrangement having a third diameter less than the first diameter.

19. The delivery system of example 18 wherein the tether elements loop around engagement features at the ventricular end of the prosthetic heart valve device.

20. The delivery system of example 18 or 19 wherein each tether element extends from the distal end portion of the cinching member and through at least a first engagement feature and a second engagement feature on the ventricular end of the prosthetic heart valve device, and wherein the first and second engagement features are spaced circumferentially apart from each other on the ventricular end of the prosthetic heart valve device.

21. The delivery system of any one of examples 18-20 wherein the handle assembly includes an actuator operably coupled to the tethers, wherein the actuator is configured to proximally retract and distally advance the tether elements.

22. The delivery system of any one of examples 18-21, further comprising a platform slidably disposed in the delivery capsule, wherein the platform is positioned allow the prosthetic heart valve device to at least partially expand out of the delivery capsule, 23. A method for delivering a prosthetic heart valve device to a native mitral valve of a heart of a human patient, the method comprising:
positioning a delivery capsule of an elongated catheter body within the heart, the delivery capsule carrying the prosthetic heart valve device;
deploying the prosthetic heart valve device from the delivery capsule to allow the prosthetic heart valve device to radially expand against tissue of the native mitral valve;
extending a distal portion of a cinching member beyond a distal end of the delivery capsule;
retracting, via a handle assembly at a proximal portion of the elongated catheter body, a plurality of tether elements coupled to the prosthetic heart valve device, wherein the tether elements extend through the cinching member, and wherein retracting the tether elements at least partially contracts the prosthetic heart valve device to resheathe at least a portion of the prosthetic heart valve device; and
repositioning of the prosthetic heart valve device relative to the native mitral valve while the prosthetic heart valve device is at least partially sheathed.

24. The method of example 23 wherein retracting the tether elements contracts a ventricular portion of the prosthetic heart valve device to a first diameter less than an inner diameter of the delivery capsule.

25. The method of example 23 or 24 wherein retracting the tether elements moves at least a ventricular portion of the prosthetic heart valve device into the distal portion of the cinching member.

26. The method of any one of examples 23-25 wherein deploying the prosthetic heart valve device comprises fully expanding the prosthetic heart valve device before retracting the tether elements to at least partially resheathe the prosthetic heart valve device.

27. The method of any one of examples 23-26 wherein:
deploying the prosthetic heart valve device from the delivery capsule comprises sliding a platform in the delivery capsule toward the first configuration; and
retracting the plurality of tether elements allows a ventricular end portion of the prosthetic heart valve device to wrap at least partially around the platform.

28. The method of any one of examples 23-27, further comprising releasing the tether elements from the prosthetic heart valve device after fully deploying the prosthetic heart valve device.

29. The method of any one of examples 23-28 wherein retracting the plurality of tether elements comprises rotating an actuator at the handle assembly.

30. The method of any one of examples 23-28, further comprising manipulating an actuator of the handle assembly to pull and relax the tether elements.

31. A delivery system for delivering a prosthetic heart valve device into a heart of a human patient, the delivery system comprising:
an elongated catheter body;
a capsule carried by the elongated catheter body and configured to be moved between
(a) a containment configuration for holding the prosthetic heart valve device and
(b) a deployment configuration for at least partially deploying the prosthetic heart valve device;
a cinching member slidably disposed within at least a portion of a distal region of the capsule;
at least one tether element extending through the cinching member and the catheter body to a proximal end thereof, wherein the tether element is releasably coupled to the prosthetic heart valve;
a tethering assembly fixedly attached to the prosthetic heart valve device, wherein the tethering assembly comprises a plurality of arm members extending from a ventricular end portion of the prosthetic heart valve device and an engagement feature coupled to the arm members, wherein the engagement feature is releasably attached to the tether element; and
wherein proximal retraction of the tether element is configured to urge at least a portion of the prosthetic heart valve device into a distal end portion of the cinching member to resheathe at least a portion of the prosthetic heart valve device and allow repositioning of the prosthetic heart valve device relative to a native valve after a portion of the prosthetic heart valve device has contacted tissue of the native valve of the heart of the patient.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A method comprising:
positioning a delivery capsule of an elongated catheter body within a heart, the delivery capsule carrying a prosthetic heart valve device;
deploying the prosthetic heart valve device from the delivery capsule to allow the prosthetic heart valve device to radially expand against tissue of the native mitral valve;
extending a distal portion of a cinching member beyond a distal end of the delivery capsule;
extending a distal platform slidably disposed within the cinching member beyond a distal end of the cinching member;
retracting, via a handle assembly at a proximal portion of the elongated catheter body, a plurality of tether elements coupled to the prosthetic heart valve device, wherein the tether elements extend through the cinching member, and wherein retracting the tether elements at least partially contracts the prosthetic heart valve device to resheathe at least a portion of the prosthetic heart valve device; and
repositioning the prosthetic heart valve device relative to the native mitral valve while the prosthetic heart valve device is at least partially sheathed.

2. The method of claim 1, wherein retracting the plurality of tether elements contracts a ventricular portion of the prosthetic heart valve device to a diameter less than an inner diameter of the delivery capsule.

3. The method of claim 1, wherein retracting the plurality of tether elements moves at least a ventricular portion of the prosthetic heart valve device into the distal portion of the cinching member.

4. The method of claim 1, wherein deploying the prosthetic heart valve device comprises fully expanding the prosthetic heart valve device before retracting the tether elements to at least partially resheathe the prosthetic heart valve device.

5. The method of claim 1, wherein:
deploying the prosthetic heart valve device from the delivery capsule comprises distally sliding the distal platform in the delivery capsule; and
retracting the plurality of tether elements allows a ventricular end portion of the prosthetic heart valve device to wrap at least partially around the distal platform.

6. The method of claim 5, wherein the plurality of tether elements extend through eyelets on the platform and are removably coupled to corresponding engagement features of the prosthetic heart valve.

7. The delivery system of claim 5, wherein the platform and the cinching member are fixed relative to the handle assembly at the proximal portion of the elongated catheter body.

8. The method of claim 1, further comprising:
fully deploying the prosthetic heart valve device after repositioning the prosthetic heart valve device; and
releasing the tether elements from the prosthetic heart valve device after fully deploying the prosthetic heart valve device.

9. The method of claim 1, wherein retracting the plurality of tether elements comprises rotating an actuator at the handle assembly.

10. The method of claim 1, further comprising manipulating an actuator of the handle assembly to pull and relax the plurality of tether elements.

11. The method of claim 1, wherein a tethering assembly is fixedly attached to the prosthetic heart valve device, wherein the tethering assembly comprises a plurality of arm members extending from a ventricular end portion of the prosthetic heart valve device and an engagement feature coupled to the arm members, and wherein the engagement feature is releasably attached to the tether element.

12. The method of claim 1, wherein the plurality of tether elements are configured to be removably coupled to hook elements on a ventricular end of the prosthetic heart valve device.

13. The method of claim 1, wherein each tether element of the plurality of tether elements is configured to extend through a first loop and a second loop on a ventricular end of the prosthetic heart valve device, and wherein the first and second loops are spaced circumferentially apart from each other on the ventricular end of the prosthetic heart valve device.

14. The method of claim 1, wherein each tether element has a first end and a second end, wherein the first end is fixed and the second end is coupled to the actuator.

15. The method of claim 1, wherein a push rod extends through the elongated catheter body, and wherein the push rod comprises a distal end portion coupled to the cinching member.

16. The method of claim 15, wherein the distal end portion of the push rod comprises a plurality of loops, and wherein the plurality of tether elements extend through the loops and through the push rod.

* * * * *